United States Patent
Valliant et al.

(10) Patent No.: US 10,758,636 B2
(45) Date of Patent: Sep. 1, 2020

(54) RESIDUALIZING LINKERS AND USES THEREOF

(71) Applicants: Centre for Probe Development and Commercialization, Hamilton (CA); John Fitzmaurice Valliant, Ancaster (CA); Eric Steven Burak, Dundas (CA); Neil Grant Cockburn, Guelph (CA); Alla Darwish, Kitchener (CA); Joel Adamson Drewry, Mississauga (CA); John Richard Forbes, Burlington (CA); Meiduo Hu, Toronto (CA); Ryan Wayne Simms, Toronto (CA); Karin Ann Stephenson, Burlington (CA); Tao Wu, Ancaster (CA)

(72) Inventors: John Fitzmaurice Valliant, Ancaster (CA); Eric Steven Burak, Dundas (CA); Neil Grant Cockburn, Guelph (CA); Alla Darwish, Kitchener (CA); Joel Adamson Drewry, Mississauga (CA); John Richard Forbes, Burlington (CA); Meiduo Hu, Toronto (CA); Ryan Wayne Simms, Toronto (CA); Karin Ann Stephenson, Burlington (CA); Tao Wu, Ancaster (CA)

(73) Assignee: CENTRE FOR PROBE DEVELOPMENT AND COMMERCIALIZATION (CA)

( * ) Notice: Subject to any disclaimer, the term of this patent is extended or adjusted under 35 U.S.C. 154(b) by 168 days.

(21) Appl. No.: 15/036,008

(22) PCT Filed: Nov. 12, 2014

(86) PCT No.: PCT/US2014/065288
§ 371 (c)(1),
(2) Date: May 11, 2016

(87) PCT Pub. No.: WO2015/073575
PCT Pub. Date: May 21, 2015

(65) Prior Publication Data
US 2016/0279272 A1    Sep. 29, 2016

Related U.S. Application Data

(60) Provisional application No. 61/903,107, filed on Nov. 12, 2013.

(51) Int. Cl.
*A61K 51/08* (2006.01)
*A61K 51/10* (2006.01)
*A61K 45/06* (2006.01)

(52) U.S. Cl.
CPC .......... *A61K 51/1093* (2013.01); *A61K 45/06* (2013.01); *A61K 51/088* (2013.01); *A61K 51/103* (2013.01); *A61K 51/1045* (2013.01)

(58) Field of Classification Search
CPC .... A61K 51/00; A61K 51/1093; A61K 51/08; A61K 51/088; A61K 51/103; A61K 51/1045; A61K 45/00; A61K 45/06
USPC .......... 424/1.11, 1.49, 1.65, 1.69, 1.73, 1.81, 424/1.85, 1.89, 9.1, 9.2, 9.3, 9.4, 9.5, 9.6; 514/1, 1.1; 530/300; 534/7, 10–16
See application file for complete search history.

(56) References Cited

U.S. PATENT DOCUMENTS

| | | | |
|---|---|---|---|
| 5,175,343 A | 12/1992 | Fritzberg et al. | |
| 6,180,370 B1 | 1/2001 | Queen et al. | |
| 2005/0250700 A1* | 11/2005 | Sato | C07K 7/06 514/8.1 |
| 2014/0065288 A1 | 3/2014 | Brown et al. | |

FOREIGN PATENT DOCUMENTS

| | | | |
|---|---|---|---|
| WO | WO-92/11858 A1 | 7/1992 | |
| WO | WO-9222324 A1 | 12/1992 | |
| WO | WO-93/25240 A2 | 12/1993 | |
| WO | WO-9846645 A2 | 10/1998 | |
| WO | WO-01/51095 A2 | 7/2001 | |
| WO | WO-2012/122420 A2 | 9/2012 | |
| WO | WO-2013/105753 A1 | 7/2013 | |
| WO | WO-2013148189 A1 * | 10/2013 | ........... G01N 33/532 |

OTHER PUBLICATIONS

Vaidyanathan et al, Bioconjugate Chemistry, vol. 17, pp. 1085-1092. (Year: 2006).*
International Search Report and Written Opinion for International Application No. PCT/US14/65288, dated Jun. 3, 2015 (16 pages).
Invitation to Pay Additional Fees for International Application No. PCT/US14/65288, dated Mar. 12, 2015 (3 pages).
Vaidyanathan et al., "N epsilon-(3-[*1]Iodobenzoyl)-Lys5-N alpha-maleimido-Gly1-GEEEK ([*I]IB-Mal-D-GEEEK): a radioiodinated prosthetic group containing negatively charged D-glutamates for labeling internalizing monoclonal antibodies," Bioconjug Chem. 17(4):1085-92 (2006).

(Continued)

*Primary Examiner* — D. L. Jones
(74) *Attorney, Agent, or Firm* — Goodwin Procter LLP

(57) ABSTRACT

The present invention relates to conjugates including a residualizing linker, methods for their production, and uses thereof.

1 Claim, 6 Drawing Sheets
Specification includes a Sequence Listing.

(56) References Cited

OTHER PUBLICATIONS

International Preliminary Report on Patentability for International Application No. PCT/US2014/065288, dated May 17, 2016 (7 pages).
Doern et al., "Characterization of inhibitory anti-insulin-like growth factor receptor antibodies with different epitope specificity and ligand-blocking properties," J Biol Chem. 284(15):10254-67 (2009).
Gualberto et al., "Development of the monoclonal antibody figitumumab, targeting the insulin-like growth factor-1 receptor, for the treatment of patients with non-small-cell lung cancer," Clin Lung Cancer. 10(4):273-80 (2009).
Vaidyanathan et al., "Evaluation of an anti-p185(HER2) (scFv-C(H)2-C(H)3)2 fragment following radioiodination using two different residualizing labels: SGMIB and IB-Mal-D-GEEEK," available in PMC Aug. 1, 2010, published in final edited form as: Nucl Med Biol. 36(6):671-80 (2009) (19 pages).
Berge et al. J. Pharmaceutical Sciences, Pharmaceutical Salts: Properties, Selection, and Use. Wley-VCH, 2008, 1977, vol. 66, pp. 1-19.
Brinkmann et al. "Phage Display of Disulfide-Stabilized Fv Fragments" J. Immunol. Methods, 1995, vol. 182, pp. 41-50.
Greene, Protective Groups in Organic Synthesis. Third Edition by Theodora W. Greene and Peter G. M. Wuts. John Wiley & Sons, New York, 1999. (52 pages).
Harlow et al. Antibodies: A Laboratory Manual. Cold Spring Harbor Laboratory Press, 1988, p. 220.
R. Langer "New methods of drug delivery" Science, 1990, vol. 249, pp. 1527-1533.
Morrison "Transfectomas Provide Novel Chimeric Antibodies" Science, 1985, vol. 229, pp. 1202-1207.
Rivera-Monroy Z et al: "Fluorescent isotope-coded affinity tag (FCAT) I: Design and synthesis", Bioorganic Chemistry, Academic Press Inc., New York, NY, US, vol. 36, No. 6, 1, pp. 299-311, Dec. 2008.
Segal et al. "Introduction: bispecific antibodies" J. Immunol. Methods, 2001, vol. 248, pp. 1-6.
Tutt et al. Trispecific F(ab')3 derivatives that use cooperative signaling via the TCR/CD3 complex and CD2 to activate and redirect resting cytotoxic T cells, J Immunol Jul. 1, 1991, 147 (1) pp. 60-69.
Ward et al. Binding activities of a repertoire of single, immunoglobulin variable domains secreted from *Escherichia coli*, Nature, 1989, vol. 341, pp. 544-546.

* cited by examiner

CDR-H1 (SEQ ID NO:1):
Gly Phe Thr Phe Ser Ser Tyr Ala Met Asn

CDR-H2 (SEQ ID NO:2):
Ala Ile Ser Gly Ser Gly Gly Thr Thr Phe Tyr Ala Asp Ser Val Lys

CDR-H3 (SEQ ID NO:3):
Asp Leu Gly Trp Ser Asp Ser Tyr Tyr Tyr Tyr Gly Met Asp Val

CDR-L1 (SEQ ID NO:4):
Arg Ala Ser Gln Gly Ile Arg Asn Asp Leu Gly

CDR-L2 (SEQ ID NO:5):
Ala Ala Ser Arg Leu His Arg

CDR-L3 (SEQ ID NO:6):
Leu Gln His Asn Ser Tyr Pro Cys Ser Phe

Figure 3

Heavy Chain variable domain (SEQ ID NO:7):
Val Gln Leu Leu Glu Ser Gly Gly Gly Leu Val Gln Pro Gly Gly Ser Leu Arg Leu Ser
Cys Thr Ala Ser Gly Phe Thr Phe Ser Ser Tyr Ala Met Asn Trp Val Arg Gln Ala Pro
Gly Lys Gly Leu Glu Trp Val Ser Ala Ile Ser Gly Ser Gly Gly Thr Thr Phe Tyr Ala
Asp Ser Val Lys Gly Arg Phe Thr Ile Ser Arg Asp Asn Ser Arg Thr Thr Leu Tyr Leu
Gln Met Asn Ser Leu Arg Ala Glu Asp Thr Ala Val Tyr Tyr Cys Ala Lys Asp Leu Gly
Trp Ser Asp Ser Tyr Tyr Tyr Tyr Tyr Gly Met Asp Val Trp Gly Gln Gly Thr Thr Val
Thr Val Ser Ser Light Chain variable domain (SEQ ID NO:8):
Asp Ile Gln Met Thr Gln Phe Pro Ser Ser Leu Ser Ala Ser Val Gly Asp Arg Val Thr
Ile Thr Cys Arg Ala Ser Gln Gly Ile Arg Asn Asp Leu Gly Trp Tyr Gln Gln Lys Pro
Gly Lys Ala Pro Lys Arg Leu Ile Tyr Ala Ala Ser Arg Leu His Arg Gly Val Pro Ser
Arg Phe Ser Gly Ser Gly Ser Gly Thr Glu Phe Thr Leu Thr Ile Ser Ser Leu Gln Pro
Glu Asp Phe Ala Thr Tyr Tyr Cys Leu Gln His Asn Ser Tyr Pro Cys Ser Phe Gly Gln
Gly Thr Lys Leu Glu Ile Lys

Figure 4

Heavy Chain (SEQ ID NO:9):
Glu Val Gln Leu Leu Glu Ser Gly Gly Gly Leu Val Gln Pro Gly Gly Ser Leu Arg Leu
Ser Cys Thr Ala Ser Gly Phe Thr Phe Ser Ser Tyr Ala Met Asn Trp Val Arg Gln Ala
Pro Gly Lys Gly Leu Glu Trp Val Ser Ala Ile Ser Gly Ser Gly Gly Thr Thr Phe Tyr
Ala Asp Ser Val Lys Gly Arg Phe Thr Ile Ser Arg Asp Asn Ser Arg Thr Thr Leu Tyr
Leu Gln Met Asn Ser Leu Arg Ala Glu Asp Thr Ala Val Tyr Tyr Cys Ala Lys Asp Leu
Gly Trp Ser Asp Ser Tyr Tyr Tyr Tyr Gly Met Asp Val Trp Gly Gln Gly Thr Thr
Val Thr Val Ser Ser Ala Ser Thr Lys Gly Pro Ser Val Phe Pro Leu Ala Pro Cys Ser
Arg Ser Thr Ser Glu Ser Thr Ala Ala Leu Gly Cys Leu Val Lys Asp Tyr Phe Pro Glu
Pro Val Thr Val Ser Trp Asn Ser Gly Ala Leu Thr Ser Gly Val His Thr Phe Pro Ala
Val Leu Gln Ser Ser Gly Leu Tyr Ser Leu Ser Ser Val Val Thr Val Pro Ser Ser Asn
Phe Gly Thr Gln Thr Tyr Thr Cys Asn Val Asp His Lys Pro Ser Asn Thr Lys Val Asp
Lys Thr Val Glu Arg Lys Cys Cys Val Glu Cys Pro Pro Cys Pro Ala Pro Pro Val Ala
Gly Pro Ser Val Phe Leu Phe Pro Pro Lys Pro Lys Asp Thr Leu Met Ile Ser Arg Thr
Pro Glu Val Thr Cys Val Val Val Asp Val Ser His Glu Asp Pro Glu Val Gln Phe Asn
Trp Tyr Val Asp Gly Val Glu Val His Asn Ala Lys Thr Lys Pro Arg Glu Glu Gln Phe
Asn Ser Thr Phe Arg Val Val Ser Val Leu Thr Val Val His Gln Asp Trp Leu Asn Gly
Lys Glu Tyr Lys Cys Lys Val Ser Asn Lys Gly Leu Pro Ala Pro Ile Glu Lys Thr Ile
Ser Lys Thr Lys Gly Gln Pro Arg Glu Pro Gln Val Tyr Thr Leu Pro Pro Ser Arg Glu
Glu Met Thr Lys Asn Gln Val Ser Leu Thr Cys Leu Val Lys Gly Phe Tyr Pro Ser Asp
Ile Ala Val Glu Trp Glu Ser Asn Gly Gln Pro Glu Asn Asn Tyr Lys Thr Thr Pro Pro
Met Leu Asp Ser Asp Gly Ser Phe Phe Leu Tyr Ser Lys Leu Thr Val Asp Lys Ser Arg
Trp Gln Gln Gly Asn Val Phe Ser Cys Ser Val Met His Glu Ala Leu His Asn His Tyr

Figure 5

Light Chain (SEQ ID NO:10):
Asp Ile Gln Met Thr Gln Phe Pro Ser Ser Leu Ser Ala Ser Val Gly Asp Arg Val Thr
Ile Thr Cys Arg Ala Ser Gln Gly Ile Arg Asn Asp Leu Gly Trp Tyr Gln Gln Lys Pro
Gly Lys Ala Pro Lys Arg Leu Ile Tyr Ala Ala Ser Arg Leu His Arg Gly Val Pro Ser
Arg Phe Ser Gly Ser Gly Ser Gly Thr Glu Phe Thr Leu Thr Ile Ser Ser Leu Gln Pro
Glu Asp Phe Ala Thr Tyr Tyr Cys Leu Gln His Asn Ser Tyr Pro Cys Ser Phe Gly Gln
Gly Thr Lys Leu Glu Ile Lys Arg Thr Val Ala Ala Pro Ser Val Phe Ile Phe Pro Pro
Ser Asp Glu Gln Leu Lys Ser Gly Thr Ala Ser Val Val Cys Leu Leu Asn Asn Phe Tyr
Pro Arg Glu Ala Lys Val Gln Trp Lys Val Asp Asn Ala Leu Gln Ser Gly Asn Ser Gln
Glu Ser Val Thr Glu Gln Asp Ser Lys Asp Ser Thr Tyr Ser Leu Ser Ser Thr Leu Thr
Leu Ser Lys Ala Asp Tyr Glu Lys His Lys Val Tyr Ala Cys Glu Val Thr His Gln Gly
Leu Ser Ser Pro Val Thr Lys Ser Phe Asn Arg Gly Glu Cys

Figure 6

RESIDUALIZING LINKERS AND USES THEREOF

CROSS REFERENCE TO RELATED APPLICATIONS

This application claims the benefit of U.S. Provisional Application No. 61/903,107, filed Nov. 12, 2013, which is hereby incorporated by reference in its entirety.

REFERENCE TO A SEQUENCE LISTING

This application contains a Sequence Listing in computer readable form. The computer readable form is incorporated herein by reference.

BACKGROUND

Biological molecules targeting proteins that undergo internalization offer a number of advantages. When labeled with either a diagnostic or therapeutic agent they carry the label/prosthetic group inside the cell and once inside the conjugate can enhance contrast for diagnostic agents and/or deliver its therapeutic effects. The process of internalization can also enhance cytotoxic potency as in the case of radioimmunotherapy when radioisotopes with short effective ranges are used.

Labeled biological molecules or conjugates are typically prepared by using a linker to append the label to the biological molecule so that minimal damage is done to the compound and affinity is maintained for the target. Biological molecules labeled in this fashion and then internalized can undergo rapid intracellular degradation. This is an enzyme-catalyzed event that breaks the conjugate down into small peptides and/or individual amino acids. As a result the label is liberated from the conjugate and often egresses from the target cells. In the case of diagnostic agents this significantly lowers target to non-target ratios and with respect to therapeutic agents this can lead to significant undesirable off target toxicity.

Residualizing linkers are designed to retain the label intracellularly after lysosomal degradation of the internalized biological conjugate. This results in overall greater retention in the cells leading to better target-to-non-target ratios and therapeutic effects.

SUMMARY OF THE INVENTION

The present invention is directed to linkers that minimize egress of the label by attaching it to a metabolically resistant negatively charged or zwitterionic backbone that can easily be attached to biological molecules. The linkers described herein are comprised of three parts including a linker component, a residualizing backbone and the detection agent. All three components are easily assembled in three simple versatile synthetic steps following preparation of the polyanionic or zwitterionic backbone that is comprised of different classes of compounds including alpha and beta glutamic acid residues for polyanionic species, and a polyamine backbone wherein the secondary amines have been derivatized with short-chain acidic residues to generate zwitterionic species. Linker components include those which are linear, cyclic or aromatic with an activated terminus to react with free amine groups on biological compounds. The label includes radiohalogens, radiometals or luminescent compounds. The flexibility, ease of synthesis and enhanced residualization of the new linkers dramatically improves the utility of this conjugate for internalizing and retaining biological therapeutic agents.

Accordingly, in a first aspect the invention features a conjugate including a polypeptide linked to a detection agent, the conjugate having the structure:

Formula I

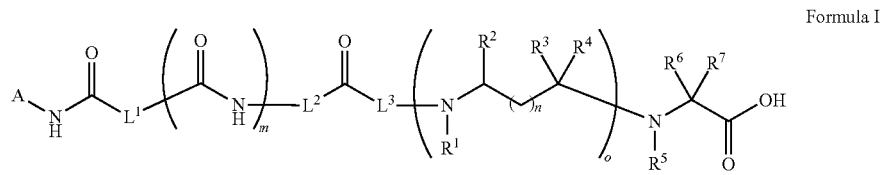

or a salt thereof, wherein A-NH— is a polypeptide;

$L^1$ and $L^2$ are independently absent, optionally substituted C1-C6 alkyl, optionally substituted C1-C6 heteroalkyl, optionally substituted C2-C6 alkenyl, optionally substituted C2-C6 heteroalkenyl, optionally substituted C2-C6 alkynyl, optionally substituted C2-C6 heteroalkynyl, optionally substituted C3-C10 cycloalkyl, optionally substituted C4-C10 cycloalkenyl, optionally substituted C4-C10 cycloalkynyl, optionally substituted oxime, optionally substituted hydrazone, optionally substituted aryl, optionally substituted heterocyclic, optionally substituted C2-C100 polyethylene glycol, or $L^4$-B;

$L^3$ is absent or optionally substituted C1-C6 alkyl;

m is 0 or 1;

each $R^1$ and $R^2$ are independently hydrogen, —CH$_2$CO$_2$H, or —CH$_2$CH$_2$CO$_2$H;

each $R^3$ and $R^4$ is independently hydrogen or $R^3$ and $R^4$ combine to form C=O;

n is 0 or 1;

o is an integer between 1 and 10;

$R^5$ is hydrogen or $L^4$-B;

$R^6$ and $R^7$ are independently hydrogen, optionally substituted C1-C6 hetereoalkyl, or $L^4$-B;

$L^4$ is independently absent, optionally substituted C1-C6 alkyl, optionally substituted C1-C6 heteroalkyl, optionally substituted C2-C6 alkenyl, optionally substituted C2-C6 heteroalkenyl, optionally substituted C2-C6 alkynyl, optionally substituted C2-C6 heteroalkynyl, optionally substituted C3-C10 cycloalkyl, optionally substituted C4-C10 cycloalkenyl, optionally substituted C4-C10 cycloalkynyl, optionally substituted oxime, optionally substituted hydrazone, optionally substituted aryl, or optionally substituted heterocyclic;

B is an organic moiety including a detection agent;

wherein at least one $R^1$ or $R^2$ is —CH$_2$CO$_2$H or CH$_2$CH$_2$CO$_2$H;

at least one of $L^1$ and $L^2$ are present and when $L^1$ or $L^2$ are absent, m is 0;

and one and only one of $L^1$, $L^2$, $R^5$, $R^6$, and $R^7$ is $L^4$-B.

In another aspect, the invention features a compound having the structure:

Formula II

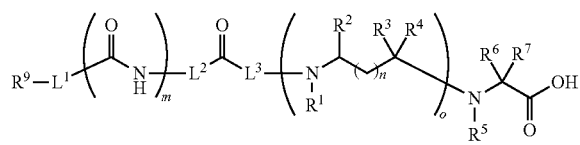

or a salt thereof, $L^1$ and $L^2$ are independently absent, optionally substituted C1-C6 alkyl, optionally substituted C1-C6 heteroalkyl, optionally substituted C2-C6 alkenyl, optionally substituted C2-C6 heteroalkenyl, optionally substituted C2-C6 alkynyl, optionally substituted C2-C6 heteroalkynyl, optionally substituted C3-C10 cycloalkyl, optionally substituted C4-C10 cycloalkenyl, optionally substituted C4-C10 cycloalkynyl, optionally substituted oxime, optionally substituted hydrazone, optionally substituted aryl, optionally substituted heterocyclic, optionally substituted C2-C100 polyethylene glycol, or $L^4$-B;

$L^3$ is absent or optionally substituted C1-C6 alkyl;

m is 0 or 1;

each $R^1$ and $R^2$ are independently hydrogen, —$CH_2CO_2H$, or —$CH_2CH_2CO_2H$;

each $R^3$ and $R^4$ is independently hydrogen or $R^3$ and $R^4$ combine to form C=O;

n is 0 or 1;

o is an integer between 1 and 10;

$R^5$ is hydrogen or $L^4$-B;

$R^6$ and $R^7$ are independently hydrogen, optionally substituted C1-C6 hetereoalkyl, or $L^4$-B;

$R^9$ is —$CO_2H$, —N=C=O, —N=C=S,

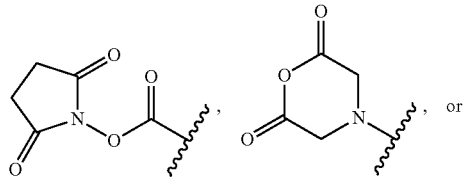

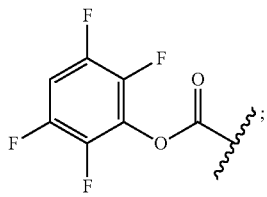

$L^4$ is independently absent, optionally substituted C1-C6 alkyl, optionally substituted C1-C6 heteroalkyl, optionally substituted C2-C6 alkenyl, optionally substituted C2-C6 heteroalkenyl, optionally substituted C2-C6 alkynyl, optionally substituted C2-C6 heteroalkynyl, optionally substituted C3-C10 cycloalkyl, optionally substituted C4-C10 cycloalkenyl, optionally substituted C4-C10 cycloalkynyl, optionally substituted oxime, optionally substituted hydrazone, optionally substituted aryl, or optionally substituted heterocyclic;

B is an organic moiety including a detection agent;

wherein at least one $R^1$ or $R^2$ is —$CH_2CO_2H$ or $CH_2CH_2CO_2H$;

at least one of $L^1$ and $L^2$ are present and when $L^1$ or $L^2$ are absent, m is 0;

and one and only one of $L^1$, $L^2$, $R^5$, $R^6$, and $R^7$ is $L^4$-B.

In another aspect, the invention features a method of producing a polypeptide conjugate, the method including reacting a compound of formula II:

Formula II

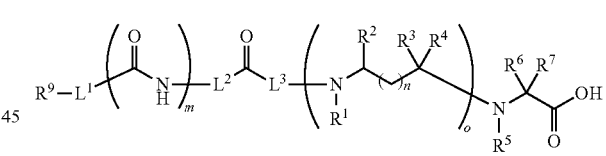

with a polypeptide, wherein the polypeptide has one or more primary amine groups, under conditions to produce a compound of formula I:

Formula I

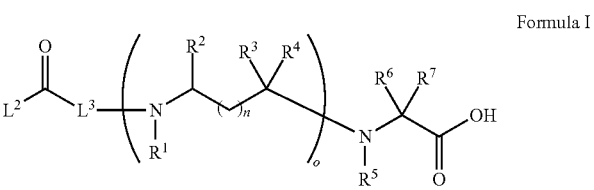

or a salt thereof, wherein A-NH— is a polypeptide;

$L^1$ and $L^2$ are independently absent, optionally substituted C1-C6 alkyl, optionally substituted C1-C6 heteroalkyl, optionally substituted C2-C6 alkenyl, optionally substituted C2-C6 heteroalkenyl, optionally substituted C2-C6 alkynyl, optionally substituted C2-C6 heteroalkynyl, optionally substituted C3-C10 cycloalkyl, optionally substituted C4-C10 cycloalkenyl, optionally substituted C4-C10 cycloalkynyl, optionally substituted oxime, optionally substituted hydrazone, optionally substituted aryl, optionally substituted heterocyclic, optionally substituted C2-C100 polyethylene glycol, or $L^4$-B;

$L^3$ is absent or optionally substituted C1-C6 alkyl;

m is 0 or 1;

each $R^1$ and $R^2$ are independently hydrogen, —CH$_2$CO$_2$H, or —CH$_2$CH$_2$CO$_2$H;

each $R^3$ and $R^4$ is independently hydrogen or $R^3$ and $R^4$ combine to form C=O;

n is 0 or 1;

o is an integer between 1 and 10;

$R^5$ is hydrogen or $L^4$-B;

$R^6$ and $R^7$ are independently hydrogen, optionally substituted C1-C6 hetereoalkyl, or $L^4$-B;

$R^9$ is —CO$_2$H, —N=C=O, —N=C=S,

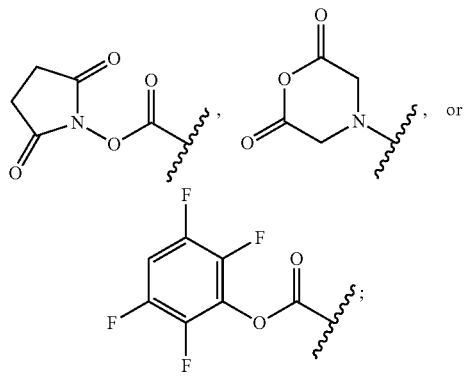

$L^4$ is independently absent, optionally substituted C1-C6 alkyl, optionally substituted C1-C6 heteroalkyl, optionally substituted C2-C6 alkenyl, optionally substituted C2-C6 heteroalkenyl, optionally substituted C2-C6 alkynyl, optionally substituted C2-C6 heteroalkynyl, optionally substituted C3-C10 cycloalkyl, optionally substituted C4-C10 cycloalkenyl, optionally substituted C4-C10 cycloalkynyl, optionally substituted oxime, optionally substituted hydrazone, optionally substituted aryl, or optionally substituted heterocyclic;

B is an organic moiety including a detection agent;

wherein at least one $R^1$ or $R^2$ is —CH$_2$CO$_2$H or CH$_2$CH$_2$CO$_2$H;

at least one of $L^1$ and $L^2$ are present and when $L^1$ or $L^2$ are absent, m is 0;

and one and only one of $L^1$, $L^2$, $R^5$, $R^6$, and $R^7$ is $L^4$-B.

In some embodiments, the detection agent is a radionuclide (e.g., an alpha, beta, or gamma emitter), a magnetic agent, or a bioluminescent agent.

In certain embodiments, the radionuclide is $^{18}$F, $^{75}$Br, $^{76}$Br, $^{77}$Br, $^{123}$I, $^{124}$I, $^{125}$I, $^{131}$I, or $^{211}$At.

In other embodiments, B is an organic moiety including an optionally substituted aryl, an optionally substituted heteroaryl, or an optionally substituted hetereocyclic.

In certain embodiments, B has the structure:

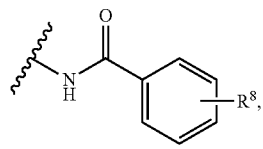

Formula III

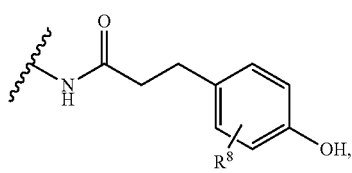

Formula IV

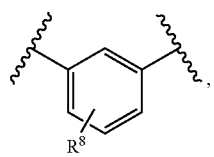

Formula V

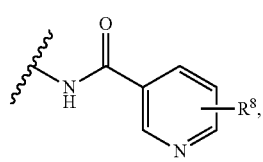

Formula VI wherein $R^8$ is a radionuclide, wherein the radionuclide is $^{18}$F, $^{75}$Br, $^{76}$Br, $^{77}$Br, $^{123}$I, $^{124}$I, $^{125}$I, $^{131}$I, or $^{211}$At.

In some embodiments, B has the structure:

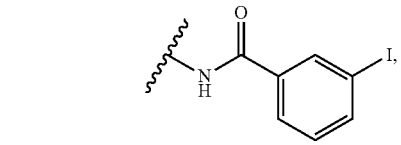

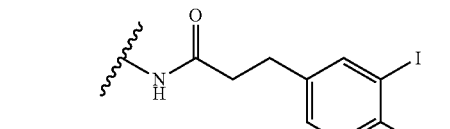

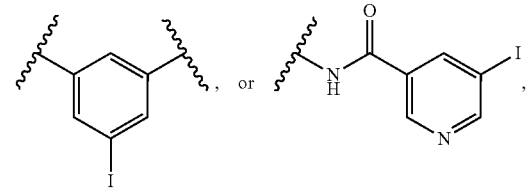

wherein the iodine atom is $^{123}$I, $^{124}$I, $^{125}$I, or $^{131}$I.

In other embodiments, B has the structure of:

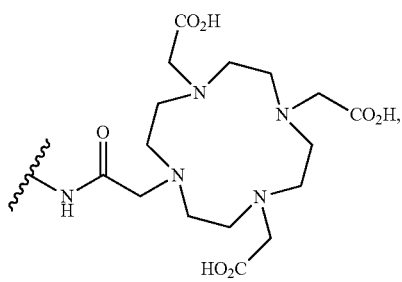 [SMILES: *NC(=O)CN1CCN(CC(=O)O)CCN(CC(=O)O)CCN(CC(=O)O)CC1]

wherein a metal is chelated to the structure.

In some embodiments, $L^4$ is optionally substituted C1-C6 alkyl (e.g., n-butyl) or absent.

In certain embodiments, $R^5$ is $L^4$-B and $R^6$ and $R^7$ are both hydrogen.

In other embodiments, $R^6$ is $L^4$-B and $R^5$ and $R^7$ are both hydrogen.

In some embodiments, $L^2$ is $L^4$-B, $R^5$ and $R^7$ are hydrogen, and $R^6$ is optionally substituted C1-C6 heteroalkyl (e.g.,

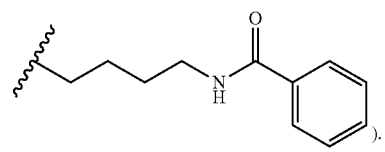 [SMILES: *CCCCNC(=O)c1ccccc1]

).

In certain embodiments, $L^2$ is selected from optionally substituted C1-C6 alkyl (e.g., n-butyl), optionally substituted C1-C6 heteroalkyl (e.g.,

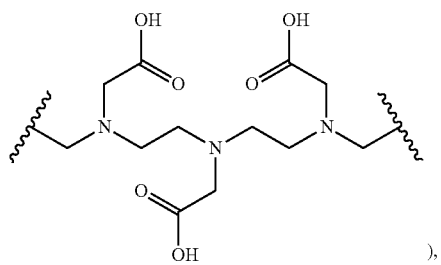 [SMILES: *CN(CCN(CCN(C*)CC(=O)O)CC(=O)O)CC(=O)O]

), optionally substituted C3-C10 cycloalkyl (e.g., cyclohexyl), optionally substituted aryl (e.g., phenyl), and optionally substituted C2-C100 polyethylene glycol (e.g.,

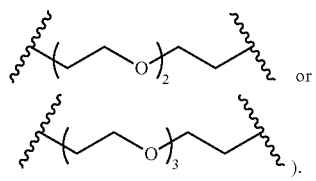

).

In other embodiments, $L^1$ is absent or optionally substituted C3-C10 cycloalkyl.

In some embodiments, $L^1$ is absent and m is 0.

In certain embodiments, $L^1$ is optionally substituted C3-C10 cycloalkyl (e.g., cyclohexyl) and m is 1.

In some embodiments, $L^3$ is absent.

In some embodiments, $L^3$ is optionally substituted C1-C6 alkyl (e.g., methylene).

In other embodiments, $R^1$ is hydrogen.

In some embodiments, $R^2$ is —CH$_2$CO$_2$H or —CH$_2$CH$_2$CO$_2$H.

In certain embodiments, $R^1$ is —CH$_2$CO$_2$H.

In some embodiments, $R^3$ and $R^4$ combine to form C=O or $R^3$ and $R^4$ are both hydrogen.

In certain embodiments, n is 0.

In other embodiments, n is 1.

In some embodiments, $R^9$ is —CO$_2$H,

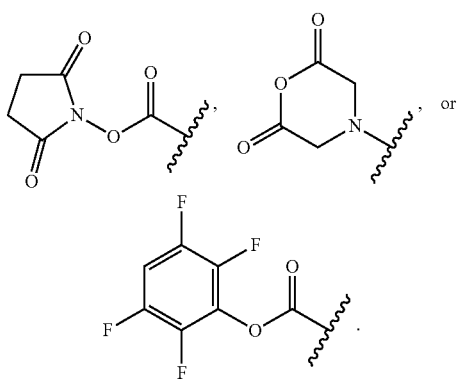

In certain embodiments, o is 3.

In other embodiments, the polypeptide is an antibody, or an antigen-binding fragment thereof.

In some embodiments, the antibody, or antigen-binding fragment thereof, specifically binds insulin-like growth factor-1 receptor (IGF1R).

In other embodiments, the antibody, or antibody-binding fragment thereof includes a heavy chain variable domain including at least one, two, or all three complementarity determining regions (CDRs) selected from:

(a) CDR-H1 including the amino acid sequence of SEQ ID NO: 1;
(b) CDR-H2 including the amino acid sequence of SEQ ID NO: 2; and
(c) CDR-H3 including the amino acid sequence of SEQ ID NO: 3.

In some embodiments, the antibody, or antibody-binding fragment thereof includes a light chain variable domain including at least one, two, or all three CDRs selected from:

(a) CDR-L1 including the amino acid sequence of SEQ ID NO: 1;
(b) CDR-L2 including the amino acid sequence of SEQ ID NO: 3; and
(c) CDR-L3 including the amino acid sequence of SEQ ID NO: 3.

In certain embodiments, the antibody, or antibody-binding fragment thereof includes a heavy chain variable domain and a light chain variable domain including at least one, two, three, four, five, or all six CDRs selected from:

(a) CDR-H1 including the amino acid sequence of SEQ ID NO: 1;
(b) CDR-H2 including the amino acid sequence of SEQ ID NO: 2;
(c) CDR-H3 including the amino acid sequence of SEQ ID NO: 3;
(d) CDR-L1 including the amino acid sequence of SEQ ID NO: 4;

(e) CDR-L2 including the amino acid sequence of SEQ ID NO: 5; and (f) CDR-L3 including the amino acid sequence of SEQ ID NO: 6.

In other embodiments, the heavy chain variable domain includes the amino acid sequence of SEQ ID NO: 7.

In some embodiments, the light chain variable domain includes the amino acid sequence of SEQ ID NO: 8.

In certain embodiments, the antibody, or antigen-binding fragment thereof, includes a heavy chain including the amino acid sequence of SEQ ID NO: 9.

In other embodiments, the antibody, or antigen-binding fragment thereof, includes a light chain including the amino acid sequence of SEQ ID NO: 10.

In some embodiments, the antibody, or antigen-binding fragment thereof is figitumumab, cixutumumab, AMG479, BIBB022, SCH717454, or R1507.

In certain embodiments, the antibody, or antibody-binding fragment thereof, substantially binds to the same epitope as figitumumab.

In certain embodiments, the conjugate has the structure:

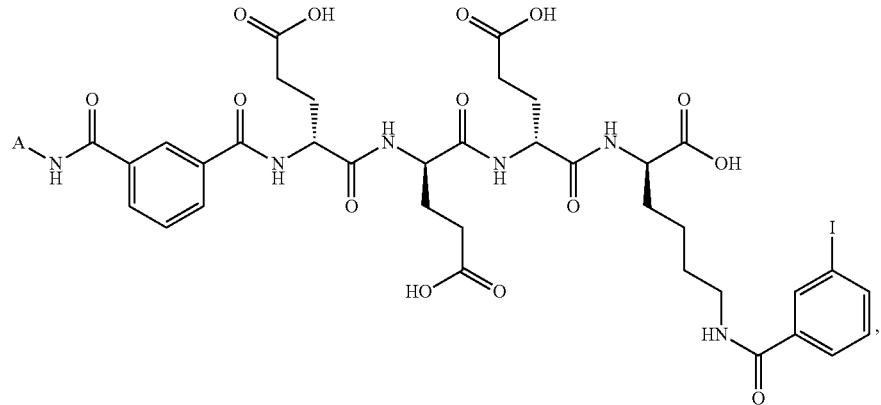

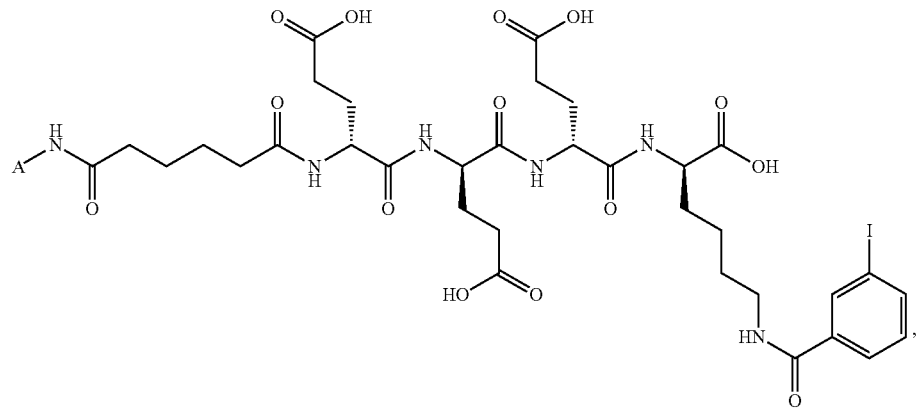

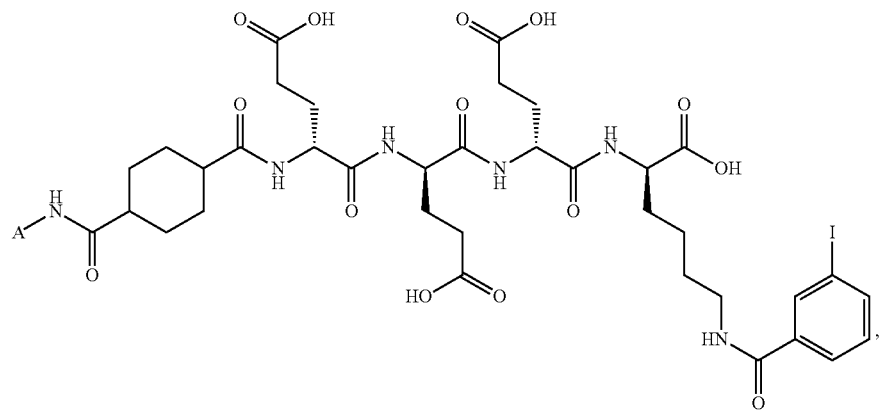

-continued
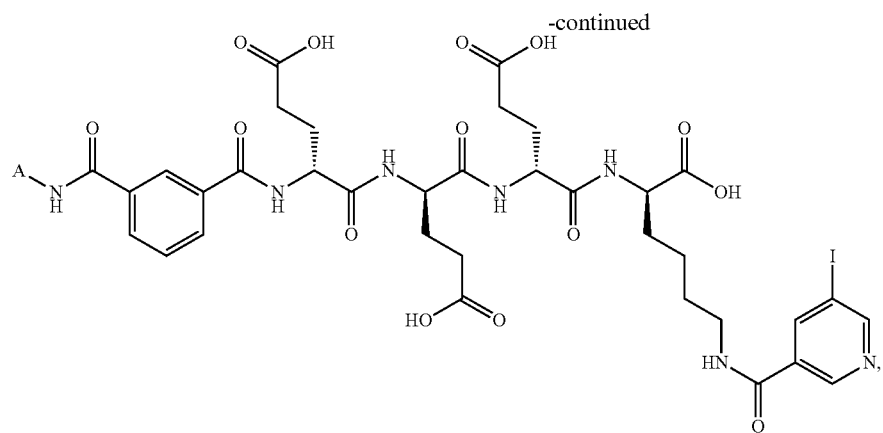
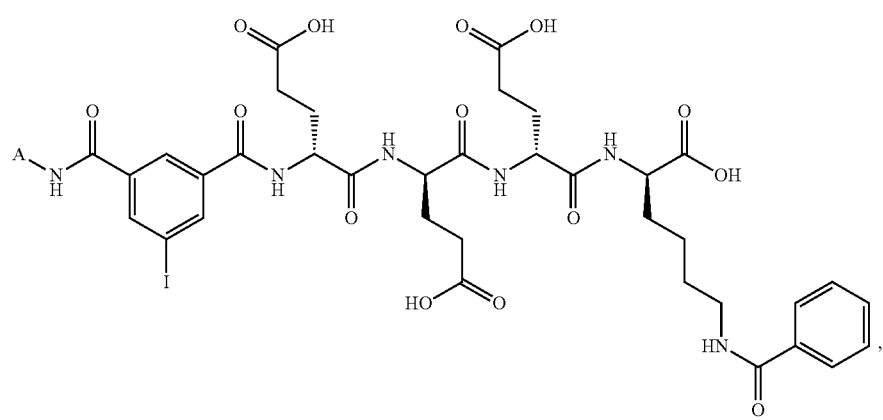
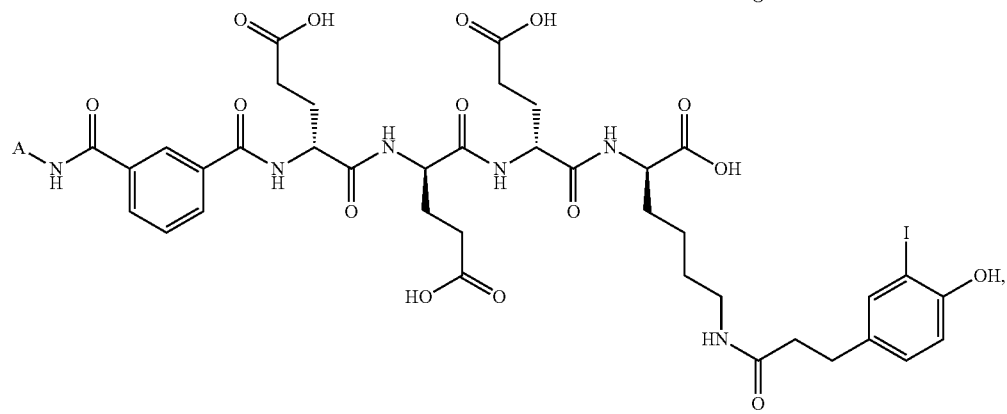
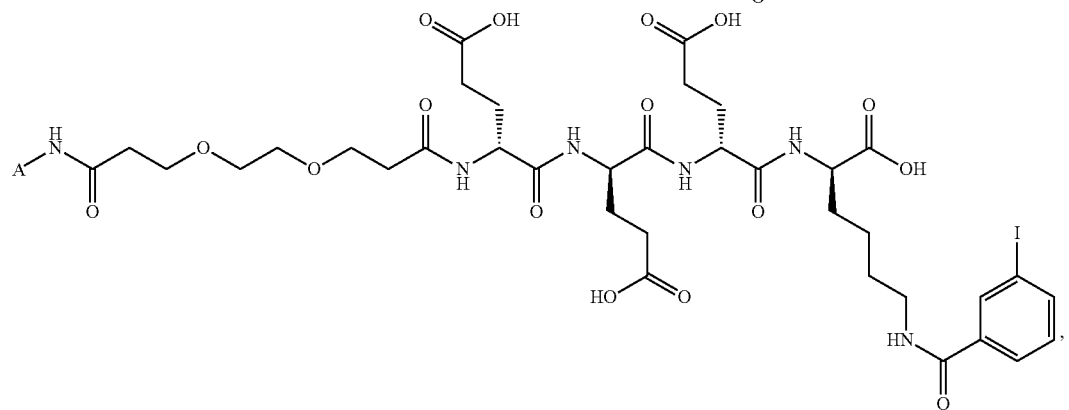

-continued
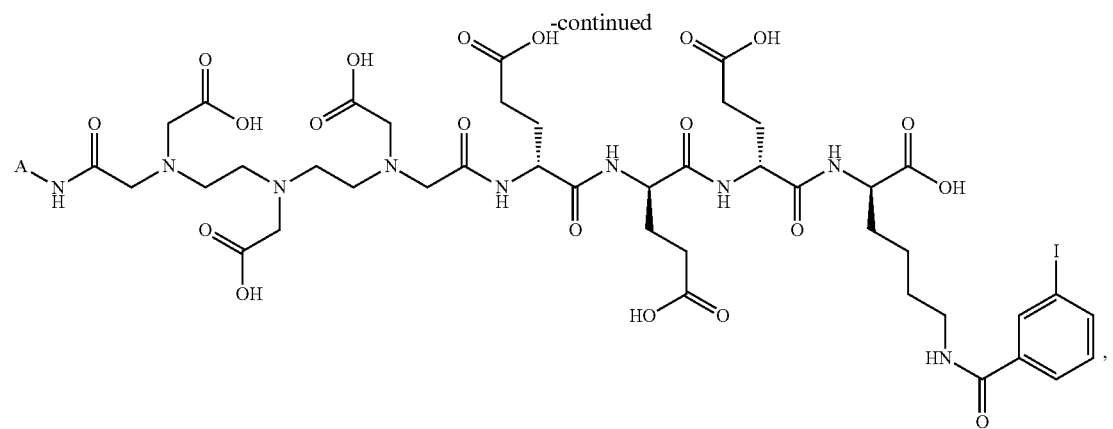
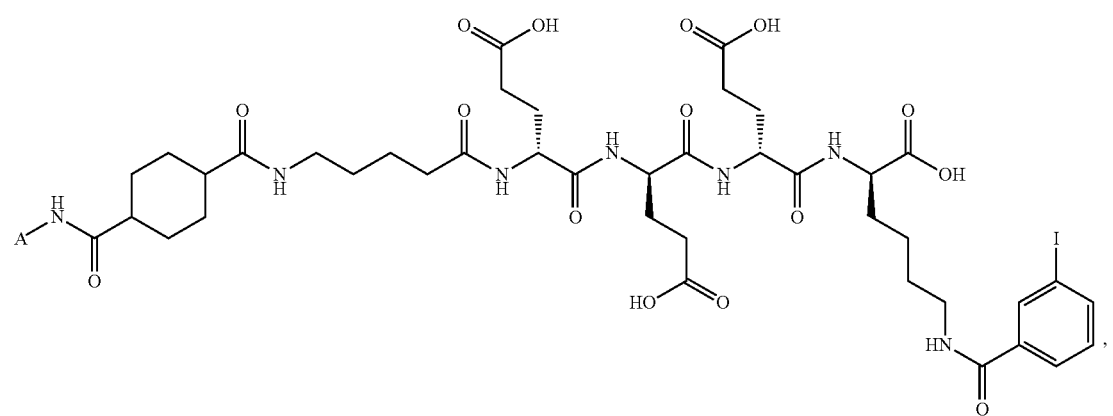
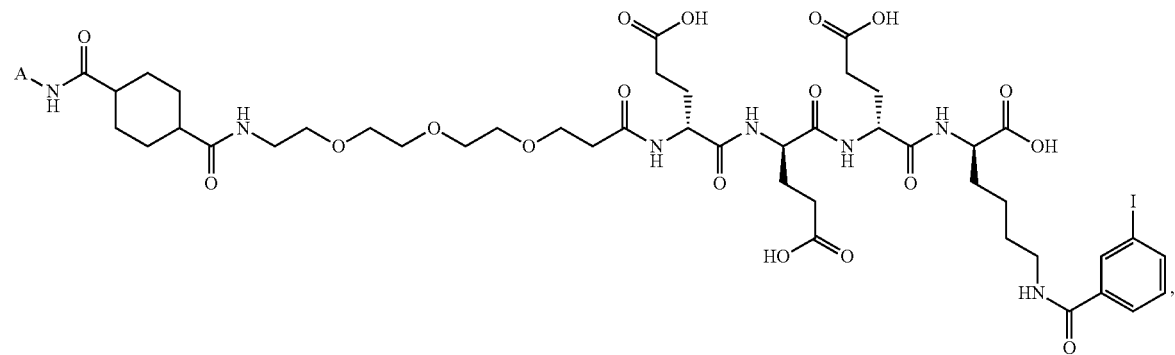
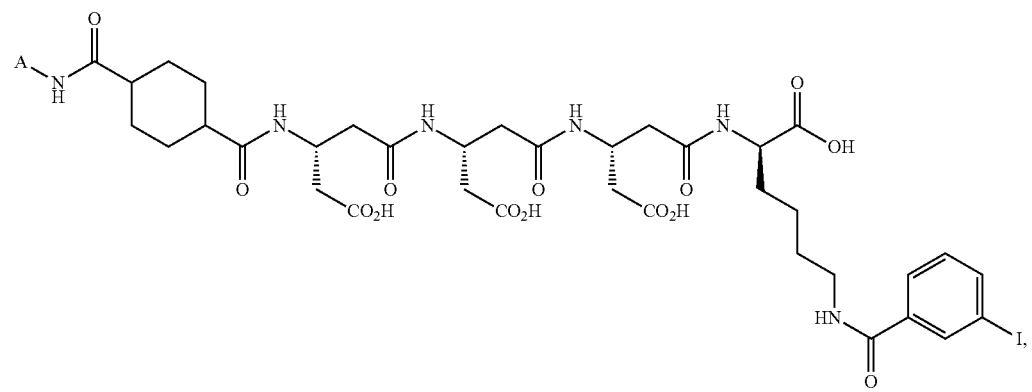

-continued
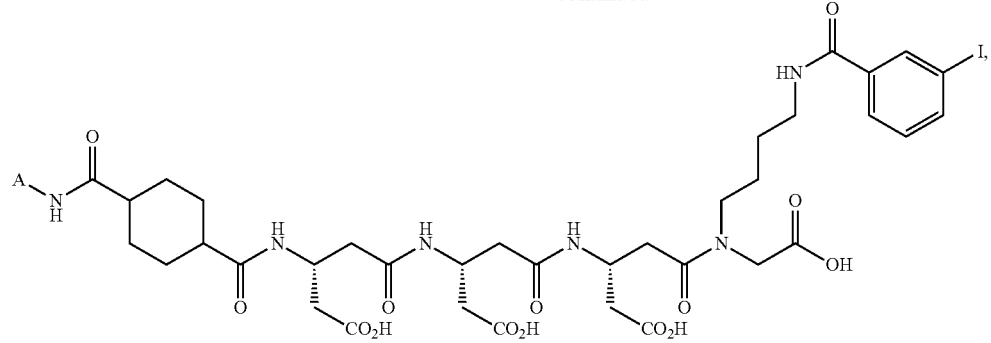
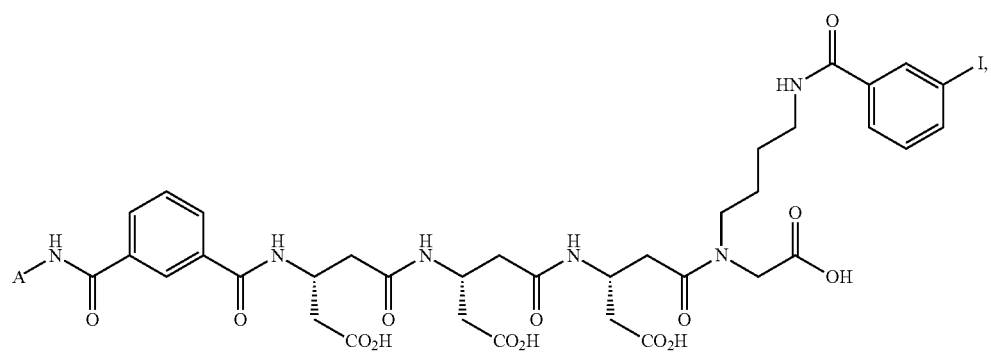
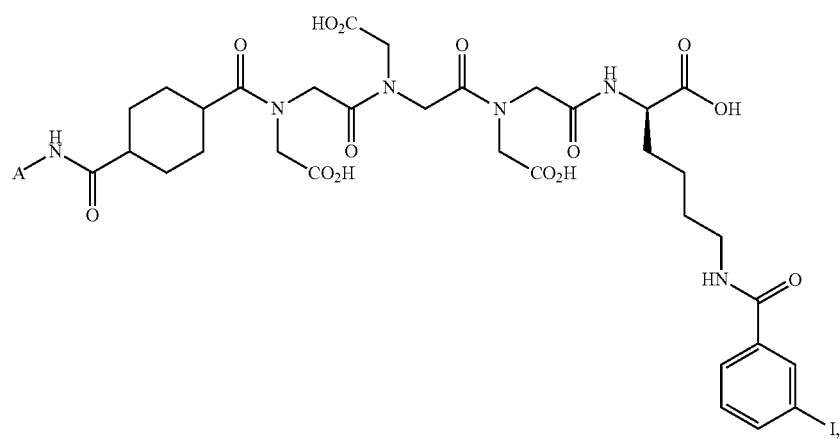
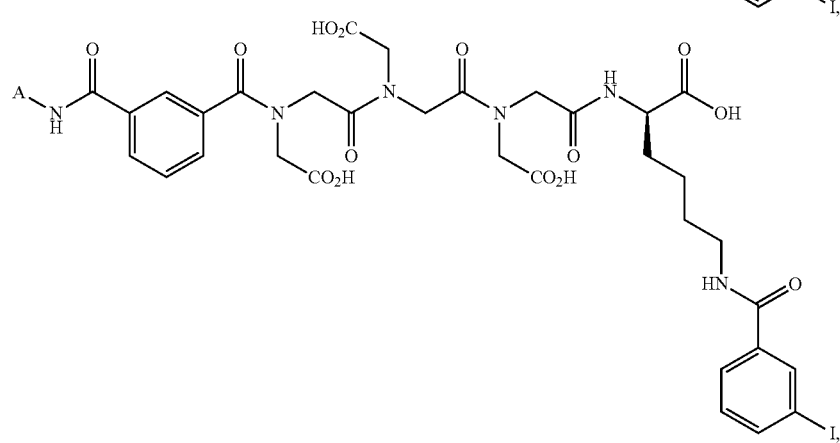

-continued
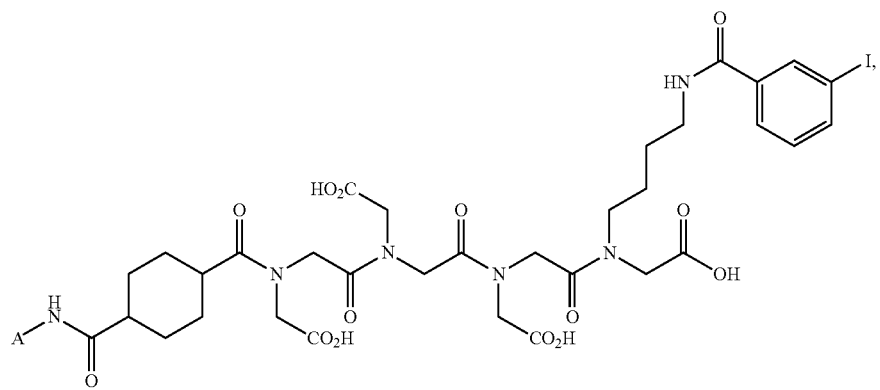
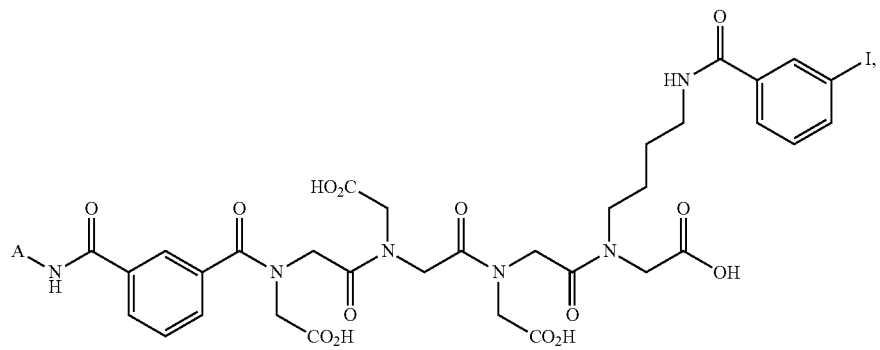
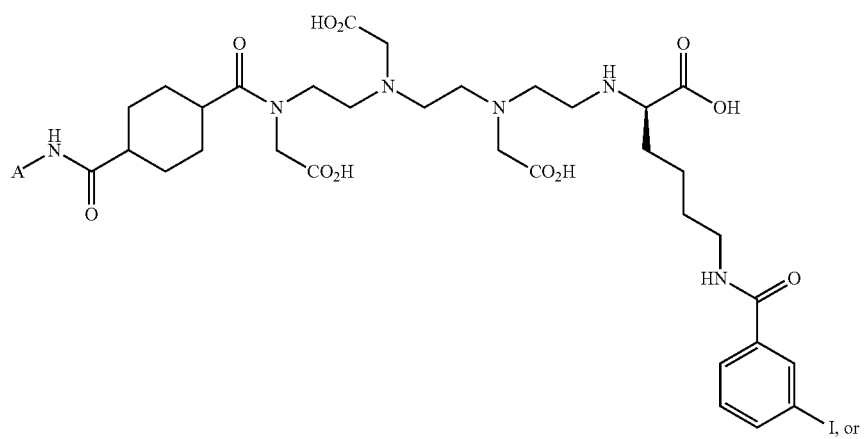
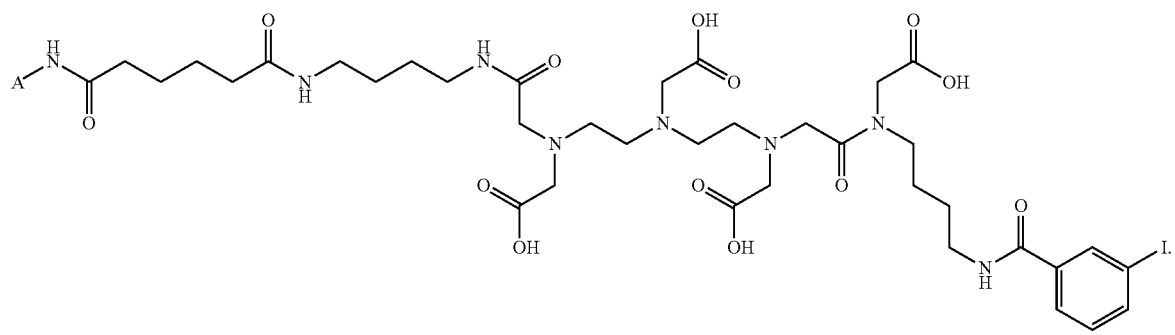

wherein the iodine atom is $^{123}$I, $^{124}$I, $^{125}$I, or $^{131}$I.
In other embodiments, the conjugate has the structure:
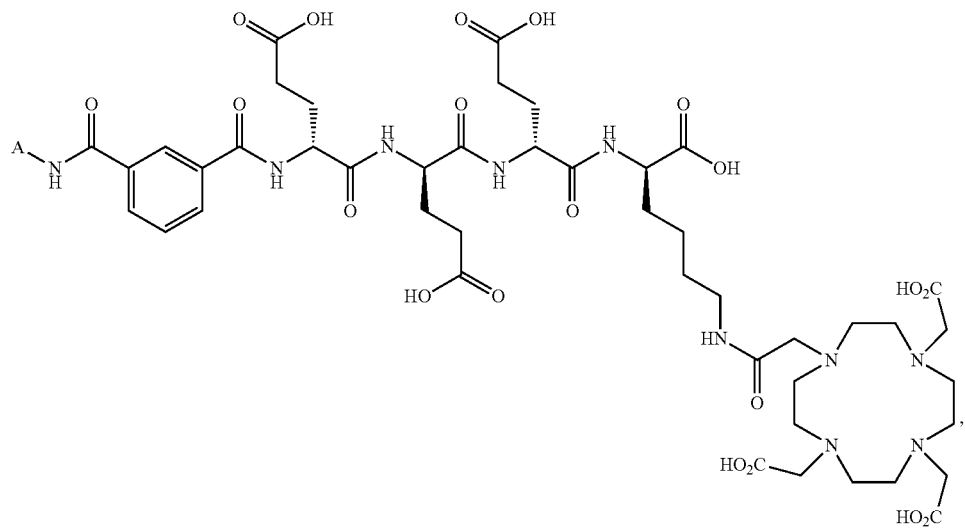
wherein a metal is chelated to the structure.
In certain embodiments, the compound of Formula II has the structure:
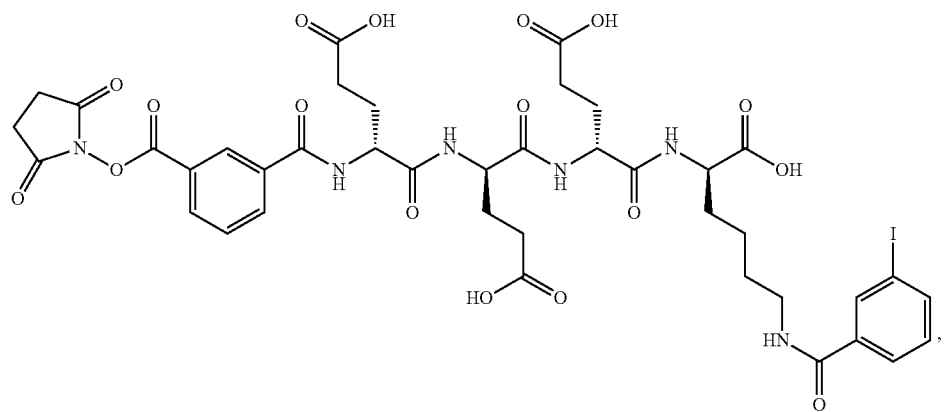
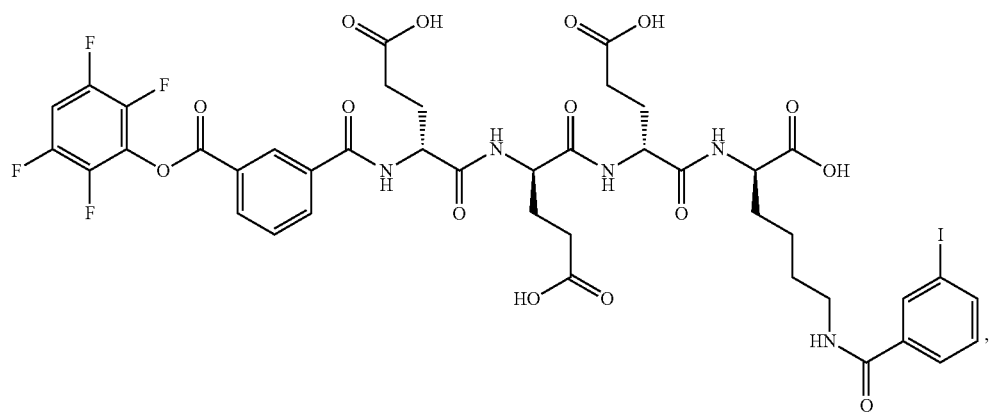

-continued
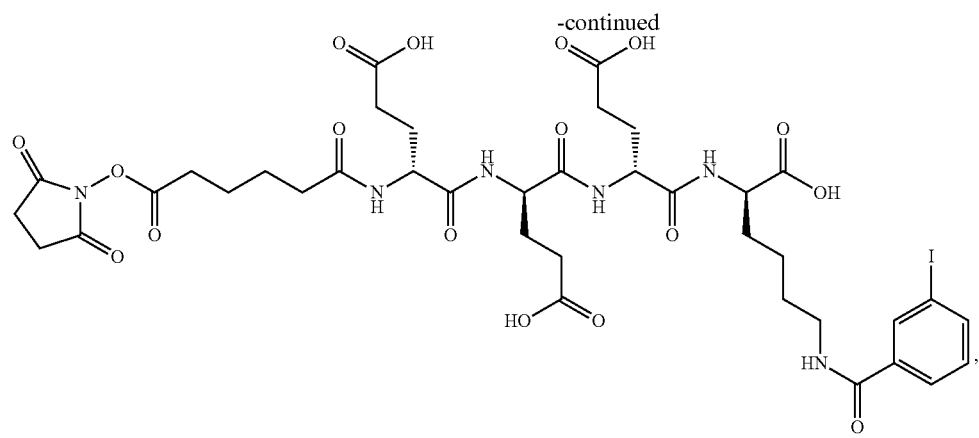
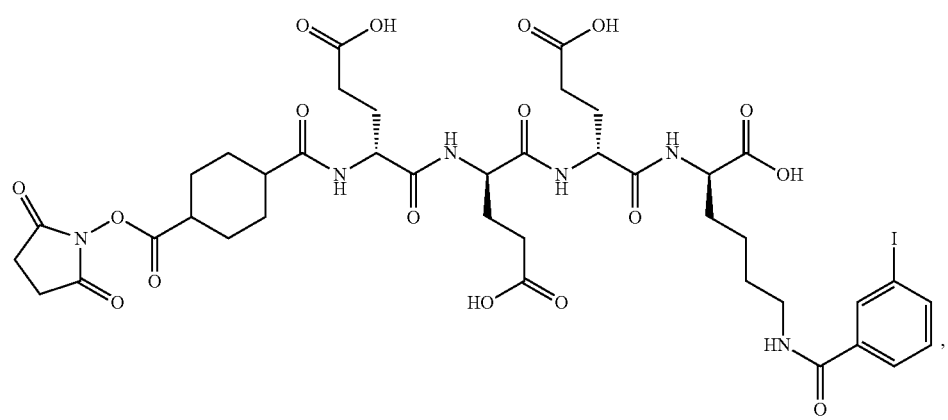
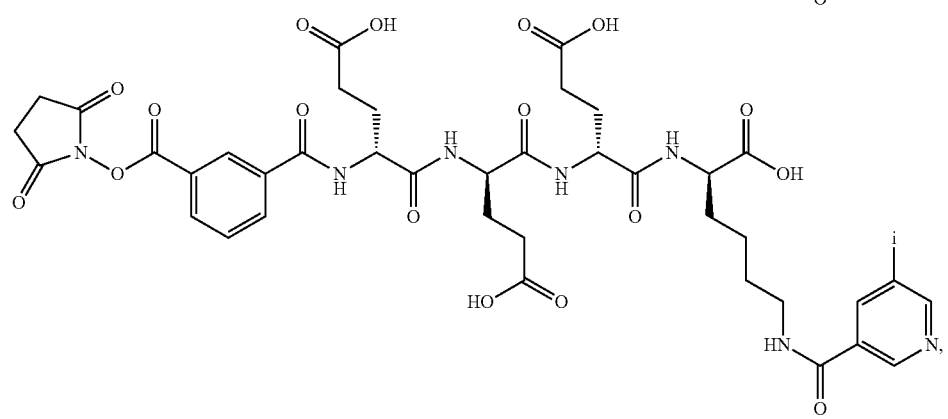
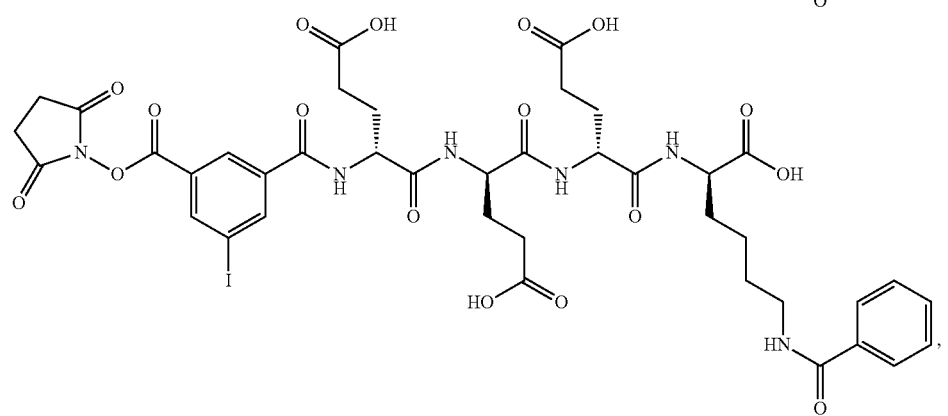

-continued
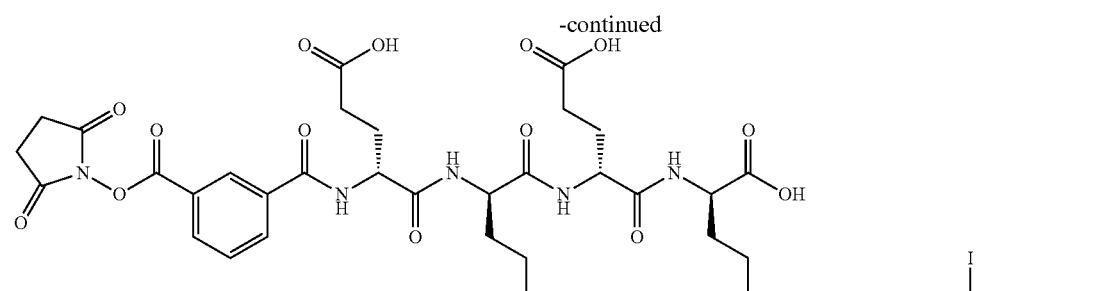
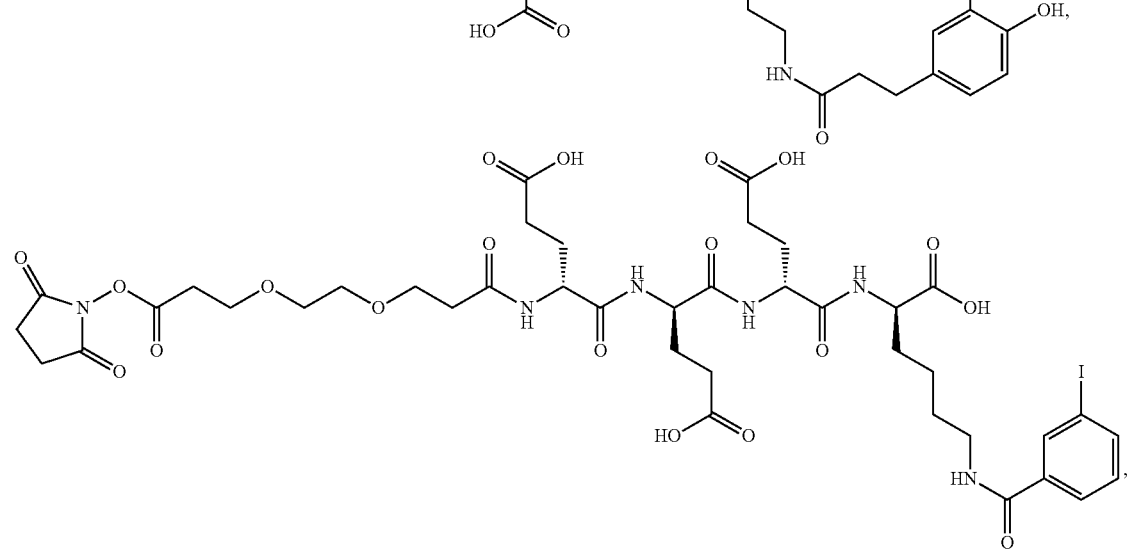
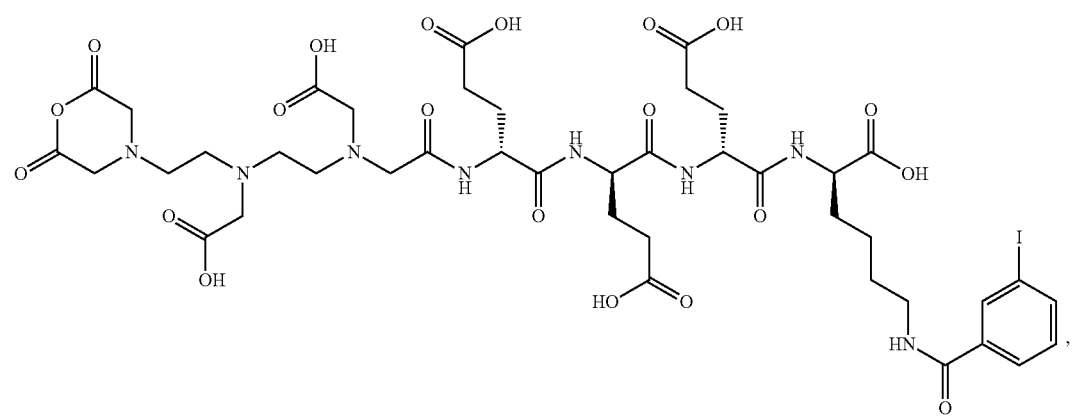
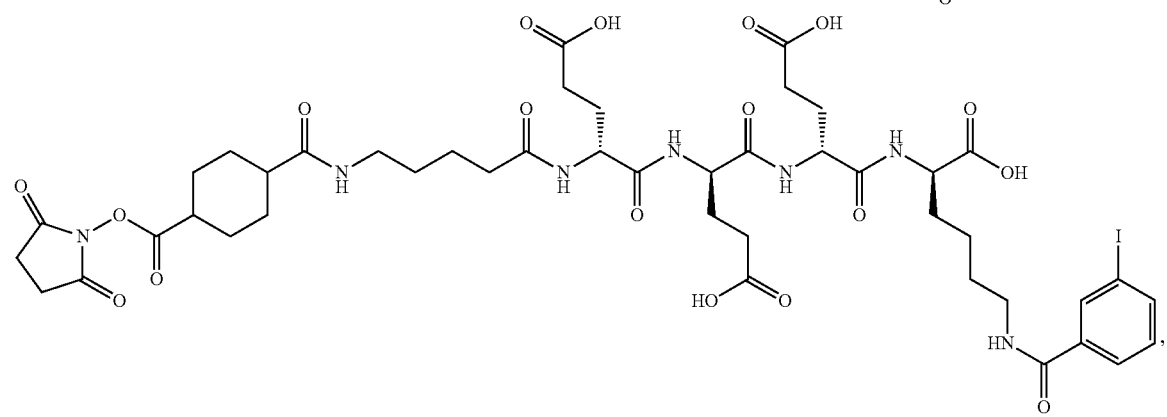

25
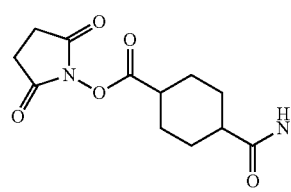
26
-continued
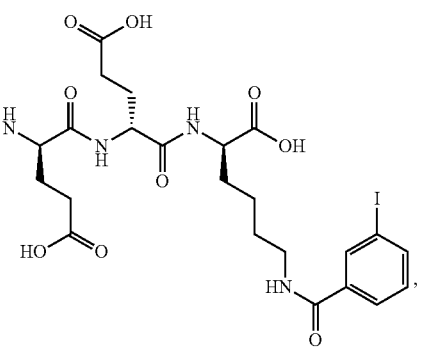
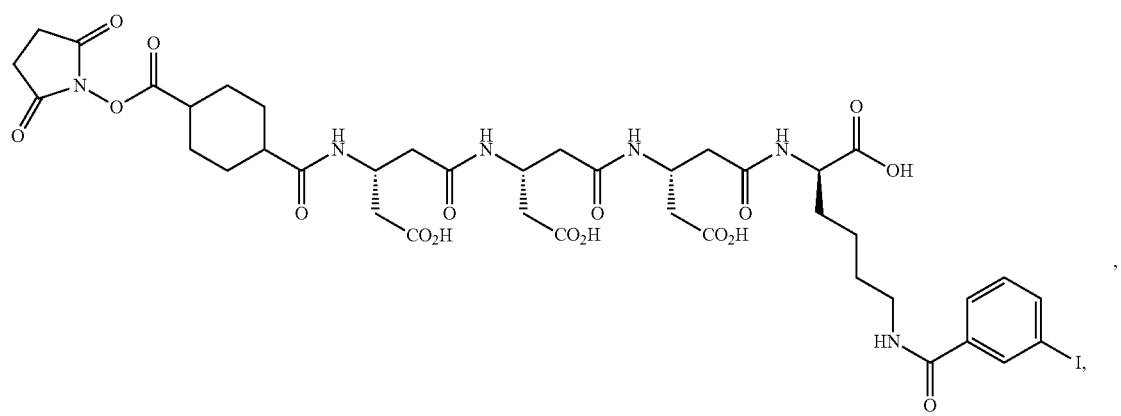
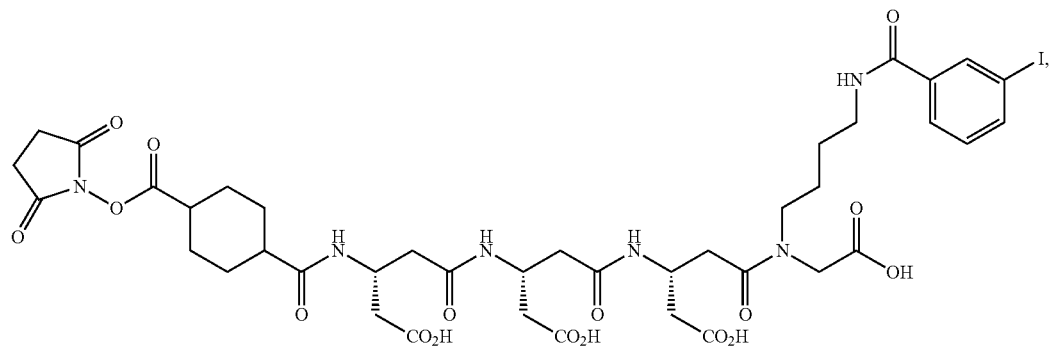
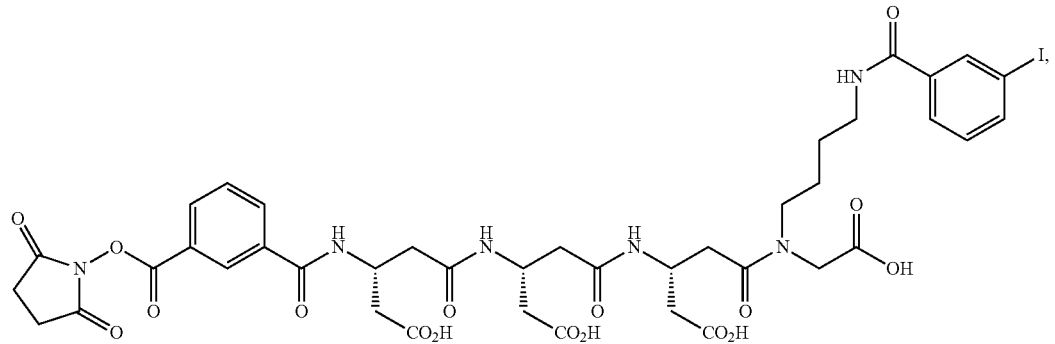

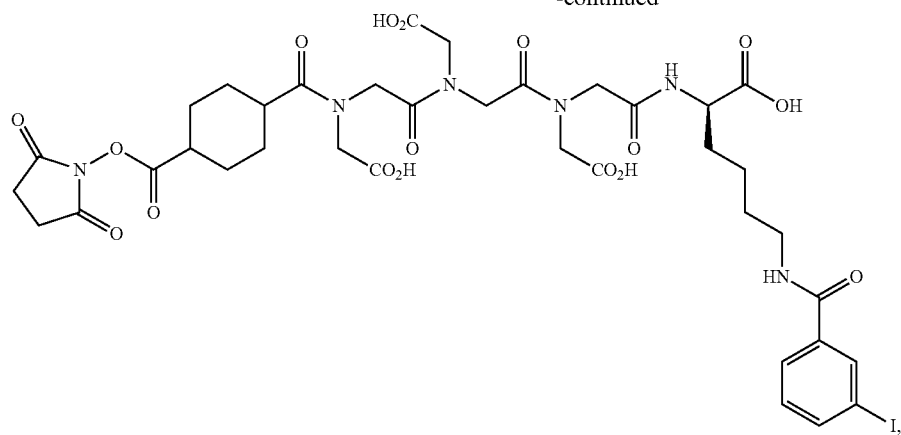
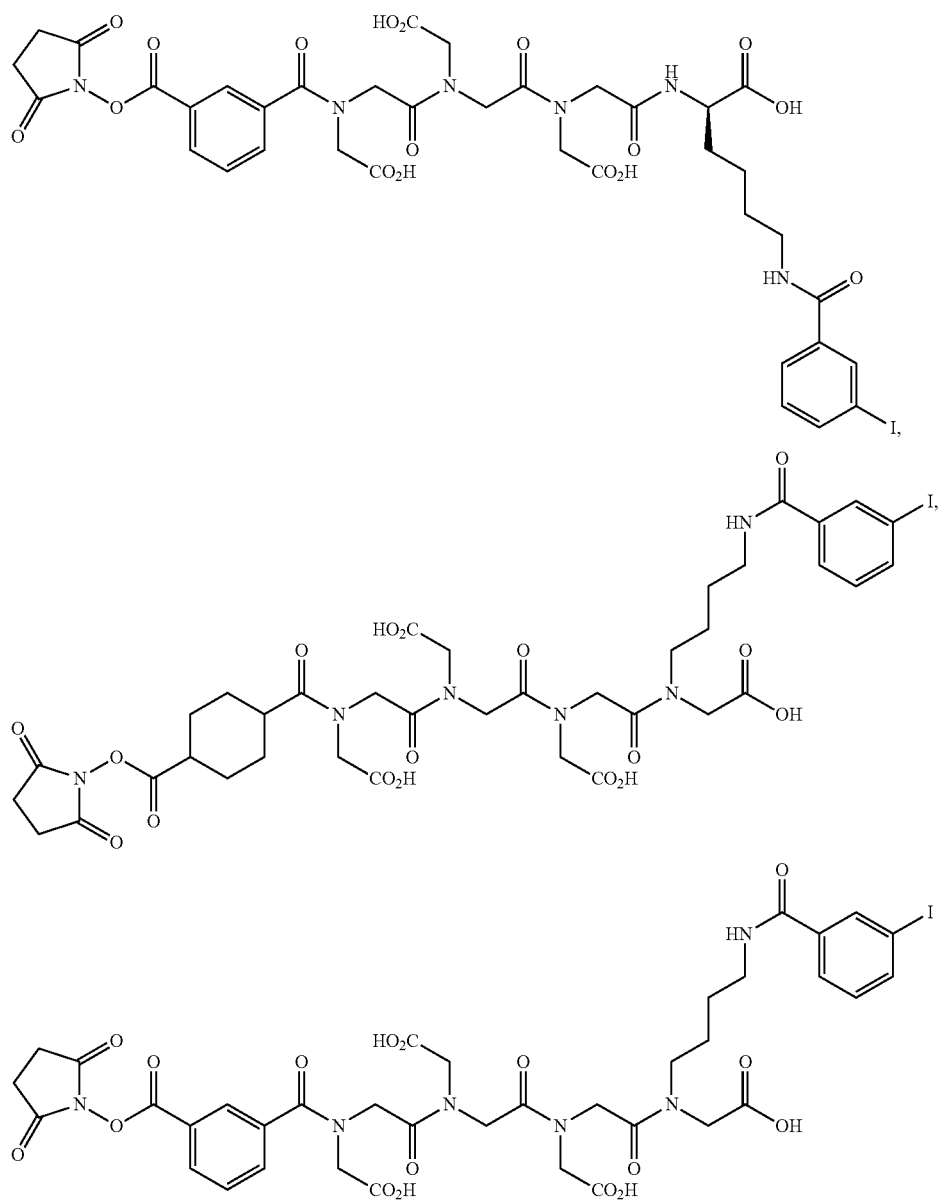

-continued

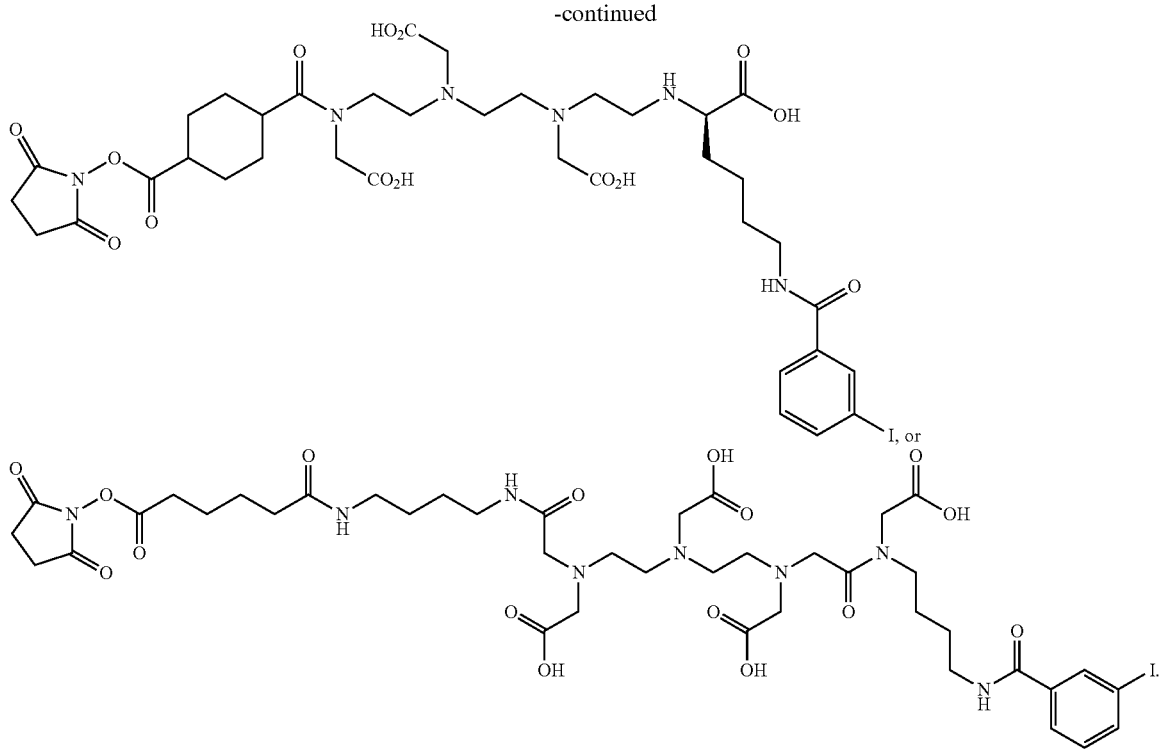

wherein the iodine atom is $^{123}$I, $^{124}$I, $^{125}$I, or $^{131}$I.

In other embodiments, the compound of Formula II has the structure:

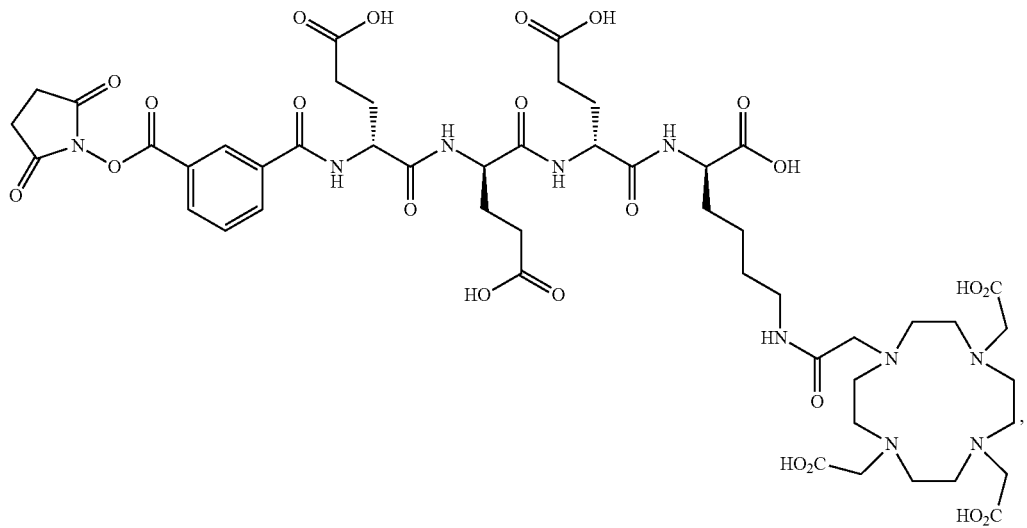 [SMILES: O=C(O)CC[C@@H](NC(=O)c1cccc(C(=O)ON2C(=O)CCC2=O)c1)C(=O)N[C@H](CCC(=O)O)C(=O)N[C@H](CCC(=O)O)C(=O)N[C@H](CCCCNC(=O)CN1CCN(CC(=O)O)CCN(CC(=O)O)CCN(CC(=O)O)CC1)C(=O)O]

wherein a metal is chelated to the structure.

In another aspect, the invention features a pharmaceutical composition including any of the foregoing conjugates and a pharmaceutically acceptable excipient.

In another aspect, the invention features a method of treating cancer, the method including administering to a subject in need thereof any of the foregoing conjugates or pharmaceutical compositions.

In another aspect, the invention features a method of radiation treatment planning, the method including administering to a subject in need thereof any of the foregoing conjugates or pharmaceutical compositions.

In another aspect, the invention features a method of treating cancer, the method including administering to a subject in need thereof a first dose of any of the foregoing conjugates or pharmaceutical compositions in an amount effective for radiation treatment planning, followed by administering a second dose of any of the foregoing conjugates or pharmaceutical compositions in a therapeutically effective amount.

In certain embodiments, the conjugate or composition administered in the first dose and the conjugate or composition administered in the second dose are the same.

In other embodiments, the conjugate or composition administered in the first dose and the conjugate or composition administered in the second dose are different.

In some embodiments, the cancer is a solid tumor cancer (e.g., breast cancer, non-small cell lung cancer, prostate cancer, pancreatic cancer, head and neck cancer, colon cancer, sarcoma, or adrenocortical carcinoma).

In certain embodiments, the method further includes administering an antiproliferative.

In some embodiments, any of the foregoing conjugates or compositions and the antiproliferative are administered within 28 days (e.g., within 14, 7, 6, 5, 4, 3, 2, or 1 day(s)) of each other.

Chemical Terms:

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —$NH_2$) or a substituted amino (i.e., —$N(R^{N1})_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —$CO_2R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —$C(O)NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —$SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —$C(O)R^{D'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR^{H'}C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}C(O)OR^{K'}$, wherein $R^{J'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, Or $C_{2-20}$ alkylene). In some embodiments, the alkylene can be further substituted with 1, 2, 3, or 4 substituent groups as defined herein for an alkyl group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "amino," as used herein, represents —N($R^{N1}$)$_2$, wherein each $R^{N1}$ is, independently, H, OH, NO$_2$, N($R^{N2}$)$_2$, SO$_2$O$R^{N2}$, SO$_2R^{N2}$, SO$R^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., —NH$_2$) or a substituted amino (i.e., —N($R^{N1}$)$_2$). In a preferred embodiment, amino is —NH$_2$ or —NH$R^{N1}$, wherein $R^{N1}$ is, independently, OH, NO$_2$, NH$_2$, N$R^{N2}$$_2$, SO$_2$O$R^{N2}$, SO$_2R^{N2}$, SO$R^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, C$_{1-20}$ alkyl (e.g., C$_{1-6}$ alkyl), or C$_{6-10}$ aryl.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) C$_{1-6}$ alkoxy; (2) C$_{1-6}$ alkylsulfinyl; (3) amino, as defined herein (e.g., unsubstituted amino (i.e., —NH$_2$) or a substituted amino (i.e., —N($R^{N1}$)$_2$, where $R^{N1}$ is as defined for amino); (4) C$_{6-10}$ aryl-C$_{1-6}$ alkoxy; (5) azido; (6) halo; (7) (C$_{2-9}$ heterocyclyl)oxy; (8) hydroxy; (9) nitro; (10) oxo (e.g., carboxyaldehyde or acyl); (11) C$_{1-7}$ spirocyclyl; (12) thioalkoxy; (13) thiol; (14) —CO$_2R^{A'}$, where $R^{A'}$ is selected from the group consisting of (a) C$_{1-20}$ alkyl (e.g., C$_{1-6}$ alkyl), (b) C$_{2-20}$ alkenyl (e.g., C$_{2-6}$ alkenyl), (c) C$_{6-10}$ aryl, (d) hydrogen, (e) C$_{1-6}$ alk-C$_{6-10}$ aryl, (f) amino-C$_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C$_{1-6}$ alkyl; (15) —C(O)NR$^{B'}$R$^{C'}$, where each of R$^{B'}$ and R$^{C'}$ is, independently, selected from the group consisting of (a) hydrogen, (b) C$_{1-6}$ alkyl, (c) C$_{6-10}$ aryl, and (d) C$_{1-6}$ alk-C$_{6-10}$ aryl; (16) —SO$_2R^{D'}$, where R$^{D'}$ is selected from the group consisting of (a) C$_{1-6}$ alkyl, (b) C$_{6-10}$ aryl, (c) C$_{1-6}$ alk-C$_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) C$_{1-6}$ alkyl, (c) C$_{6-10}$ aryl and (d) C$_{1-6}$ alk-C$_{6-10}$ aryl; (18) —C(O)R$^{G'}$, where R$^{G'}$ is selected from the group consisting of (a) C$_{1-20}$ alkyl (e.g., C$_{1-6}$ alkyl), (b) C$_{2-20}$ alkenyl (e.g., C$_{2-6}$ alkenyl), (c) C$_{6-10}$ aryl, (d) hydrogen, (e) C$_{1-6}$ alk-C$_{6-10}$ aryl, (f) amino-C$_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C$_{1-6}$ alkyl; (19) —NR$^{H'}$C(O)R$^1$, wherein R$^{H'}$ is selected from the group consisting of (a1) hydrogen and (b1) C$_{1-6}$ alkyl, and R$^1$ is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{1-6}$ alk-C$_{6-10}$ aryl, (f2) amino-C$_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C$_{1-6}$ alkyl; (20) —NR$^{J'}$C(O)OR$^{K'}$, where R$^{J'}$ is selected from the group consisting of (a1) hydrogen and (b1) C$_{1-6}$ alkyl, and R$^{K'}$ is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{1-6}$ alk-C$_{6-10}$ aryl, (f2) amino-C$_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) aminopolyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) $-(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) $-(CH_2)_qCONR^{B'}R^{C'}$, where q is an integer from zero to four and where $R^{B'}$ and $R^{D'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) $-(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) $-(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "arylalkyl," as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "carbonyl," as used herein, represents a C(O) group, which can also be represented as C=O.

The term "carboxy," as used herein, means $-CO_2H$.

The term "cyano," as used herein, represents an $-CN$ group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond or one carbon-carbon triple bond, the cycloalkyl group can be referred to as a "cycloalkenyl" or "cycloalkynyl" group respectively. Exemplary cycloalkenyl and cycloalkynyl groups include cyclopentenyl, cyclohexenyl, cyclohexynyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) $-(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) $-(CH_2)_qCONR^{B'}R^{C'}$, where q is an integer from zero to four and where $R^{B'}$ and $R^{D'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) $-(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) $-(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "diastereomer," as used herein means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halogen," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclys include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

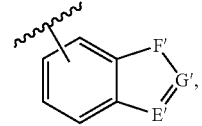

where

E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8)

azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_q$CONR$^{B'}$R$^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{1-6}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl) imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "hydrocarbon," as used herein, represents a group consisting only of carbon and hydrogen atoms.

The term "hydroxyl," as used herein, represents an —OH group. In some embodiments, the hydroxyl group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," $3^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methylphenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; and oxazoline groups.

The term "oxo" as used herein, represents =O.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —S(O)$_2$— group.

The term "thiol," as used herein represents an —SH group.

DEFINITIONS

As used herein, the term "administered in combination" or "combined administration" means that two or more agents are administered to a subject at the same time or within an interval such that there may be an overlap of an effect of each agent on the patient. In some embodiments, they are administered within 28 days (e.g., with 14, 7, 6, 5, 4, 3, 2, or 1 day(s), within 24 hours (e.g., 12, 6, 5, 4, 3, 2, or 1 hour(s), or within about 60, 30, 15, 10, 5, or 1 minute of one another. In some embodiments, the administrations of the agents are spaced sufficiently closely together such that a combinatorial (e.g., a synergistic) effect is achieved.

As used herein, "antibody" refers to a polypeptide whose amino acid sequence including immunoglobulins and fragments thereof which specifically bind to a designated antigen, or fragments thereof. Antibodies in accordance with the present invention may be of any type (e.g., IgA, IgD, IgE, IgG, or IgM) or subtype (e.g., IgA1, IgA2, IgG1, IgG2, IgG3, or IgG4). Those of ordinary skill in the art will appreciate that a characteristic sequence or portion of an antibody may include amino acids found in one or more regions of an antibody (e.g., variable region, hypervariable region, constant region, heavy chain, light chain, and combinations thereof). Moreover, those of ordinary skill in the art will appreciate that a characteristic sequence or portion of an antibody may include one or more polypeptide chains, and may include sequence elements found in the same polypeptide chain or in different polypeptide chains.

As used herein, "antigen-binding fragment" refers to a portion of an antibody that retains the binding characteristics of the parent antibody.

The term "cancer" refers to any cancer caused by the proliferation of malignant neoplastic cells, such as tumors, neoplasms, carcinomas, sarcomas, leukimia's, and lymphomas. A "solid tumor cancer" is a cancer comprising an abnormal mass of tissue, e.g., sarcomas, carcinomas, and lymphomas.

As used herein, the term "compound," is meant to include all stereoisomers, geometric isomers, and tautomers of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H—, 2H- and 4H-1,2,4-triazole, 1H- and 2H-isoindole, and 1H- and 2H-pyrazole. Tautomeric forms can be in equilibrium or sterically locked into one form by appropriate substitution.

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

As used herein "detection agent" refers to a molecule or atom which is useful in diagnosing a disease by locating the cells containing the antigen. Various methods of labeling polypeptides with detection agents are known in the art. Examples of detection agents include, but are not limited to, radioisotopes and radionuclides (e.g., $^3$H, $^{14}$C, $^{15}$N, $^{18}$F, $^{35}$S, $^{64}$Cu, $^{67}$Cu, $^{75}$Br, $^{76}$Br, $^{77}$Br, $^{89}$Zr, $^{90}$Y, $^{97}$Ru, $^{99}$Tc, $^{105}$Rh, $^{109}$Pd, $^{111}$In, $^{123}$I, $^{124}$I, $^{125}$I, $^{131}$I, $^{149}$Pm, $^{153}$Sm, $^{166}$Ho, $^{177}$Lu, $^{186}$Re, $^{188}$Re, $^{198}$Au, $^{199}$Au, $^{203}$Pb, $^{211}$At, $^{212}$Pb, $^{212}$Bi, $^{213}$Bi, $^{223}$Ra, $^{225}$Ac, $^{227}$Th, $^{229}$Th), dyes (such as with the biotin-streptavidin complex), contrast agents, luminescent agents (e.g., FITC, rhodamine, lanthanide phosphors, cyanine, and near IR dyes), and magnetic agents, such as gadolinium chelates.

The term an "effective amount" of an agent (e.g., any of the foregoing conjugates), as used herein, is that amount sufficient to effect beneficial or desired results, such as clinical results, and, as such, an "effective amount" depends upon the context in which it is being applied.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: ascorbic acid, histidine, phosphate buffer, butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as use herein, represents those salts of the compounds described here that are, within the scope of sound medical judgment, suitable for use in contact with the tissues of humans and animals without undue toxicity, irritation, or allergic response. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, among others. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "polypeptide" as used herein refers to a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides can include one or more "non-natural" amino acids or other entities that nonetheless are capable of integrating into a polypeptide chain. In some embodiments, a polypeptide may be glycosylated, e.g., a polypeptide may contain one or more covalently linked sugar moieties. In some embodiments, a single "polypeptide" (e.g., an antibody polypeptide) may comprise two or more individual polypeptide chains, which may in some cases be linked to one another, for example by one or more disulfide bonds or other means.

By "subject" is meant a human or non-human animal (e.g., a mammal).

By "substantial identity" or "substantially identical" is meant a polypeptide sequence that has the same polypeptide sequence, respectively, as a reference sequence, or has a specified percentage of amino acid residues, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

As used herein, and as well understood in the art, "to treat" a condition or "treatment" of the condition (e.g., the conditions described herein such as cancer) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

BRIEF DESCRIPTION OF THE DRAWINGS

FIG. 3 is the amino acid sequence of the CDRs of figitumumab.

FIG. 4 is the amino acid sequence of the variable domains of figitumumab.

FIG. 5 is the amino acid sequence of the heavy chain of figitumumab.

FIG. 6 is the amino acid sequence of the light chain of figitumumab.

DETAILED DESCRIPTION

Figure 1:
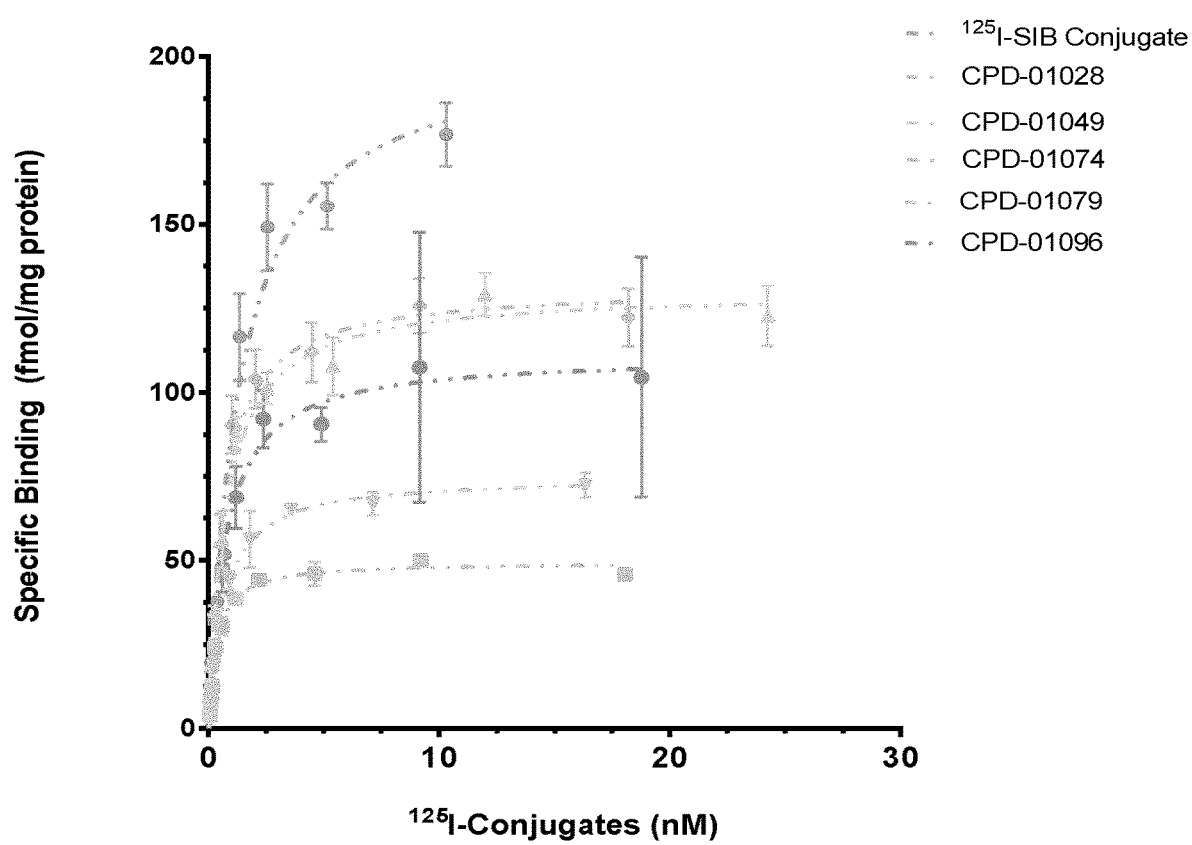
FIG. 1 is a graph illustrating binding affinities for select conjugates.

The present invention relates to linkers that enhance residualization or retention of detection agents in cells after internalization of polypeptide-linker-detection agent conjugate. Typically cell internalizing labeled polypeptides are limited by loss of the label after lysosomal processing. This leads to significant loss of signal or payload at the desired site and potential toxicity in normal tissues. To overcome this limitation a platform of residualizing linkers capable of carrying a wide variety of detection agents has been developed and demonstrated improved radioactivity retention (residualization) in target cells when linked to polypeptides.

Polypeptides

Polypeptides include, for example, any of a variety of hematologic agents (including, for instance, erythropoietin, blood-clotting factors, etc.), interferons, colony stimulating factors, antibodies, enzymes, and hormones. The identity of a particular polypeptide is not intended to limit the present disclosure, and any polypeptide of interest can be a polypeptide in the present methods.

A reference polypeptide described herein can include a target-binding domain that binds to a target of interest (e.g., binds to an antigen). For example, a polypeptide, such as an antibody, can bind to a transmembrane polypeptide (e.g., receptor) or ligand (e.g., a growth factor). Exemplary molecular targets (e.g., antigens) for polypeptides described herein (e.g., antibodies) include CD proteins such as CD2, CD3, CD4, CD8, CD11, CD19, CD20, CD22, CD25, CD33, CD34, CD40, CD52; members of the ErbB receptor family such as the EGF receptor (EGFR, HER1, ErbB1), HER2 (ErbB2), HER3 (ErbB3) or HER4 (ErbB4) receptor; macrophage receptors such as CRIg; tumor necrosis factors such as TNFα or TRAIL/Apo-2; cell adhesion molecules such as LFA-1, Mac1, p150,95, VLA-4, ICAM-1, VCAM and αvβ3 integrin including either α or β, subunits thereof (e.g., anti-CD11a, anti-CD18 or anti-CD11 b antibodies); growth factors and receptors such as EGF, FGFR (e.g., FGFR3) and VEGF; IgE; cytokines such as IL1; cytokine receptors such as IL2 receptor; blood group antigens; flk2/flt3 receptor; obesity (OB) receptor; mpl receptor; CTLA-4; protein C; neutropilins; ephrins and receptors; netrins and receptors; slit and receptors; chemokines and chemookine receptors such as CCL5, CCR4, CCR5; amyloid beta; complement factors, such as complement factor D; lipoproteins, such as oxidized LDL (oxLDL); lymphotoxins, such as lymphotoxin alpha (LTa). Other molecular targets include Tweak, B7RP-1, proprotein convertase subtilisin/kexin type 9 (PCSK9), sclerostin, c-kit, Tie-2, c-fms, and anti-M1.

Antibodies

An IgG antibody consists of two identical light polypeptide chains and two identical heavy polypeptide chains linked together by disulfide bonds. The first domain located at the amino terminus of each chain is variable in amino acid sequence, providing the antibody binding specificities found in each individual antibody. These are known as variable heavy (VH) and variable light (VL) regions. The other domains of each chain are relatively invariant in amino acid sequence and are known as constant heavy (CH) and constant light (CL) regions. For an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies described herein can include, for example, monoclonal antibodies, polyclonal antibodies, multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')$_2$ fragment, a Fd fragment, a Fv fragment, a scFv fragment, a dAb fragment (Ward et al., (1989) Nature 341:544-546), and an isolated complementarity determining region (CDR). These antibody fragments can be obtained using conventional techniques known to those with skill in the art, and the fragments can be screened for utility in the same manner as are intact antibodies.

Antibodies or fragments described herein can be produced by any method known in the art for the synthesis of antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using the methods described in, e.g., Morrison, 1985, Science 229:1202, and humanized antibodies by methods described in, e.g., U.S. Pat. No. 6,180,370.

Additional antibodies described herein are bispecific antibodies and multivalent antibodies, as described in, e.g., Segal et al., J. Immunol. Methods 248:1-6 (2001); and Tutt et al., J. Immunol. 147: 60 (1991).

Insulin-Like Growth Factor 1 (IGF-1R) Antibodies

Insulin-like growth factor 1 receptor is a transmembrane protein found on the surface of human cells activated by insulin-like growth factor 1 (IGF-1) and 2 (IGF-2). IGF-1R is implicated in several cancers including breast cancer, non-small cell lung cancer, prostate cancer, colon cancer, sarcoma, and adrenocortical carcinoma, increased levels of IGF-1R are expressed on the surface of tumor cells of these cancers.

Several IGF-1R antibodies have been developed and investigated for the treatment of various types of cancers including figitumumab, cixutumumab, AMG479, BIIB002, SCH717454, and R1507. After binding to IGF-1R, these antibodies are internalized into the cell and degraded by lysosomal enzymes. The combination of overexpression on tumor cells and internalization offers the possibility of delivering detection agents directly to the tumor site while limiting the exposure of normal tissues to toxic agents.

Modified Polypeptides

The polypeptides of the invention may have a modified amino acid sequence. Modified polypeptides may be substantially identical to the corresponding reference polypeptide (e.g., the amino acid sequence of the modified polypeptide may have at least 50%, 60%, 70%, 75%, 80%, 85%, 90%, 95%, 96%, 97%, 98%, 99%, or 100% identity to the amino acid sequence of the reference polypeptide). In certain embodiments, the modification does not destroy significantly a desired biological activity (e.g., binding to IGF-1R). The modification may reduce (e.g., by at least 5%, 10%, 20%, 25%, 35%, 50%, 60%, 70%, 75%, 80%, 90%, or 95%), may have no effect, or may increase (e.g., by at least 5%, 10%, 25%, 50%, 100%, 200%, 500%, or 1000%) the biological activity of the original polypeptide. The modified polypeptide may have or may optimize a characteristic of a polypeptide, such as in vivo stability, bioavailability, toxicity, immunological activity, immunological identity, and conjugation properties.

Modifications include those by natural processes, such as posttranslational processing, or by chemical modification techniques known in the art. Modifications may occur anywhere in a polypeptide including the polypeptide backbone, the amino acid side chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from posttranslational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to flavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide can also include an amino acid insertion, deletion, or substitution, either conservative or non-conservative (e.g., D-amino acids, desamino acids) in the polypeptide sequence (e.g., where such changes do not substantially alter the biological activity of the polypeptide). In particular, the addition of one or more cysteine residues to the amino or carboxy terminus of any of the polypeptides of the invention can facilitate conjugation of these polypeptides by, e.g., disulfide bonding. For example, a polypeptide can be modified to include a single cysteine residue at the amino-terminus or a single cysteine residue at the carboxy-terminus. Amino acid substitutions can be conservative (i.e., wherein a residue is replaced by another of the same general type or group) or non-conservative (i.e., wherein a residue is replaced by an amino acid of another type). In addition, a naturally occurring amino acid can be substituted for a non-naturally occurring amino acid (i.e., non-naturally occurring conservative amino acid substitution or a non-naturally occurring non-conservative amino acid substitution).

Polypeptides made synthetically can include substitutions of amino acids not naturally encoded by DNA (e.g., non-naturally occurring or unnatural amino acid). Examples of non-naturally occurring amino acids include D-amino acids, N-protected amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogs may be generated by substitutional mutagenesis and retain the biological activity of the original polypeptide. Examples of substitutions identified as "conservative substitutions" are shown in Table 1. If such substitutions result in a change not desired, then other type of substitutions, denominated "exemplary substitutions" in Table 1, or as further described herein in reference to amino acid classes, are introduced and the products screened.

TABLE 1

Amino acid substitutions

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |

TABLE 1-continued

Amino acid substitutions

| Original residue | Exemplary substitution | Conservative substitution |
|---|---|---|
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Substantial modifications in function or immunological identity are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Detection Agents

A detection agent is a molecule or atom which is administered conjugated to a polypeptide, e.g., an antibody or antigen-binding fragment thereof, and is useful in diagnosing a disease by locating the cells containing the antigen, radiation treatment planning, or treatment of a disease. Useful detection agents include, but are not limited to, radioisotopes, dyes (such as with the biotin-strepavidin complex), contrast agents, fluorescent compounds or molecules, luminescent agents, and enhancing agents (e.g., paramagnetic ions) for magnetic resonance imaging (MRI). In order to load a polypeptide component with a detection agent it may be necessary to react it with a reagent having a linker to which are attached the detection agent or multiple detection agents.

Radioisotopes and Radionuclides

Radioisotopes and radionuclides known in the art for their utility as detection agents include, but are not limited to, $^3$H, $^{14}$C, $^{15}$N, $^{18}$F, $^{35}$S, $^{64}$Cu, $^{67}$Cu, $^{75}$Br, $^{76}$Br, $^{77}$Br, $^{89}$Zr, $^{90}$Y, $^{97}$Ru, $^{99}$Tc, $^{105}$Rh, $^{109}$Pd, $^{111}$In, $^{123}$I, $^{124}$I, $^{125}$I, $^{131}$I, $^{149}$Pm, $^{153}$Sm, $^{166}$Ho, $^{177}$Lu, $^{186}$Re, $^{188}$Re, $^{198}$Au, $^{199}$Au, $^{203}$Pb, $^{211}$At, $^{212}$Pb, $^{212}$Pb, $^{213}$Bi, $^{223}$Ra, $^{225}$Ac, $^{227}$Th, and $^{229}$Th.

Metal Chelates

Chelating groups known in the art for their utility as detection agents include, but are not limited to, ethylenediaminetetraacetic acid (EDTA), diethylenetriamiepentaacetic acid (DTPA), porphyrins, polyamines (such as diaminodioximes, diaminodithiols ($N_2S_2$ chelates), and triaminothiol ($N_3S$)), crown ethers, bis-thiosemicarbazones, 1,4,7-triazacyclononane-N,N',N,"-triacetic acid (NOTA), 1,4,7,10-tetraazacyclododecane-1,4,7,10-tetraacetic acid (DOTA), triethylenetetramime (TETA), poly-oximes, and Re/Tc(I) difunctional chelates. Chelates are coupled to the linker using standard chemistries. Chelating groups may be used in metal chelate combinations with metals, such as manganese, iron, and gadolinium and isotopes (e.g., isotopes in the general energy range of 60 to 4,000 key), such as $^{62}$Cu, $^{64}$Cu, $^{67}$Ga, $^{90}$Y, $^{94m}$Tc, $^{99m}$Tc, $^{111}$In, $^{177}$Lu, $^{213}$Bi, $^{225}$Ac, $^{227}$Th, and $^{229}$Th.

Luminescent and Fluorescent Agents

Luminescent and fluroescent agents known in the art for their utility as detection agents include, but are not limited to, indocyanines (eg. Cy3 or Cy5), coumarins, fluorescein (eg. FITC), rhodamines, carbopyronins, oxazines, and luciferins (bioluminescent).

Residualizing Linkers

Residualizing linkers are designed to retain the label intracellularly after lysosomal degradation of the internalized polypeptide conjugate.

Linkers of the invention have the structure of Formula II:

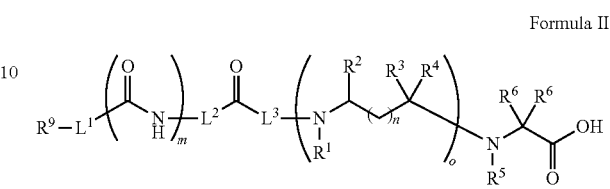

Formula II or a salt thereof, $L^1$ and $L^2$ are independently absent, optionally substituted C1-C6 alkyl, optionally substituted C1-C6 heteroalkyl, optionally substituted C2-C6 alkenyl, optionally substituted C2-C6 heteroalkenyl, optionally substituted C2-C6 alkynyl, optionally substituted C2-C6 heteroalkynyl, optionally substituted C3-C10 cycloalkyl, optionally substituted C4-C10 cycloalkenyl, optionally substituted C4-C10 cycloalkynyl, optionally substituted oxime, optionally substituted hydrazone, optionally substituted aryl, optionally substituted heterocyclic, optionally substituted C2-C100 polyethylene glycol, or $L^4$-B;

$L^3$ is absent or optionally substituted C1-C6 alkyl;

m is 0 or 1;

each $R^1$ and $R^2$ are independently hydrogen, —CH$_2$CO$_2$H, or —CH$_2$CH$_2$CO$_2$H;

each $R^3$ and $R^4$ is independently hydrogen or $R^3$ and $R^4$ combine to form C=O;

n is 0 or 1;

o is an integer between 1 and 10;

$R^5$ is hydrogen or $L^4$-B;

$R^6$ and $R^7$ are independently hydrogen, optionally substituted C1-C6 hetereoalkyl, or $L^4$-B;

$R^9$ is —CO$_2$H, —N=C=O, —N=C=S,

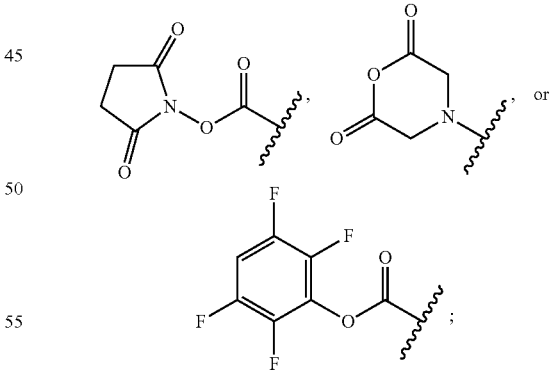

$L^4$ is independently absent, optionally substituted C1-C6 alkyl, optionally substituted C1-C6 heteroalkyl, optionally substituted C2-C6 alkenyl, optionally substituted C2-C6 heteroalkenyl, optionally substituted C2-C6 alkynyl, optionally substituted C2-C6 heteroalkynyl, optionally substituted C3-C10 cycloalkyl, optionally substituted C4-C10 cycloalkenyl, optionally substituted C4-C10 cycloalkynyl, optionally substituted oxime, optionally substituted hydrazone, optionally substituted aryl, or optionally substituted heterocyclic;

B is an organic moiety including a detection agent;
wherein at least one $R^1$ or $R^2$ is —$CH_2CO_2H$ or $CH_2CH_2CO_2H$;
at least one of $L^1$ and $L^2$ are present and when $L^1$ or $L^2$ are absent, m is 0;
and one and only one of $L^1$, $L^2$, $R^5$, $R^6$, and $R^7$ is $L^4$-B.

The linkers of the invention comprise three distinct modules that together result in their increased effectiveness compared to those known in the art.

1. Amine Reactive Linker Module:

The $R^9$ groups of the linkers of the invention react with free amine groups of polypeptides and facilitate one-step conjugation reactions without additional modification to the antibody structure. The linker portion of the module may be any length or lipophilicity to allow for enhanced physiochemical properties and biological activity.

2. Negatively Charged or Zwitterionic Residualizer Module:

The negatively charged or zwitterionic backbone is advantageous as it displays increased residualization compared to positively charged or neutral backbones and is not taken up by the kidney non-specifically after release from the polypeptide in vivo.

3. Detection Agent Module:

The linkers of the invention have an independent module for incorporation of the detection agent allowing for installation of the detection agent without modification to the residualizing backbone.

Administration and Dosage

The present invention also features pharmaceutical compositions that contain a therapeutically effective amount of a compound of the invention. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer (*Science* 249:1527-1533, 1990).

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that include the above mention agents dissolved or suspended in an acceptable carrier, preferably an aqueous carrier, e.g., water, buffered water, saline, or PBS, among others. The compositions may contain pharmaceutically acceptable auxiliary substances as required to approximate physiological conditions, such as pH adjusting and buffering agents, tonicity adjusting agents, wetting agents, or detergents, among others. The invention also provides compositions for oral delivery, which may contain inert ingredients such as binders or fillers for the formulation of a unit dosage form, such as a tablet or a capsule. Furthermore, this invention provides compositions for local administration, which may contain inert ingredients such as solvents or emulsifiers for the formulation of a cream, an ointment, a gel, a paste, or an eye drop.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for radiation treatment planning, diagnostic, or therapeutic treatments. When administered for radiation treatment planning or diagnostic purposes, the conjugate is administered to a subject in a diagnostically effective dose and/or an amount effective to determine the therapeutically effective dose. In therapeutic applications, compositions are administered to a subject (e.g., a human) already suffering from a condition (e.g., cancer) in an amount sufficient to cure or at least partially arrest the symptoms of the disorder and its complications. An amount adequate to accomplish this purpose is defined as a "therapeutically effective amount," an amount of a compound sufficient to substantially improve at least one symptom associated with the disease or a medical condition. For example, in the treatment of cancer, an agent or compound that decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual. The conjugates of the invention can be used for the treatment of cancer by administering to a subject a first dose of any of the foregoing conjugates or compositions in an amount effective for radiation treatment planning, followed by administering a second dose of any of the foregoing conjugates or compositions in a therapeutically effective amount.

Amounts effective for these uses may depend on the severity of the disease or condition and the weight and general state of the subject. The therapeutically effective amount of the compositions of the invention and used in the methods of this invention applied to mammals (e.g., humans) can be determined by the ordinarily-skilled artisan with consideration of individual differences in age, weight, and the condition of the mammal. Because certain conjugates of the invention exhibit an enhanced ability to target cancer cells and residualize, the dosage of the compounds of the invention can be lower than (e.g., less than or equal to about 90%, 75%, 50%, 40%, 30%, 20%, 15%, 12%, 10%, 8%, 7%, 6%, 5%, 4%, 3%, 2%, 1%, 0.5%, or 0.1% of) the equivalent dose of required for a therapeutic effect of the unconjugated agent. The agents of the invention are administered to a subject (e.g., a mammal, such as a human) in an effective amount, which is an amount that produces a desirable result in a treated subject. Therapeutically effective amounts can also be determined empirically by those of skill in the art.

Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The conjugates of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

By "antiproliferative" is meant any anticancer agent, including those antiproliferative agents listed in Table 2, any of which can be used in combination with a conjugate of the invention to treat the medical conditions recited herein. Antiproliferative agents also include organo-platinum derivatives, naphtoquinone and benzoquinone derivatives, chrysophanic acid and anthroquinone derivatives thereof.

TABLE 2

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | SM-11355 (Sumitomo) |
| | ZD-0473 (AnorMED) | AP-5280 (Access) |
| | oxaliplatin | cisplatin |
| | carboplatin | |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |
| Antitumor antibiotics | valrubicin | azonafide |
| | therarubicin | anthrapyrazole |
| | idarubicin | oxantrazole |
| | rubidazone | Iosoxantrone |
| | plicamycin | MEN-10755 (Menarini) |
| | porfiromycin | GPX-100 (Gem Pharmaceuticals) |
| | mitoxantrone (novantrone) | Epirubicin |
| | amonafide | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | ZD 6126 (AstraZeneca) |
| | T 138067 (Tularik) | AZ10992 (Asahi) |

TABLE 2-continued

| | | |
|---|---|---|
| | cryptophycin 52 (Eli Lilly) | IDN-5109 (Indena) |
| | vinflunine (Fabre) | AVLB (Prescient NeuroPharma) |
| | auristatin PE (Teikoku Hormone) | azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | dolastatin-10 (NIH) |
| | taxoprexin (Protarga) | CA-4 (OXiGENE) |
| | SB 408075 (GlaxoSmithKline) | docetaxel |
| | Vinorelbine | vincristine |
| | Trichostatin A | paclitaxel |
| Aromatase inhibitors | aminoglutethimide | YM-511 (Yamanouchi) |
| | atamestane (BioMedicines) | formestane |
| | letrozole | exemestane |
| | anastrazole | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | edotreotide (Novartis) |
| | glufosfamide (Baxter International) | mafosfamide (Baxter International) |
| | albumin + 32P (Isotope Solutions) | apaziquone (Spectrum Pharmaceuticals) |
| | thymectacin (NewBiotics) | O6 benzyl guanine (Paligent) |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immuno-modulators | interferon | dexosome therapy (Anosys) |
| | oncophage (Antigenics) | pentrix (Australian Cancer Technology) |
| | GMK (Progenics) | |
| | adenocarcinoma vaccine (Biomira) | ISF-154 (Tragen) |
| | CTP-37 (AVI BioPharma) | cancer vaccine (Intercell) |
| | IRX-2 (Immuno-Rx) | norelin (Biostar) |
| | PEP-005 (Peplin Biotech) | BLP-25 (Biomira) |
| | synchrovax vaccines (CTL Immuno) | MGV (Progenics) |
| | melanoma vaccine (CTL Immuno) | β-alethine (Dovetail) |
| | p21 RAS vaccine (GemVax) | CLL therapy (Vasogen) |
| | MAGE-A3 (GSK) | Ipilimumab (BMS), |
| | nivolumab (BMS) | CM-10 (cCam Biotherapeutics) |
| | abatacept (BMS) | MPDL3280A (Genentech) |
| Hormonal and antihormonal agents | estrogens | dexamethasone |
| | conjugated estrogens | prednisone |
| | ethinyl estradiol | methylprednisolone |
| | chlortrianisen | prednisolone |
| | idenestrol | aminoglutethimide |
| | hydroxyprogesterone caproate | leuprolide |
| | medroxyprogesterone | octreotide |
| | testosterone | mitotane |
| | testosterone propionate; | P-04 (Novogen) |
| | fluoxymesterone | 2-methoxyestradiol (EntreMed) |
| | methyltestosterone | arzoxifene (Eli Lilly) |
| | diethylstilbestrol | tamoxifen |
| | megestrol | toremofine |
| | bicalutamide | goserelin |
| | flutamide | Leuporelin |
| | nilutamide | bicalutamide |
| Photodynamic agents | talaporfin (Light Sciences) | Pd-bacteriopheophorbide (Yeda) |
| | Theralux (Theratechnologies) | lutetium texaphyrin (Pharmacyclics) |
| | motexafin gadolinium (Pharmacyclics) | hypericin |
| Kinase Inhibitors | imatinib (Novartis) | EKB-569 (Wyeth) |
| | leflunomide (Sugen/Pharmacia) | kahalide F (PharmaMar) |
| | ZD1839 (AstraZeneca) | CEP-701 (Cephalon) |
| | erlotinib (Oncogene Science) | CEP-751 (Cephalon) |
| | canertinib (Pfizer) | MLN518 (Millenium) |
| | squalamine (Genaera) | PKC412 (Novartis) |
| | SU5416 (Pharmacia) | Phenoxodiol (Novogen) |

TABLE 2-continued

| | |
|---|---|
| SU6668 (Pharmacia) | C225 (ImClone) |
| ZD4190 (AstraZeneca) | rhu-Mab (Genentech) |
| ZD6474 (AstraZeneca) | MDX-H210 (Medarex) |
| vatalanib (Novartis) | 2C4 (Genentech) |
| PKI166 (Novartis) | MDX-447 (Medarex) |
| GW2016 (GlaxoSmithKline) | ABX-EGF (Abgenix) |
| EKB-509 (Wyeth) | IMC-1C11 (ImClone) |
| trastuzumab (Genentech) | Tyrphostins |
| OSI-774 (Tarceva ™) | Gefitinib (Iressa) |
| CI-1033 (Pfizer) | PTK787 (Novartis) |
| SU11248 (Pharmacia) | EMD 72000 (Merck) |
| RH3 (York Medical) | Emodin |
| Genistein | Radicinol |
| Radicinol | Vemurafenib (B-Raf enzyme |
| Met-MAb (Roche) | inhibitor, Daiichi Sankyo) |
| SR-27897 (CCK A inhibitor, Sanofi-Synthelabo) | ceflatonin (apoptosis promotor, ChemGenex) |
| tocladesine (cyclic AMP agonist, Ribapharm) | BCX-1777 (PNP inhibitor, BioCryst) |
| alvocidib (CDK inhibitor, Aventis) | ranpirnase (ribonuclease stimulant, Alfacell) |
| CV-247 (COX-2 inhibitor, Ivy Medical) | galarubicin (RNA synthesis inhibitor, Dong-A) |
| P54 (COX-2 inhibitor, Phytopharm) | tirapazamine (reducing agent, SRI |
| CapCell ™ (CYP450 stimulant, Bavarian Nordic) | International) |
| GCS-100 (gal3 antagonist, GlycoGenesys) | N-acetylcysteine (reducing agent, Zambon) |
| G17DT immunogen (gastrin inhibitor, Aphton) | R-flurbiprofen (NF-kappaB inhibitor, Encore) |
| efaproxiral (oxygenator, Allos Therapeutics) | 3CPA (NF-kappaB inhibitor, Active Biotech) |
| PI-88 (heparanase inhibitor, Progen) | seocalcitol (vitamin D receptor agonist, Leo) |
| tesmilifene (histamine antagonist, YM | 131-I-TM-601 (DNA antagonist, |
| BioSciences) | TransMolecular) |
| histamine (histamine H2 receptor agonist, Maxim) | eflornithine (ODC inhibitor, ILEX Oncology) |
| tiazofurin (IMPDH inhibitor, Ribapharm) | minodronic acid (osteoclast inhibitor, |
| cilengitide (integrin antagonist, Merck KGaA) | Yamanouchi) |
| SR-31747 (IL-1 antagonist, Sanofi-Synthelabo) | indisulam (p53 stimulant, Eisai) |
| CCI-779 (mTOR kinase inhibitor, Wyeth) | aplidine (PPT inhibitor, PharmaMar) |
| exisulind (PDE V inhibitor, Cell Pathways) | gemtuzumab (CD33 antibody, Wyeth Ayerst) |
| CP-461 (PDE V inhibitor, Cell Pathways) | PG2 (hematopoiesis enhancer, |
| AG-2037 (GART inhibitor, Pfizer) | Pharmagenesis) |
| WX-UK1 (plasminogen activator inhibitor, Wilex) | Immunol ™ (triclosan oral rinse, Endo) |
| PBI-1402 (PMN stimulant, ProMetic LifeSciences) | triacetyluridine (uridine prodrug, Wellstat) |
| bortezomib (proteasome inhibitor, Millennium) | SN-4071 (sarcoma agent, Signature |
| SRL-172 (T cell stimulant, SR Pharma) | BioScience) |
| TLK-286 (glutathione S transferase inhibitor, | TransMID-107 ™ (immunotoxin, KS Biomedix) |
| Telik) | PCK-3145 (apoptosis promotor, Procyon) |
| PT-100 (growth factor agonist, Point | doranidazole (apoptosis promotor, Pola) |
| Therapeutics) | CHS-828 (cytotoxic agent, Leo) |
| midostaurin (PKC inhibitor, Novartis) | trans-retinoic acid (differentiator, NIH) |
| bryostatin-1 (PKC stimulant, GPC Biotech) | MX6 (apoptosis promotor, MAXIA) |
| CDA-II (apoptosis promotor, Everlife) | apomine (apoptosis promotor, ILEX Oncology) |
| SDX-101 (apoptosis promotor, Salmedix) | urocidin (apoptosis promotor, Bioniche) |
| rituximab (CD20 antibody, Genentech | Ro-31-7453 (apoptosis promotor, La Roche) |
| carmustine | brostallicin (apoptosis promotor, Pharmacia) |
| Mitoxantrone | β-lapachone |
| Bleomycin | gelonin |
| Absinthin | cafestol |
| Chrysophanic acid | kahweol |
| Cesium oxides | caffeic acid |
| BRAF inhibitors, | Tyrphostin AG |
| PDL1 inhibitors | PD-1 inhibitors |
| MEK inhibitors | CTLA-4 inhibitors |
| bevacizumab | sorafenib |
| angiogenesis inhibitors | |
| dabrafenib | |

The following Examples are intended to illustrate the synthesis of a representative number of conjugates and the use of these conjugates for the treatment of cancer. Accordingly, the Examples are intended to illustrate but not to limit the invention. Additional compounds not specifically exemplified may be synthesized using conventional methods in combination with the methods described herein.

EXAMPLES

General Methods

All reactions were carried out under a nitrogen atmosphere with dry solvents under anhydrous conditions, unless otherwise specified. Reactions were monitored by thin-layer chromatography (TLC) carried out on 0.25 mm E. Merck silica gel plates (60E-254) using UV light and an ethanolic solution of phosphomolybdic acid and cerium sulfate followed by heating as visualizing strategies. E. Merck silica gel (60, particle size 0.040-0.063 mm) was used for flash column chromatography. Analytical HPLC-MS was performed using a Waters Acquity HPLC-MS system comprised of a Waters Acquity Binary Solvent Manager, a Waters Acquity Sample Manager (samples cooled to 10° C.), a Water Acquity Column Manager (column temperature 30° C.), a Waters Acquity Photodiode Array Detector (monitoring at 254 nm and 214 nm), a Waters Acquity TQD with electrosparay ionization and a Waters Acquity BEH C18, 2.1×50 (1.7 µm) column. Preparative HPLC was performed using a Waters HPLC system comprised of a Waters 1525

Binary HPLC pump, a Waters 2489 UV/Visible Detector (monitoring at 254 nm and 214 nm) and a Waters XBridge Prep phenyl or C18 19×100 mm (5 µm) column. Analysis and purification of radioactive materials were performed using similar HPLC systems equipped with an additional Bioscan Flow Count radiodetector (FC-3300). SEC was performed on a Phenomenex BioSep s2000, 7.8×300 mm, 1 mL/min, A220/280 nm under isocratic conditions with mobile phase of 100 mM PO4- at pH 6.8.

HPLC elution method 1: Waters Acquity BEH C18 2.1× 50 (1.7 µm) column; mobile phase A: $H_2O$ (0.1% v/v TFA); mobile phase B: acetonitrile (0.1% v/v TFA); flow rate=0.3 mL/min; 0→3 min, 90→0% A; 3→4 min, 0% A.

HPLC elution method 2: Waters XBridge Prep Phenyl 19×100 mm (5 µm) column; mobile phase A: $H_2O$ (0.5% v/v AcOH); mobile phase B: Acetonitrile (0.5% v/v AcOH); flow rate: 10 mL/min; 0→10 minutes, 50%→30% A; 10→12 minutes, 30% A.

HPLC elution method 3: Waters XBridge Prep C18 OBD 19×100 mm (5 µm) column; mobile phase A: $H_2O$ (0.1% v/v TFA); mobile phase B: acetonitrile (0.1% v/v TFA); flow rate: 11 mL/min; 0→11.5 minutes, 75%→56% A.

HPLC elution method 4: Waters Acquity BEH C18 2.1× 50 (1.7 µm) column; mobile phase A: $H_2O$ (0.1% v/v TFA); mobile phase B: acetonitrile (0.1% v/v TFA); flow rate=0.3 mL/min; 0→8 min, 90→0% A.

HPLC elution method 5: Waters XBridge Prep C18 OBD 19×100 mm (5 µm) column; mobile phase A: $H_2O$ (0.1% v/v TFA); mobile phase B: acetonitrile (0.1% v/v TFA); flow rate: 10 mL/min; 0→10 minutes, 80%→50% A.

HPLC elution method 6: Waters XBridge Prep Phenyl 19×100 mm (5 µm) column; mobile phase A: $H_2O$ (0.5% v/v AcOH); mobile phase B: Acetonitrile (0.5% v/v AcOH); flow rate: 10 mL/min; 0→2 minutes, 46% A; 2→13 minutes, 46%→30% A.

Example 1

Synthesis of CPD-1022 and CPD-1023

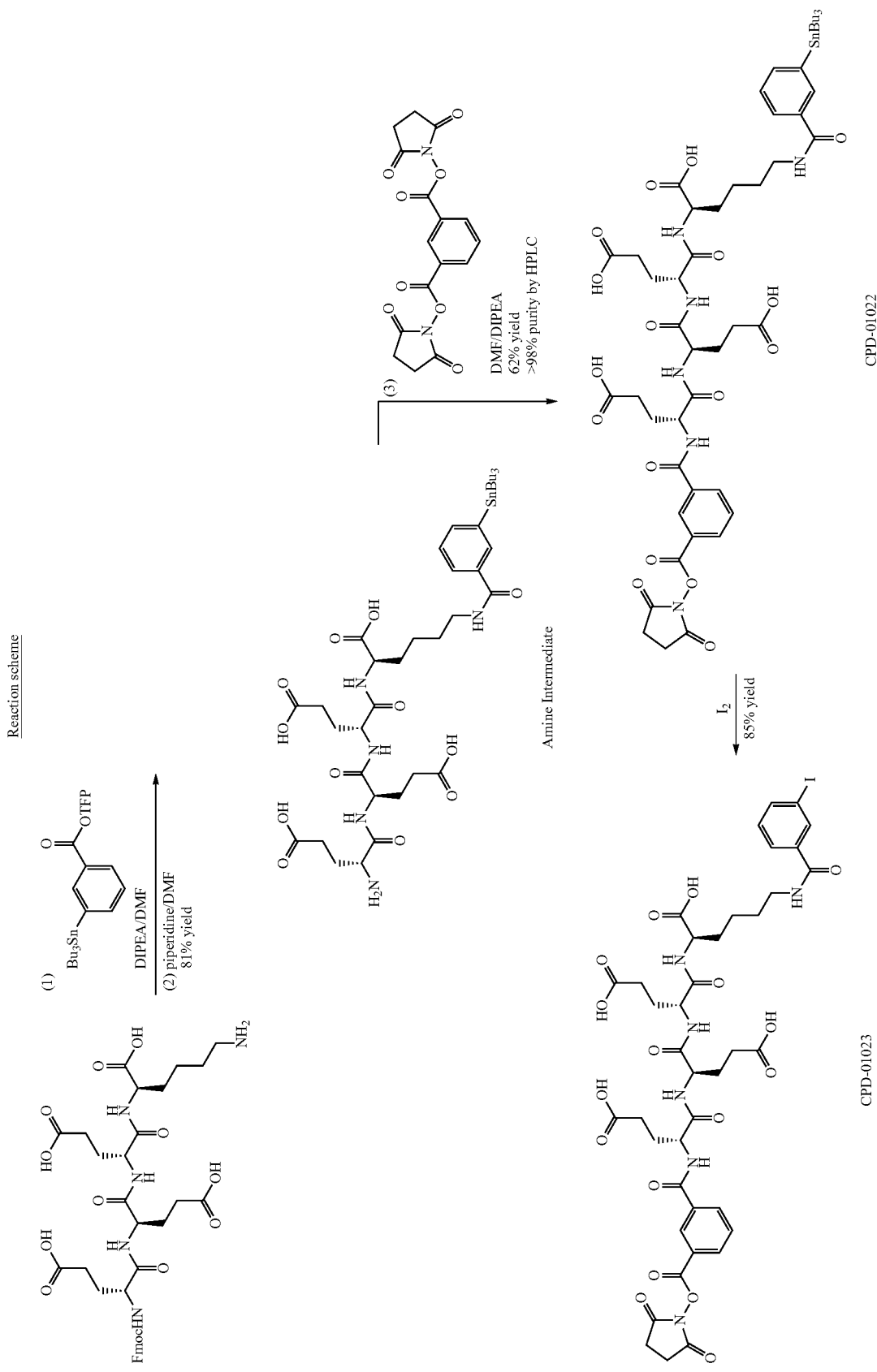

Amine Intermediate:

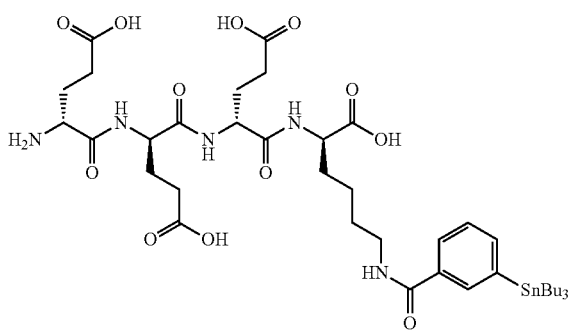

The tetrapeptide backbone of CPD-1022 (Fmoc-D-Glu-D-Glu-D-Glu-D-Lys-OH) was prepared using standard solid phase peptide synthesis techniques. To a solution of the backbone tetrapeptide (100 mg, 0.132 mmol) in 1.5 mL of DMF were added 2,3,5,6-tetrafluorophenyl 3-tributylstannylbenzoate (191 mg, 0.341 mmol) and diisopropylethylamine (40 μL, 0.229 mmol) at room temperature. The reaction solution was stirred for 1 hour then diluted with a mixture of cold diethyl ether and hexanes (45 mL, 4:1 v/v). The resultant suspension was centrifuged at 4000 rpm for 15 minutes and the white precipitate (138 mg, 0.120 mmol, 91% yield) was collected and washed with 20 mL of cold diethyl ether. To this white solid (90 mg, 0.078 mmol) was added 1.0 mL of 20% piperidine/DMF and the mixture was stirred at room temperature for 20 minutes before dilution with cold diethyl ether (45 mL). The resultant white precipitate (collected after centrifuging at 4000 rpm for 15 minutes) was taken up in acetonitrile/water/AcOH (4.0 mL, 45:45:10 v/v/v) and loaded on a C-18 plus Seppak SPE cartridge. The cartridge was flushed with acetonitrile/water (20 mL, 1:2 v/v) first to remove residual piperidine and the desired product was eluted off the cartridge with acetonitrile/water (200 mL, 3:1 v/v). The final product was obtained as white amorphous powder after evaporation of solvents (65 mg, 0.07 mmol, 90% yield).

HPLC-MS elution method 1; retention time: 3.03 min; MS (positive ESI): found m/z 928.0 [M+H]$^+$. $C_{40}H_{66}N_5O_{12}Sn$ (calc. 928.3).

Synthesis of CPD-1022:

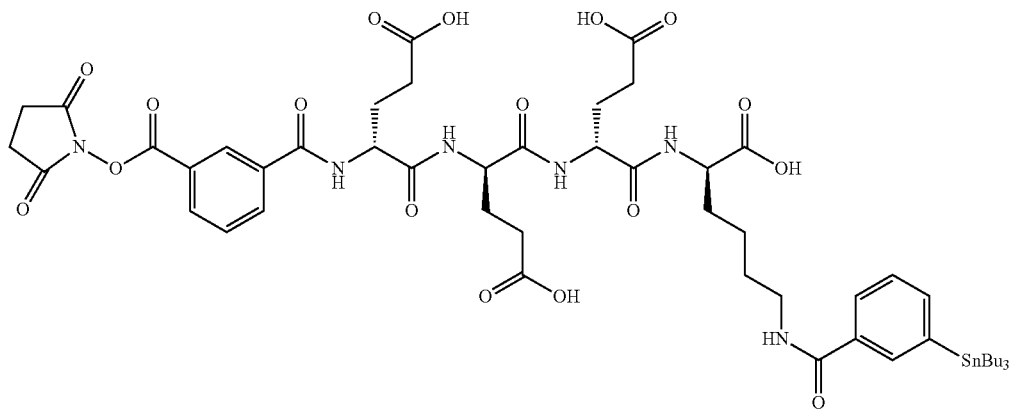

To a solution of the above free amine (24 mg, 0.026 mmol) in DMF (0.5 mL) were added an excess of isophthalic acid NHS ester (100 mg, 0.278 mmol, 10.7 equiv.) and diisopropylethylamine (6.0 μL, 0.035 mmol) at room temperature. LC-MS indicated the reaction was complete within 10 minutes. Cold ether was added to precipitate the crude product, which was collected after centrifuging at 4000 rpm for 15 minutes. Purification was accomplished by preparative HPLC (method 2, retention time: 9.9 min) to afford CPD-1022 in 62% yield (19 mg, 0.016 mmol).

HPLC-MS elution method 1; retention time: 3.30 min; MS (positive ESI): found m/z 1173.1 [M+H]$^+$. $C_{52}H_{73}N_6O_{17}Sn$ (calc. 1173.4).

$^1$H NMR (700 MHz, DMSO-$d_6$) δ 8.92 (1H, d, J=7.4 Hz), 8.60 (1H, s), 8.44 (1H, t, J=5.5 Hz), 8.32 (1H, d, J=7.8 Hz), 8.26 (1H, d, J=7.8 Hz), 8.16 (1H, d, J=7.6 Hz), 8.14 (1H, m), 7.99 (1H, d, J=7.4 Hz), 7.89 (1H, s), 7.77 (1H, t, J=7.8 Hz), 7.74 (1H, d, J=7.8 Hz), 7.56 (1H, d, J=7.1 Hz), 7.40 (1H, dd, J=7.8, 7.1 Hz), 4.48 (1H, m), 4.32-4.26 (2H, m), 4.13 (1H, m), 3.24 (2H, dt, J=5.5, 6.8 Hz), 2.92 (4H, s), 2.40-2.20 (6H, m), 2.05 (1H, m), 1.97-1.86 (3H, m), 1.82-1.69 (3H, m), 1.63 (1H, m), 1.58-1.43 (8H, m), 1.41-1.33 (2H, m), 1.30 (6H, m), 1.08 (6H, m), 0.86 (9H, t, J=7.3 Hz) (Sn—H couplings are not presented for simplicity);

$^{13}$C NMR (175 MHz, DMSO-$d_6$) δ 174.00, 173.44, 171.17, 171.08, 170.90, 170.22, 166.48, 165.19, 161.44, 141.37, 138.75, 135.12, 134.75, 134.46, 133.99, 132.58, 129.69, 128.96, 127.65, 126.78, 124.58, 53.11, 52.01, 51.89, 51.58, 39.01, 30.61, 30.52, 30.14, 29.98, 28.90, 28.56, 27.48, 27.28, 26.79, 26.65, 25.56, 22.99, 13.54, 9.18 (two carboxyls missing due to signal overlapping; Sn—C couplings are not presented for simplicity).

CPD-1023:

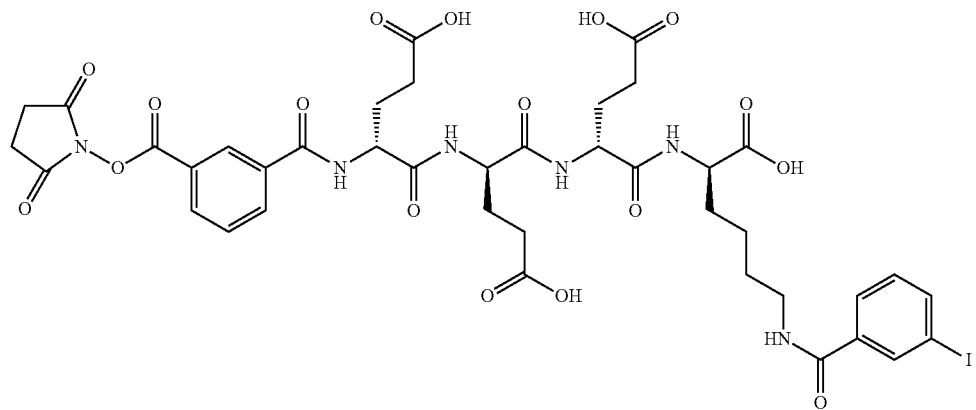 [SMILES: O=C(O)CC[C@@H](NC(=O)c1cccc(C(=O)ON2C(=O)CCC2=O)c1)C(=O)N[C@H](CCC(=O)O)C(=O)N[C@H](CCC(=O)O)C(=O)N[C@H](CCCCNC(=O)c1cccc(I)c1)C(=O)O]

To a solution of CPD-1022 (5.0 mg, 4.3 μmol) in acetonitrile/water (0.5 mL, 3:1 v/v) was added iodine (2.0 mg, 7.9 μmol). Excess of iodine was quenched by the addition of $Na_2S_2O_5$ (0.1 mL, 0.1 M aq.) and the reaction mixture purified by preparative HPLC (method 3, retention time: 10.4 min) to give the desired product in 85% yield (3.7 mg, 3.7 μmol).

HPLC-MS elution method 1; retention time: 1.79 min; MS (positive ESI): found m/z 1009.4 [M+H]$^+$. $C_{40}H_{46}IN_6O_{17}$ (calc. 1009.2).

$^1$H NMR (700 MHz, DMSO-$d_6$) δ 8.92 (1H, d, J=7.5 Hz), 8.60 (1H, s), 8.55 (1H, t, J=5.5 Hz), 8.32 (1H, d, J=7.9 Hz), 8.26 (1H, d, J=7.8 Hz), 8.18 (1H, s), 8.17-8.12 (2H, m), 7.98 (1H, d, J=7.8 Hz), 7.88 (1H, d, J=7.7 Hz), 7.85 (1H, d, J=7.9 Hz), 7.78 (1H, dd, J=7.9, 7.8 Hz), 7.27 (1H, dd, J=7.9, 7.7 Hz), 4.47 (1H, m), 4.32-4.25 (2H, m), 4.13 (1H, m), 3.23 (2H, dt, J=5.5, 6.8 Hz), 2.92 (4H, s), 2.41-2.22 (6H, m), 2.05 (1H, m), 1.97-1.88 (3H, m), 1.81-1.70 (3H, m), 1.63 (1H, m), 1.55-1.48 (2H, m), 1.40-1.33 (2H, m);

$^{13}$C NMR (175 MHz, DMSO-$d_6$) δ 174.01, 173.99, 173.98, 173.44, 171.19, 171.10, 170.91, 170.23, 165.20, 164.53, 161.45, 139.53, 136.63, 135.56, 135.12, 134.47, 132.59, 130.44, 129.70, 128.96, 126.63, 124.57, 94.62, 53.13, 51.96, 51.89, 51.55, 39.09, 30.54, 30.51, 30.12, 29.98, 28.65, 27.47, 27.27, 26.78, 25.56, 22.93.

Example 2
Synthesis of CPD-1052
CPD-1051:
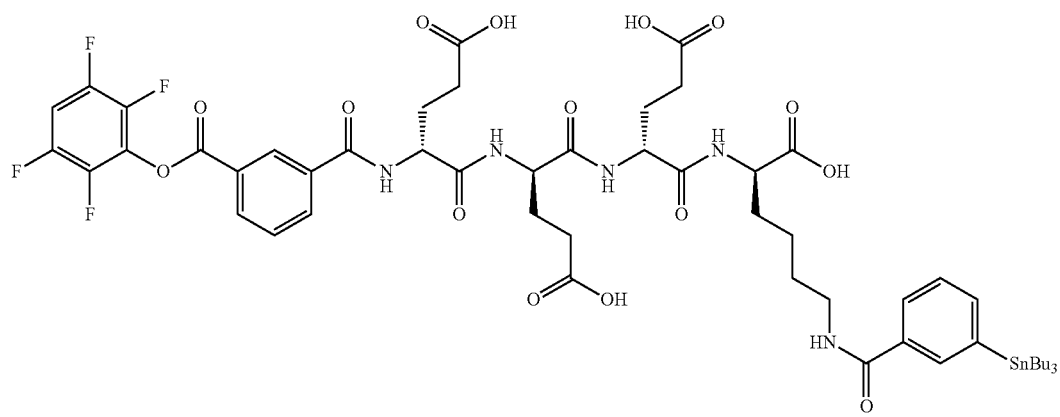
The title compound was prepared in a similar manner to the synthesis of CPD-1022.
HPLC-MS elution method 1; retention time: 3.60 min; MS (positive ESI): found m/z 1224.7 [M+H]$^+$. $C_{54}H_{70}F_4N_5O_{15}Sn$ (calc. 1224.4).
CPD-1052:
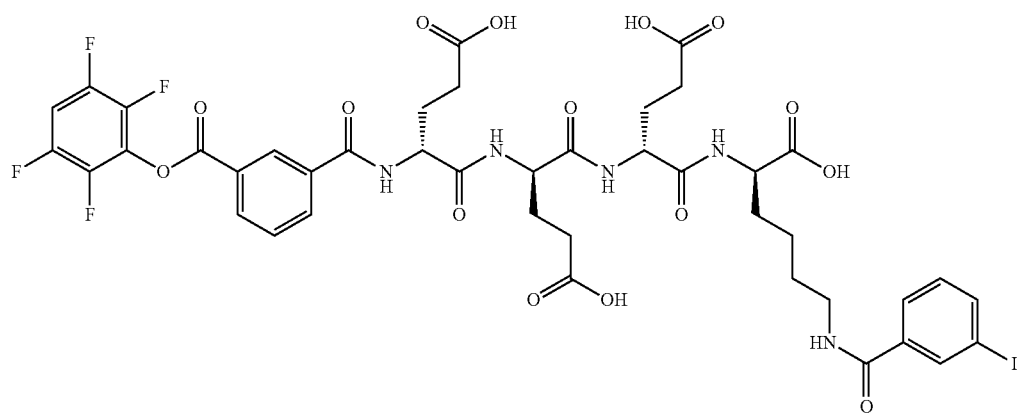 [SMILES: O=C(O)CC[C@@H](NC(=O)c1cccc(C(=O)Oc2c(F)c(F)cc(F)c2F)c1)C(=O)N[C@H](CCC(=O)O)C(=O)N[C@H](CCC(=O)O)C(=O)N[C@H](CCCCNC(=O)c1cccc(I)c1)C(=O)O]

The title compound was prepared from CPD-1051 in a similar manner to the synthesis of CPD-1023.

HPLC-MS elution method 1; retention time: 2.19 min; MS (positive ESI): found m/z 1060.4 [M+H]$^+$. $C_{42}H_{43}F_4IN_5O_{15}$ (calc. 1060.2).

Example 3

Synthesis of CPD-1055

CPD-1054:

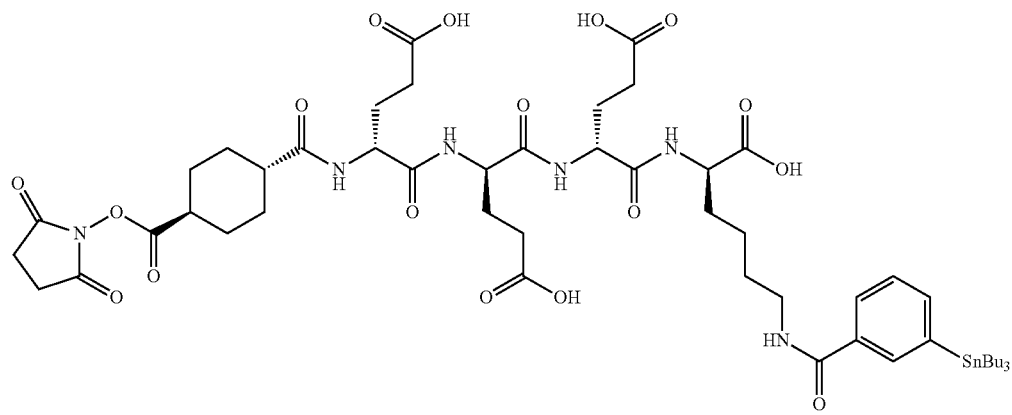

The title compound was prepared in a similar manner to the synthesis of CPD-1022.

HPLC-MS elution method 1; retention time: 3.27 min; MS (positive ESI): found m/z 1179.6 [M+H]$^+$. $C_{52}H_{79}N_6O_{17}Sn$ (calc. 1179.4).

CPD-1055:

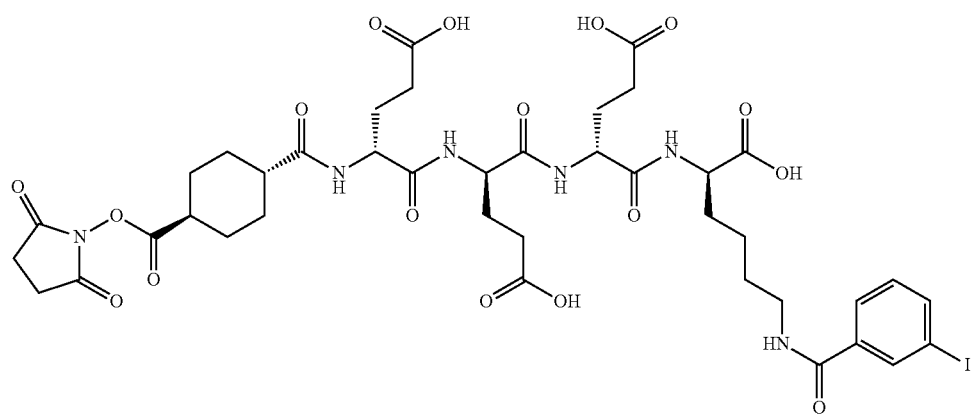 [SMILES: O=C(O)CC[C@@H](NC(=O)[C@@H](CCC(=O)O)NC(=O)[C@@H](CCC(=O)O)NC(=O)[C@H]1CC[C@H](C(=O)ON2C(=O)CCC2=O)CC1)C(=O)N[C@H](CCCCNC(=O)c1cccc(I)c1)C(=O)O]

The title compound was prepared from CPD-1054 in a similar manner to the synthesis of CPD-1023.

HPLC-MS elution method 1; retention time: 1.75 min; MS (positive ESI): found m/z 1014.9 [M+H]$^+$. $C_{40}H_{52}IN_6O_{17}$ (calc. 1015.2).

Example 4

Synthesis of CPD-1065

CPD-1064:

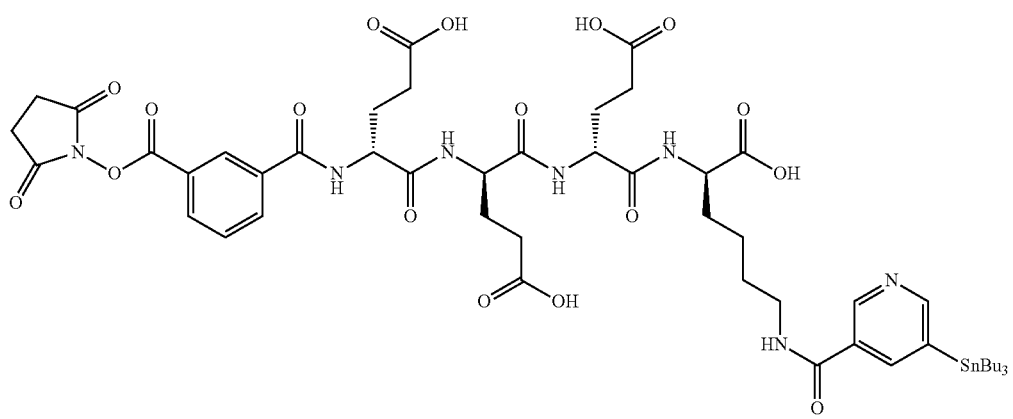

The title compound was prepared in a similar manner to the synthesis of CPD-1022.

HPLC-MS elution method 1; retention time: 2.43 min; MS (positive ESI): found m/z 1174.6 [M+H]$^+$. $C_{51}H_{72}N_7O_{17}Sn$ (calc. 1174.4).

CPD-1065:

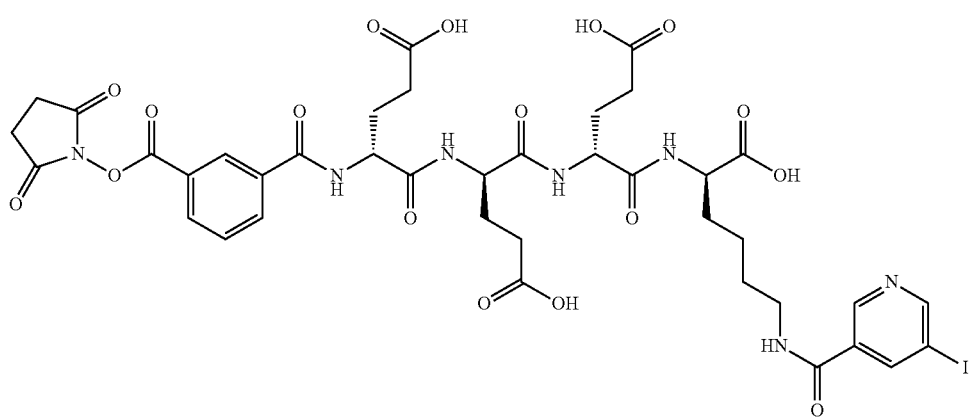 [SMILES: O=C(O)CC[C@@H](NC(=O)c1cccc(C(=O)ON2C(=O)CCC2=O)c1)C(=O)N[C@H](CCC(=O)O)C(=O)N[C@H](CCC(=O)O)C(=O)N[C@H](CCCCNC(=O)c1cncc(I)c1)C(=O)O]

The title compound was prepared from CPD-1064 in a similar manner to the synthesis of CPD-1023.

HPLC-MS elution method 1; retention time: 1.54 min; MS (positive ESI): found m/z 1010.4 [M+H]$^+$. $C_{39}H_{45}IN_7O_{17}$ (calc. 1010.2).

Example 5

Synthesis of CPD-1067

CPD-1066:

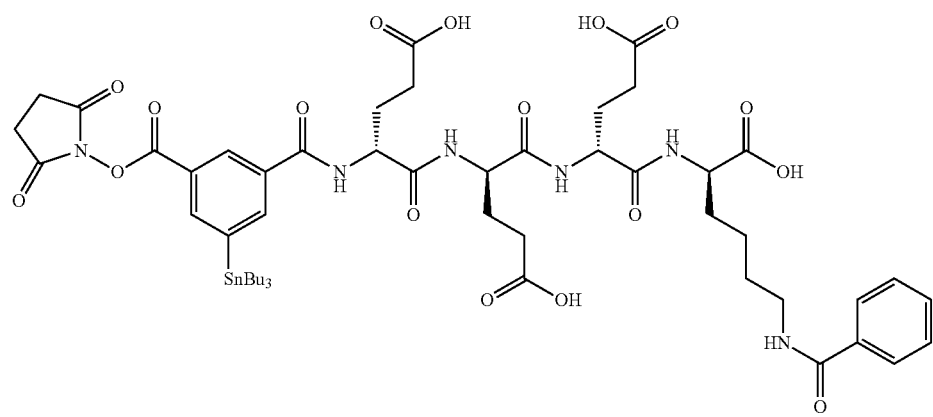

The title compound was prepared in a similar manner to the synthesis of CPD-1022.

HPLC-MS elution method 4; retention time: 5.97 min; MS (positive ESI): found m/z 1173.7 [M+H]$^+$. $C_{52}H_{73}N_6O_{17}Sn$ (calc. 1173.4).

CPD-1067:

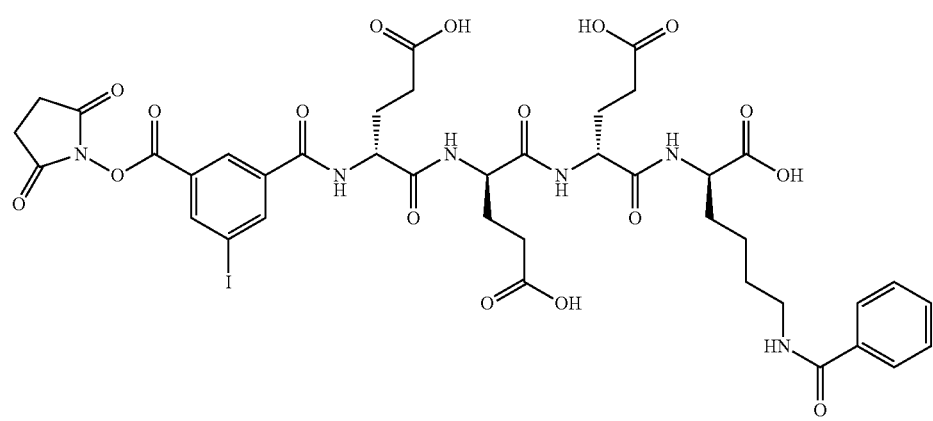 [SMILES: O=C(O)CC[C@@H](NC(=O)c1cc(I)cc(C(=O)ON2C(=O)CCC2=O)c1)C(=O)N[C@H](CCC(=O)O)C(=O)N[C@H](CCC(=O)O)C(=O)N[C@H](CCCCNC(=O)c1ccccc1)C(=O)O]

The title compound was prepared from CPD-1066 in a similar manner to the synthesis of CPD-1023.

HPLC-MS elution method 4; retention time: 3.05 min; MS (positive ESI): found m/z 1009.4 [M+H]$^+$. $C_{40}H_{46}IN_6O_{17}$ (calc. 1009.2).

Example 6

Synthesis of CPD-1048

CPD-1047:

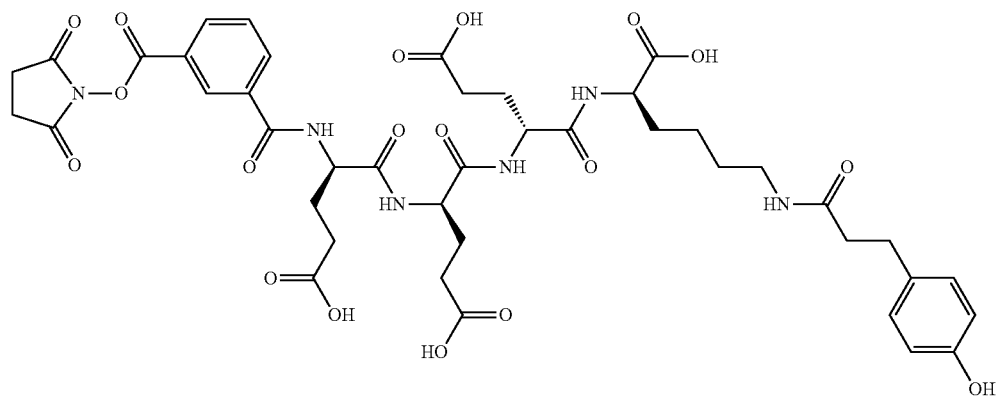 [SMILES: O=C(O)CC[C@@H](NC(=O)c1cccc(C(=O)ON2C(=O)CCC2=O)c1)C(=O)N[C@H](CCC(=O)O)C(=O)N[C@H](CCC(=O)O)C(=O)N[C@H](CCCCNC(=O)CCc1ccc(O)cc1)C(=O)O]

The title compound was prepared in a similar manner to the synthesis of CPD-1022.

HPLC-MS elution method 4; retention time: 2.31 min; MS (positive ESI): found m/z 927.5 [M+H]$^+$. $C_{42}H_{51}N_6O_{18}$ (calc. 927.3).

CPD-1048:

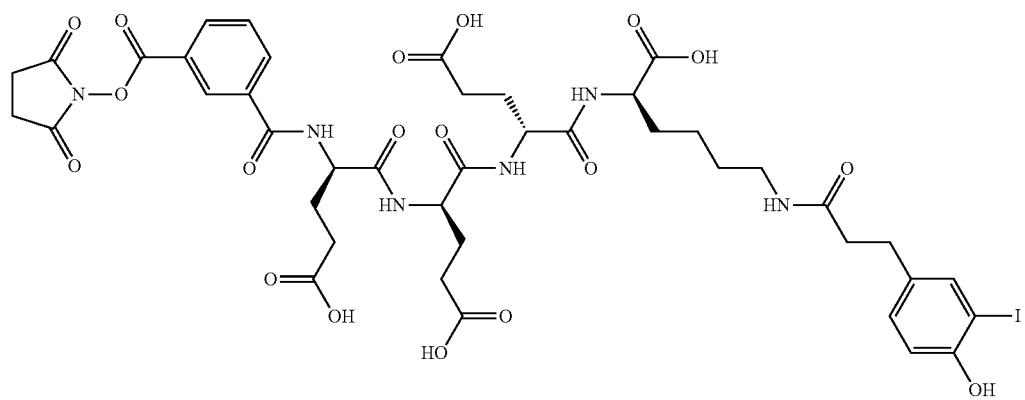 [SMILES: O=C(O)CC[C@@H](NC(=O)c1cccc(C(=O)ON2C(=O)CCC2=O)c1)C(=O)N[C@H](CCC(=O)O)C(=O)N[C@H](CCC(=O)O)C(=O)N[C@H](CCCCNC(=O)CCc1ccc(O)c(I)c1)C(=O)O]

The title compound was prepared in a similar manner to the synthesis of CPD-1022.

HPLC-MS elution method 4. retention time: 2.76 min; MS (positive ESI): found m/z 1053.4 [M+H]$^+$. $C_{42}H_{50}IN_6O_{18}$ (calc. 1053.2).

Example 7

Synthesis of CPD-1107

CPD-1107:

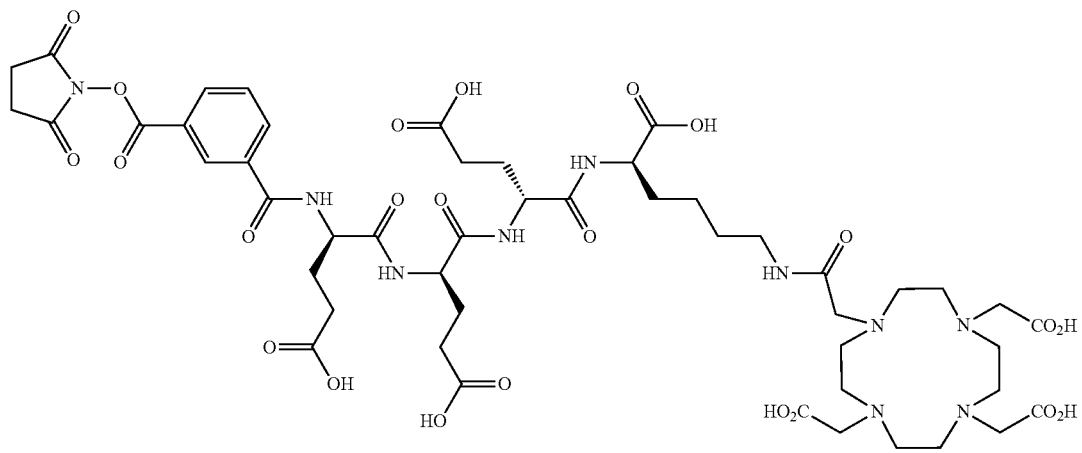 [SMILES: O=C(O)CC[C@@H](NC(=O)c1cccc(C(=O)ON2C(=O)CCC2=O)c1)C(=O)N[C@H](CCC(=O)O)C(=O)N[C@H](CCC(=O)O)C(=O)N[C@H](CCCCNC(=O)CN1CCN(CC(=O)O)CCN(CC(=O)O)CCN(CC(=O)O)CC1)C(=O)O]

The title compound was prepared in a similar manner to the synthesis of CPD-1022.

HPLC-MS elution method 4; retention time: 1.63 min; MS (positive ESI): found m/z 1165.7 [M+H]$^+$. $C_{49}H_{69}N_{10}O_{23}$ (calc. 1165.4).

Example 8

Synthesis of CPD-1072

CPD-1071:

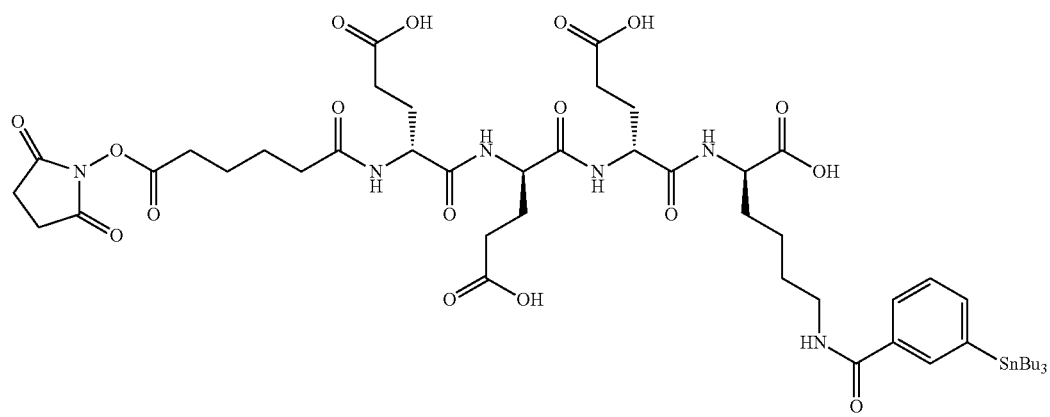

The title compound was prepared in a similar manner to the synthesis of CPD-1022.

HPLC-MS elution method 1; retention time: 3.27 min; MS (positive ESI): found m/z 1153.7 [M+H]$^+$. $C_{50}H_{77}N_6O_{17}Sn$ (calc. 1153.4).

CPD-1072:

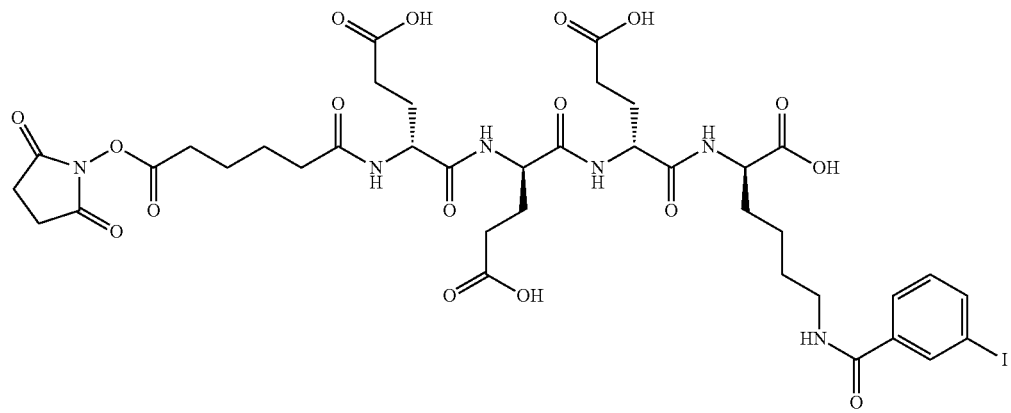 [SMILES: O=C(O)CC[C@@H](NC(=O)CCCCC(=O)ON1C(=O)CCC1=O)C(=O)N[C@H](CCC(=O)O)C(=O)N[C@H](CCC(=O)O)C(=O)N[C@H](CCCCNC(=O)c1cccc(I)c1)C(=O)O]

The title compound was prepared from CPD-1071 in a similar manner to the synthesis of CPD-1023.

HPLC-MS elution method 1; retention time: 1.71 min; MS (positive ESI): found m/z 989.4 [M+H]$^+$. $C_{38}H_{50}IN_6O_{17}$ (calc. 989.2).

Example 9

Synthesis of CPD-1081

CPD-1080:

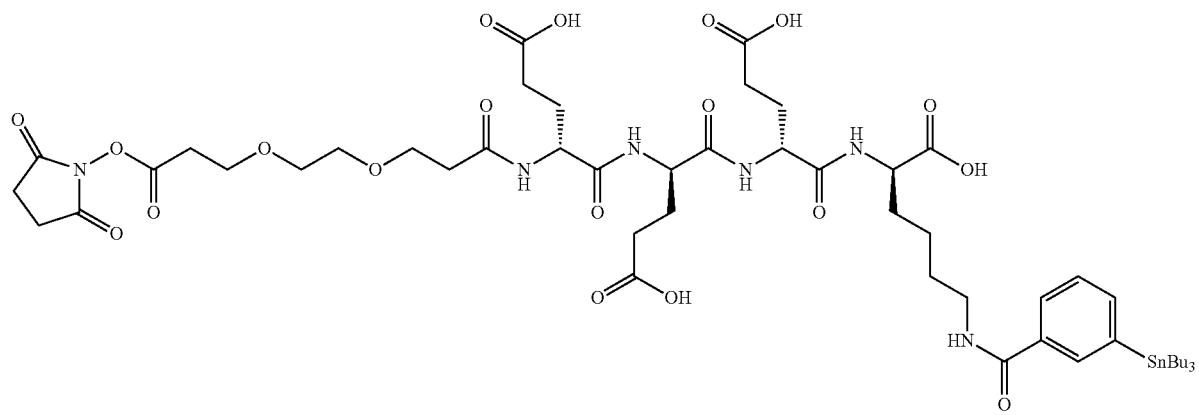

The title compound was prepared in a similar manner to the synthesis of CPD-1022.

HPLC-MS elution method 1; retention time: 3.23 min; MS (positive ESI): found m/z 1213.2 [M+H]$^+$. $C_{52}H_{81}N_6O_{19}Sn$ (calc. 1213.5).

CPD-1081:

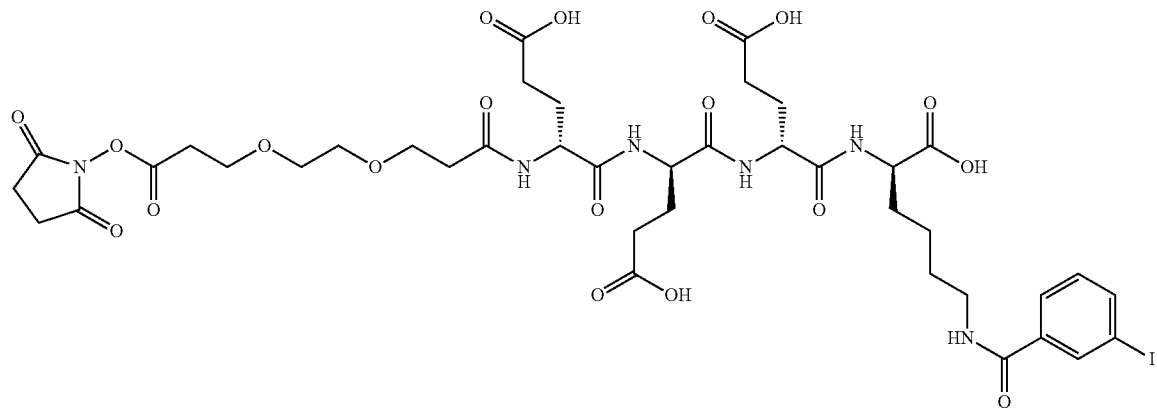 [SMILES: O=C(O)CC[C@@H](NC(=O)CCOCCOCCC(=O)ON1C(=O)CCC1=O)C(=O)N[C@H](CCC(=O)O)C(=O)N[C@H](CCC(=O)O)C(=O)N[C@H](CCCCNC(=O)c1cccc(I)c1)C(=O)O]

The title compound was prepared from CPD-1080 in a similar manner to the synthesis of CPD-1023.

HPLC-MS elution method 1; retention time: 1.68 min; MS (positive ESI): found m/z 1049.1 [M+H]$^+$. $C_{40}H_{53}IN_6O_{19}$ (calc. 1049.2).

Example 10

Synthesis of CPD-1085

CPD-1084:

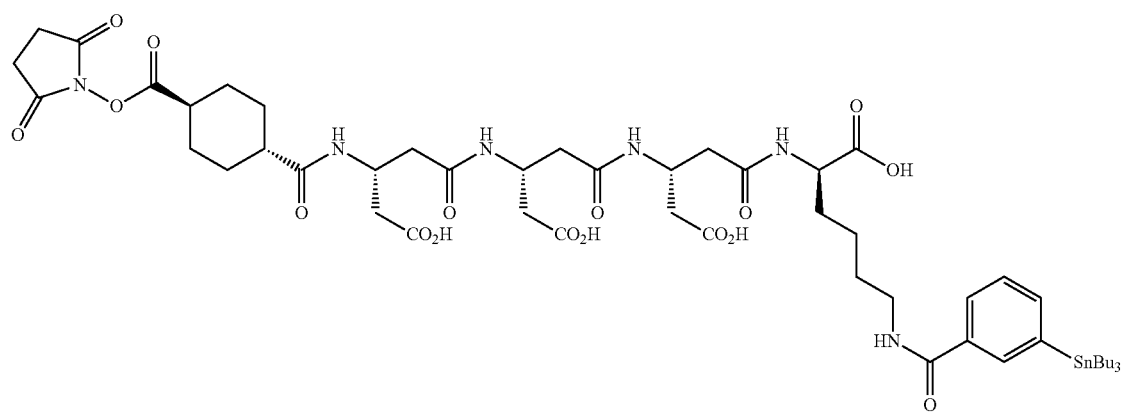

Starting from a β-peptide backbone (Fmoc-β-Glu-β-Glu-β-Glu-D-Lys-OH), which was prepared using standard solid phase peptide synthesis techniques, the title compound was prepared in a similar manner to the synthesis of CPD-1022.

HPLC-MS elution method 1; retention time: 3.21 min; MS (positive ESI): found m/z 1179.7 [M+H]$^+$. $C_{52}H_{79}N_6O_{17}Sn$ (calc. 1179.4).

CPD-1085:

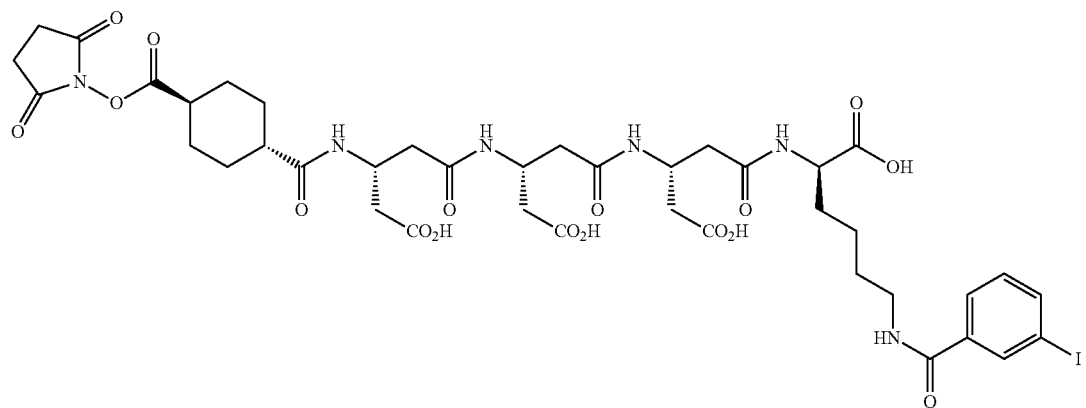 [SMILES: O=C(O)C[C@@H](CC(=O)N[C@@H](CC(=O)O)CC(=O)N[C@H](CCCCNC(=O)c1cccc(I)c1)C(=O)O)NC(=O)C[C@H](CC(=O)O)NC(=O)[C@H]1CC[C@H](C(=O)ON2C(=O)CCC2=O)CC1]

The title compound was prepared from CPD-1084 in a similar manner to the synthesis of CPD-1023.

HPLC-MS elution method 1; retention time: 1.68 min; MS (positive ESI): found m/z 1015.6 [M+H]$^+$. $C_{40}H_{52}N_6O_{17}$ (calc. 1015.2).

Example 11

Synthesis of CPD-1092

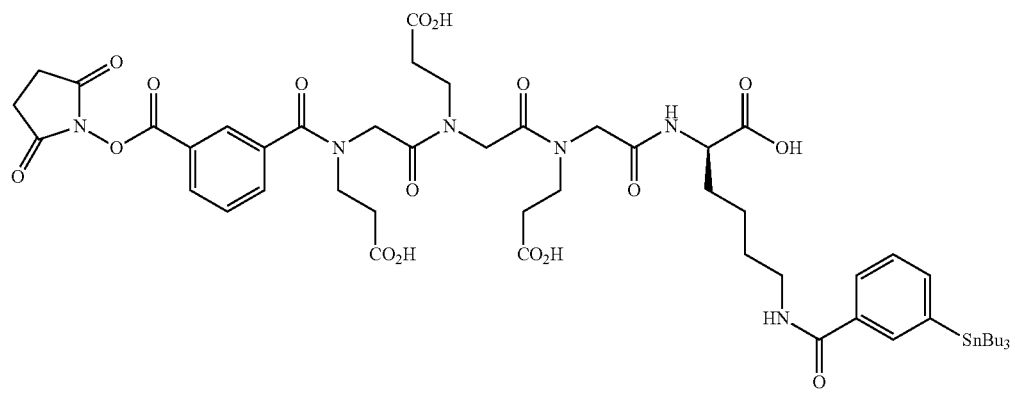

CPD-1091:

Starting from the hybrid backbone Fmoc-Nglu-Nglu-Nglu-D-Lys-OH, the title compound was prepared in a similar manner to the synthesis of CPD-1022.

HPLC-MS elution method 4; retention time: 6.60 min; MS (positive ESI): found m/z 1173.5 [M+H]$^+$. $C_{52}H_{73}N_6O_{17}Sn$ (calc. 1173.4).

CPD-1092:

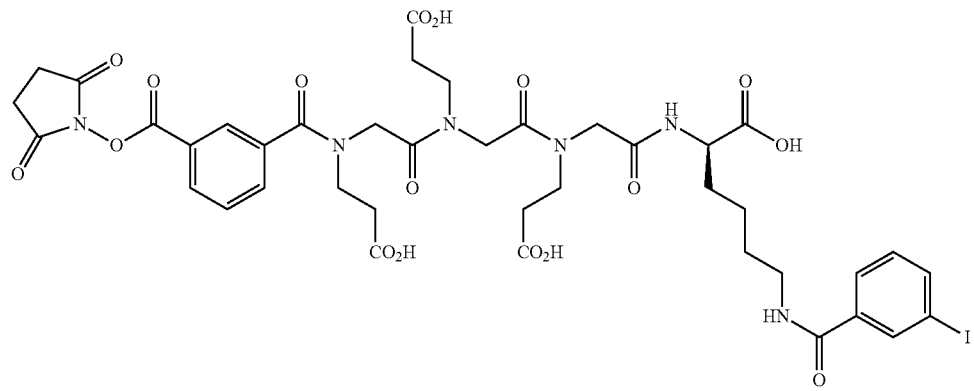 [SMILES: O=C(O)CCN(CC(=O)N[C@H](CCCCNC(=O)c1cccc(I)c1)C(=O)O)C(=O)CN(CCC(=O)O)C(=O)CN(CCC(=O)O)C(=O)c1cccc(C(=O)ON2C(=O)CCC2=O)c1]

The title compound was prepared in a similar manner to the synthesis of CPD-1023.

HPLC-MS elution method 1; retention time: 1.74 min; MS (positive ESI): found m/z 1009.4 [M+H]$^+$. $C_{40}H_{46}IN_6O_{17}$ (calc. 1009.2).

Example 12

Synthesis of CPD-1098

CPD-1097:

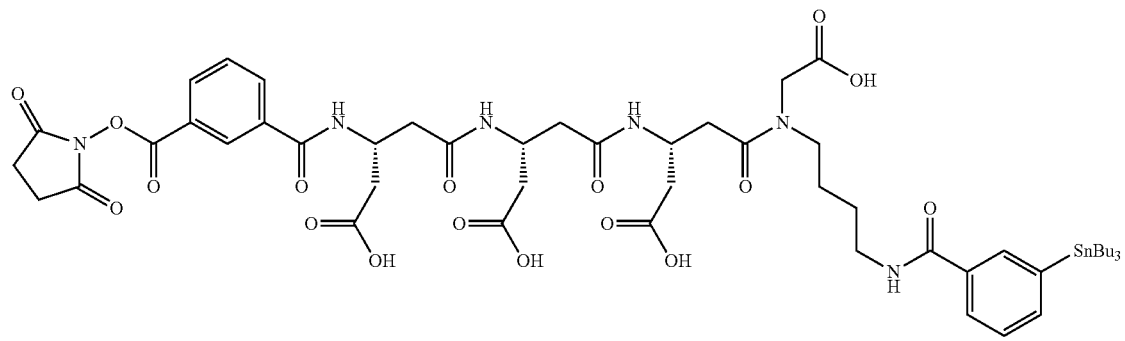

Starting from the hybrid backbone Fmoc-β-Glu-β-Glu-β-Glu-Nlys-OH, the title compound was prepared in a similar manner to the synthesis of CPD-1022.

HPLC-MS elution method 1; retention time: 3.23 min; MS (positive ESI): found m/z 1173.5 [M+H]$^+$. $C_{52}H_{73}N_6O_{17}Sn$ (calc. 1173.4).

CPD-1098:

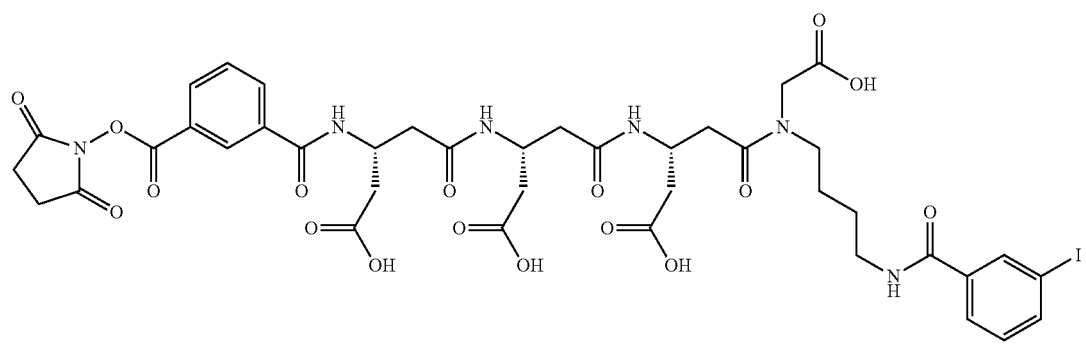 [SMILES: O=C(O)C[C@@H](CC(=O)N[C@@H](CC(=O)O)CC(=O)N(CCCCNC(=O)c1cccc(I)c1)CC(=O)O)NC(=O)C[C@H](CC(=O)O)NC(=O)c1cccc(C(=O)ON2C(=O)CCC2=O)c1]

The title compound was prepared from CPD-1097 in a similar manner to the synthesis of CPD-1023.

HPLC-MS elution method 1; retention time: 1.70 min; MS (positive ESI): found m/z 1009.4 [M+H]$^+$. $C_{40}H_{46}IN_6O_{17}$ (calc. 1009.2).

Example 13

Synthesis of CPD-1102

CPD-1101:

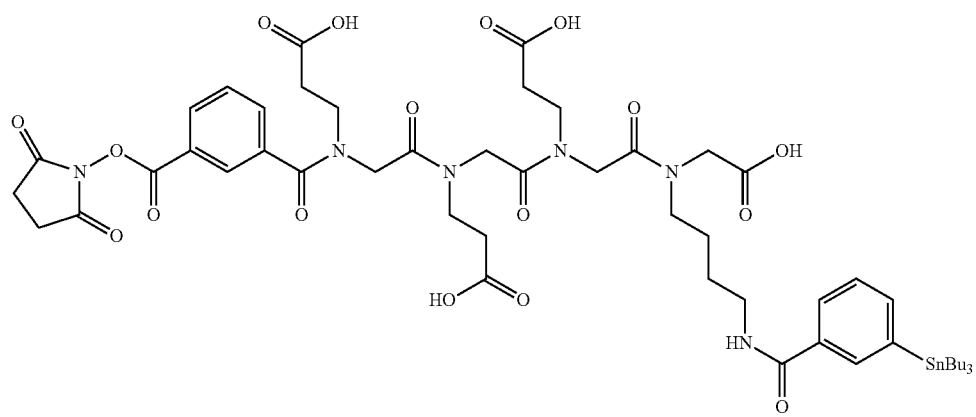

Starting from the peptoid backbone Fmoc-Nglu-Nglu-Nglu-Nlys-OH, the title compound was prepared in a similar manner to the synthesis of CPD-1022.

HPLC-MS elution method 1; retention time: 3.29 min; MS (positive ESI): found m/z 1174.0 [M+H]$^+$. $C_{52}H_{73}N_6O_{17}Sn$ (calc. 1173.4).

CPD-1102:

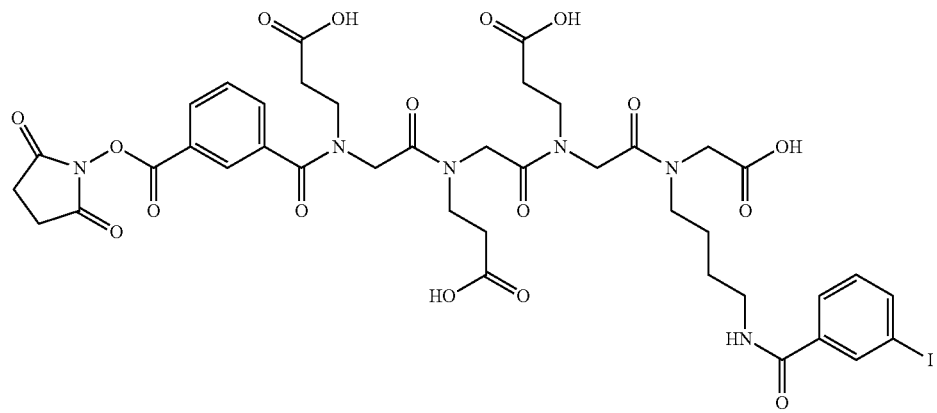 [SMILES: O=C(O)CCN(CC(=O)N(CCCCNC(=O)c1cccc(I)c1)CC(=O)O)C(=O)CN(CCC(=O)O)C(=O)CN(CCC(=O)O)C(=O)c1cccc(C(=O)ON2C(=O)CCC2=O)c1]

The title compound was prepared from CPD-1101 in a similar manner to the synthesis of CPD-1023.

HPLC-MS elution method 1; retention time: 1.75 min; MS (positive ESI): found m/z 1009.1 [M+H]$^+$. $C_{40}H_{46}IN_6O_{17}$ (calc. 1009.2).

Example 14

Synthesis of CPD-1094

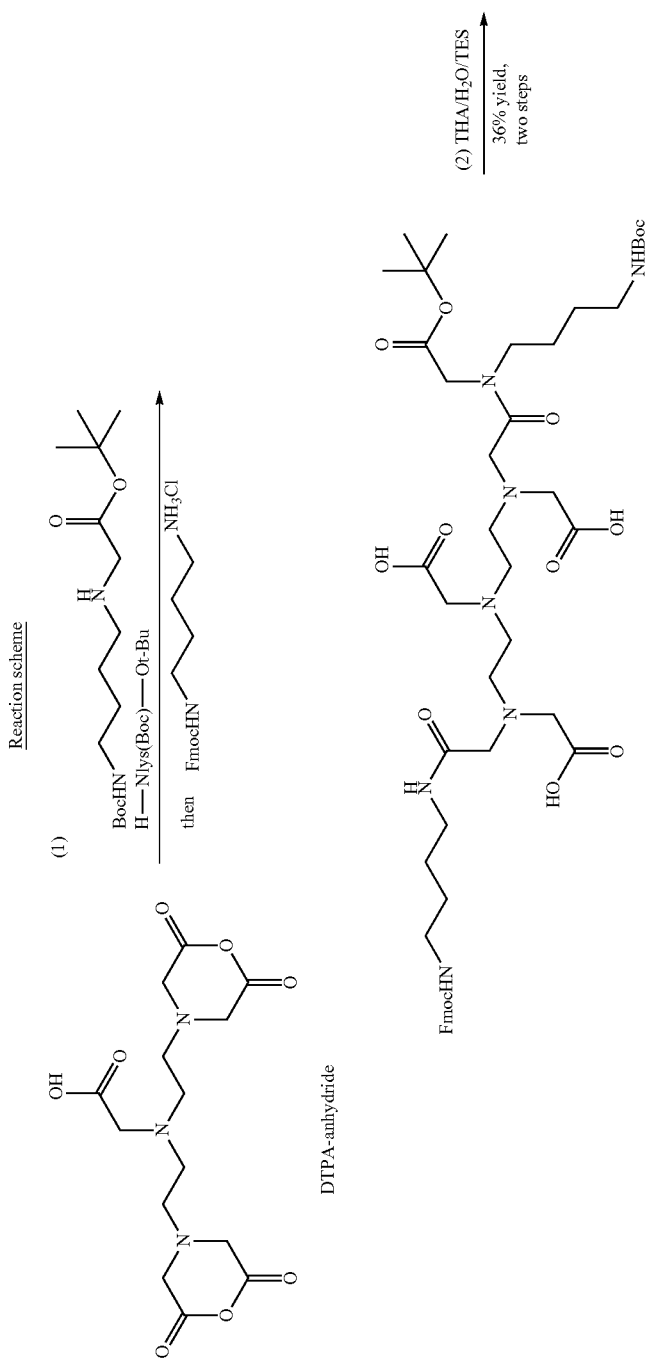

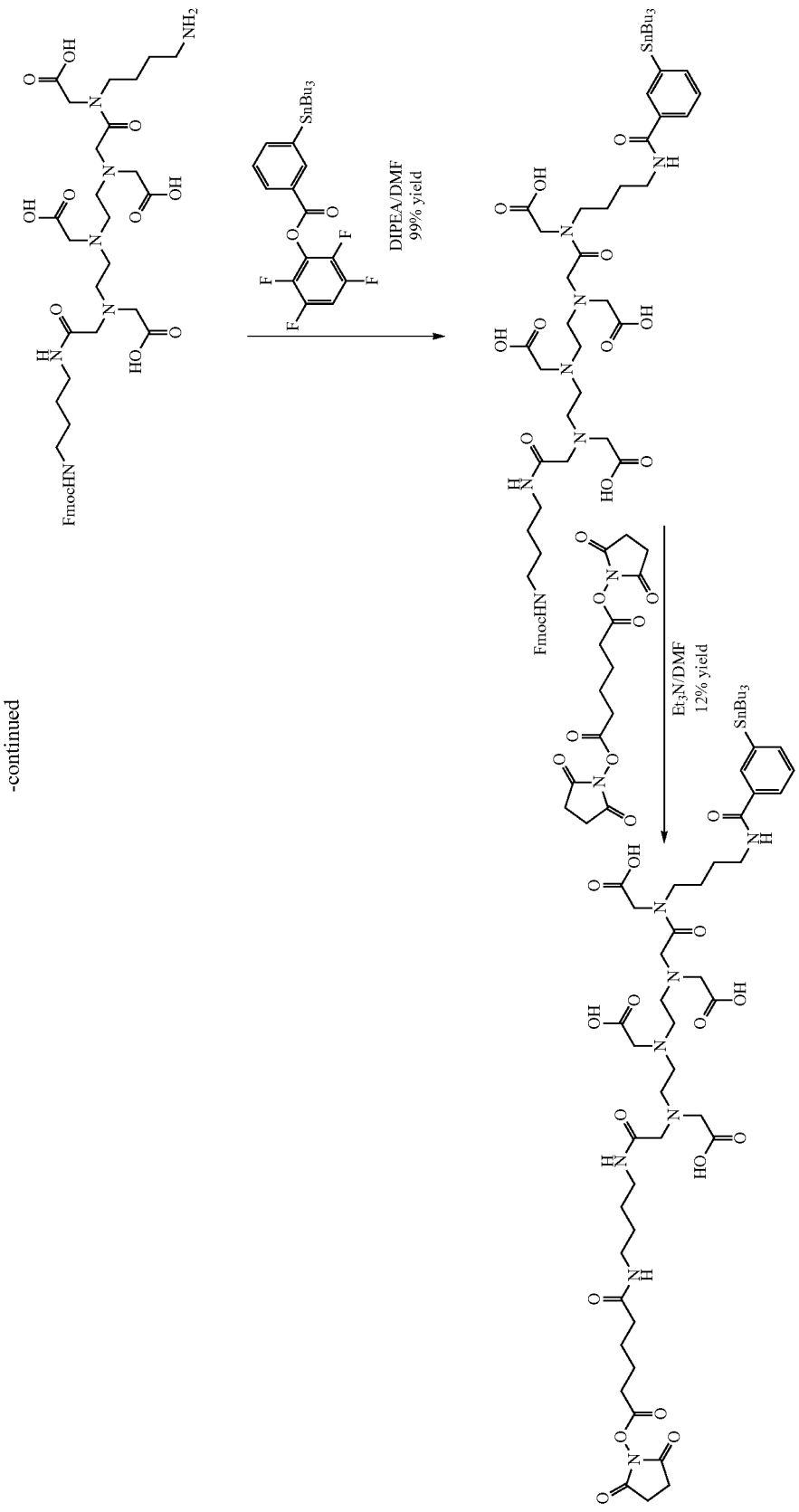

Polyamine Backbone (Free Amine):

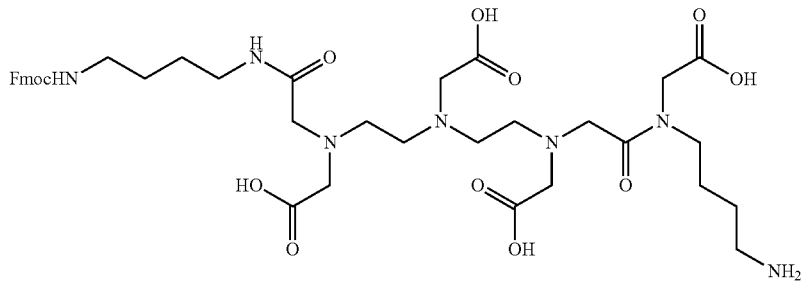

To a solution of DTPA-anhydride (0.150 g, 0.419 mmol) in 2 mL of DMF was added H-Nlys(Boc)-Ot-Bu (0.152 g, 0.502 mmol). The reaction mixture was stirred at room temperature for 1 hour before the addition of N-Fmoc-1,4-butanediamine hydrochloride salt (0.146 g, 0.419 mmol). After an additional 1 hour of stirring the mixture was diluted with diethyl ether (25 mL) and the suspension centrifuged at 4000 rpm for 15 minutes. The white precipitate was then collected and treated with a mixture of TFA/water/TES (95:2.5:2.5 v/v/v, 2 mL) at room temperature for 2 hours. Volatiles were removed under vacuum and the residue purified by preparative-HPLC (method 5, retention time: 8.9 min) to produce the desired product as an amorphous white solid (0.123 g, 0.151 mmol, 36% yield).

HPLC-MS elution method 4; retention time: 2.97 min; MS (positive ESI): found m/z 814.5 $[M+H]^+$. $C_{39}H_{56}N_7O_{12}$ (calc. 814.4).

Polyamine Backbone (Stannane):

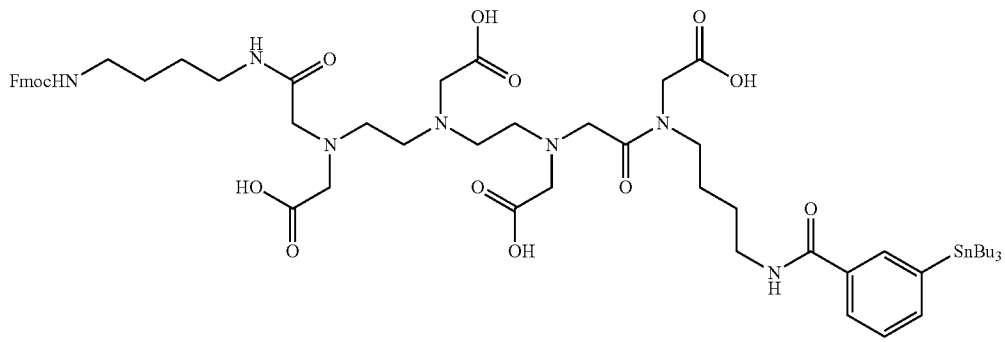

To a solution of the polyamine backbone (62 mg, 0.076 mmol) in 1.0 mL of DMF were added 2,3,5,6-tetrafluorophenyl 3-tributylstannylbenzoate (84 mg, 0.151 mmol) and diisopropylethylamine (30 µL, 0.172 mmol) at room temperature. The reaction solution was stirred for 1 hour and then diluted with a mixture of cold diethyl ether (25 mL). The resultant suspension was centrifuged at 4000 rpm for 15 minutes and the white precipitate collected and washed with 20 mL of cold diethyl ether. This intermediate (91 mg, 0.075 mmol, 99% yield) was used in the next step without further purification. HPLC-MS elution method 1; retention time: 3.42 min; MS (positive ESI): found m/z 1208.5 $[M-H]^+$. $C_{58}H_{86}N_7O_{13}Sn$ (calc. 1208.5).

CPD-1094:

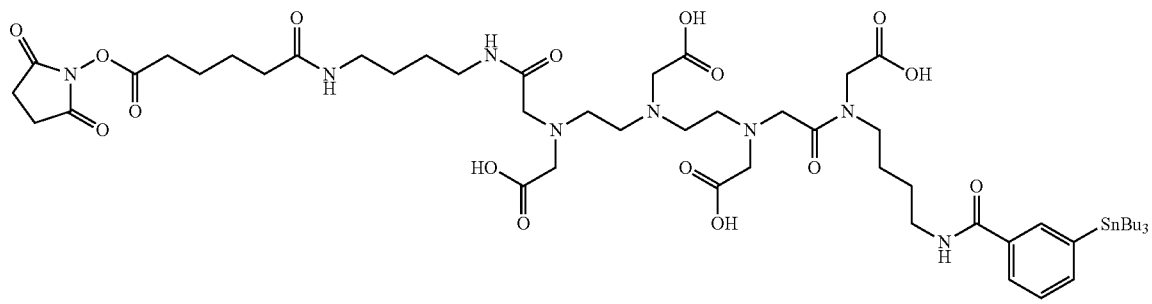

To a solution of the above polyamine-stannane (45 mg, 0.037 mmol) and adipic acid bis-NHS active ester (0.127 g, 0.372 mmol) in 1 mL of DMF was added triethylamine (0.20 mL) at room temperature. The reaction mixture was stirred at room temperature for 12 hours before dilution with diethyl ether (25 mL). The resultant suspension was centrifuged at 4000 rpm for 15 minutes and the solid collected. Purification was accomplished by preparative-HPLC (method 6, retention time: 7.7 min) to yield the final product as an amorphous white solid (6.5 mg, 5.4 μmol, 12% yield).

HPLC-MS elution method 1; retention time: 3.00 min; MS (positive ESI): found m/z 1211.6 [M+H]$^+$. $C_{53}H_{87}N_8O_{16}Sn$ (calc. 1211.5).

CPD-1095:

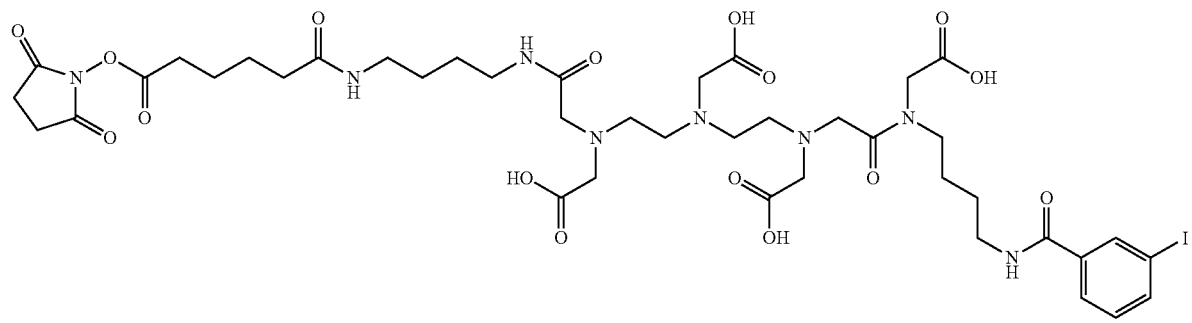 [SMILES: O=C(O)CN(CCN(CC(=O)O)CC(=O)NCCCCNC(=O)CCCCC(=O)ON1C(=O)CCC1=O)CCN(CC(=O)O)CC(=O)N(CCCCNC(=O)c1cccc(I)c1)CC(=O)O]

The title compound was prepared from CPD-1094 in a similar manner to the synthesis of CPD-1023.

HPLC-MS elution method 1; retention time: 1.61 min; MS (positive ESI): found m/z 1047.5 [M+H]$^+$. $C_{41}H_{60}IN_8O_{16}$ (calc. 1047.3).

Example 15

Radiochemistry

All compounds were prepared using the following general procedure described for the radiolabeling of CPD1028 with Na$^{131}$I. Table 3 describes representative labeling results for some of the different residualizing linkers described herein.

Radiolabeling Precursor CPD1022 with Na$^{131}$I to Prepare CPD1028

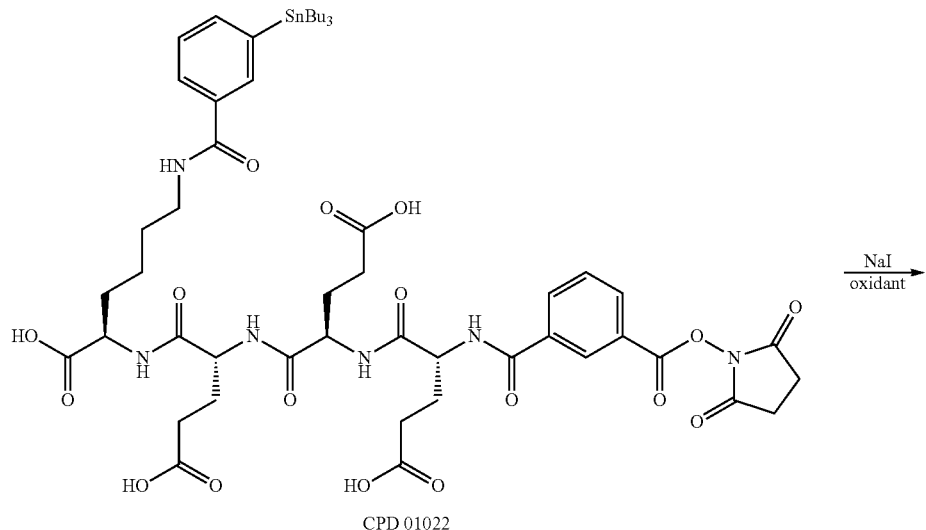

CPD 01022

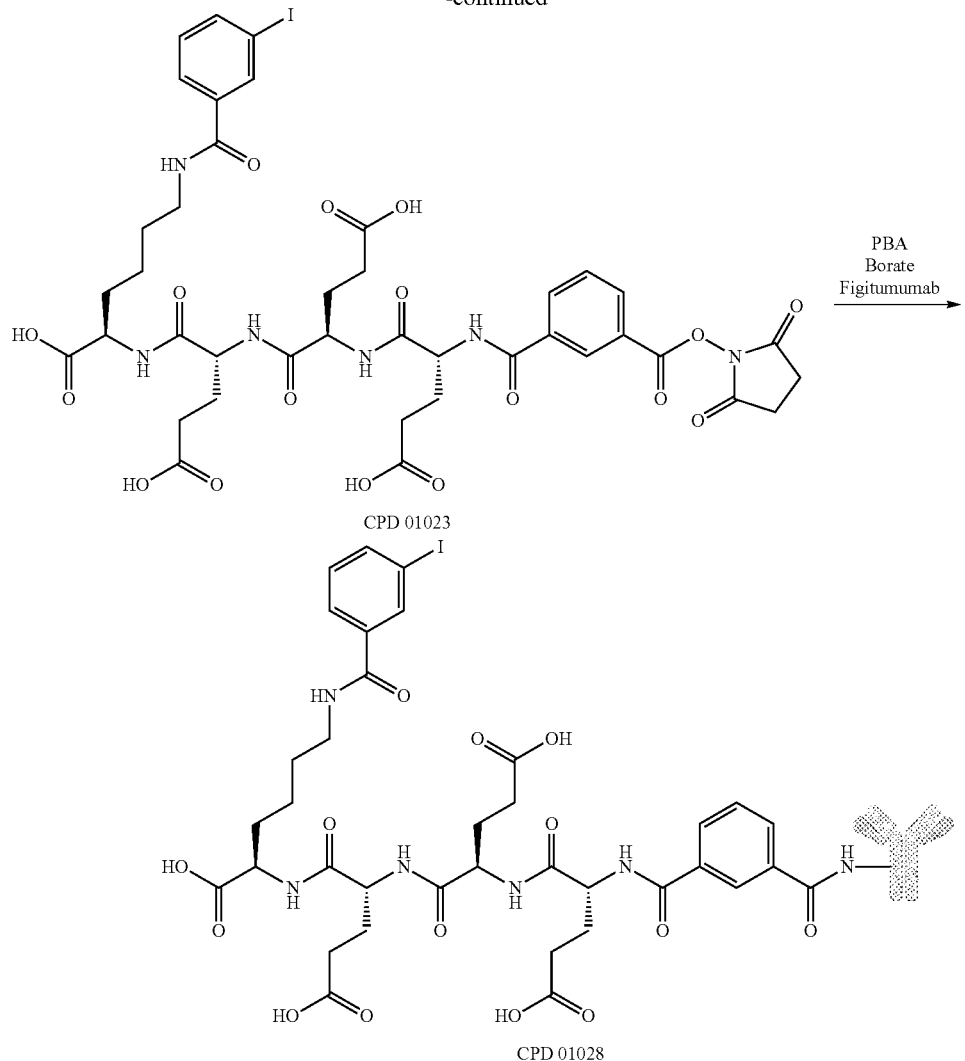

CPD 01023

CPD 01028

Precursor CPD 1022 (80 µg) was dissolved in 50 µL of acetonitrile and added to a 20 mL scintillation vial. Sodium iodide (Na$^{131}$I, 20 µL) was premixed with 5 uL of acetic acid in a 1.5 mL plastic vial and subsequently added to the scintillation vial containing the precursor. Iodogen (5 µL of a 1 mg/mL solution in acetonitrile) was added and the resultant solution allowed to stand for 5 minutes at room temperature after which the reaction was quenched with 25 µL of sodium thiosulfate. Intermediate radiolabeled linker CPD1023 was then purified via HPLC.

Purified HPLC fractions of CPD1023 were combined and dried under vacuum in a 60° C. water bath. The vial was further dried with 2×200 µL of EtOH to remove any residual TFA. The resulting residue was dissolved in 20% DMSO in PBS (containing 0.01% Tween80), vortexed and centrifuged. To this vial was added 10 µL of figitumumab followed by 5 µL of borate buffer (0.1M, pH=8.5) and allowed to sit at room temperature for 2 hours. The crude conjugated product was subsequently purified via a Sephadex packed column containing 35 mm G50 resin in a 1 mL housing. The final radiolabeled product, CPD 1028 was eluted from the column with PBS containing 0.01% Tween80 in high purity as analyzed by SEC and iTLC for purity.

TABLE 3

Residualizing radiolabeled antibodies

| Final Product | Precursor | Precursor Standard | Radiochemical Yield (%) | | | Radiochemical Purity | Specific Activity (□Ci/□g) |
|---|---|---|---|---|---|---|---|
| | | | Labeling | Conjugation | Overall | | |
| 1028 | 1022 | 1023 | 80 | 43 | 33 | 98 | 14 |
| 1028 | 1051 | 1052 | 55 | 75 | 20 | 98 | 15.1 |
| 1049 | 1054 | 1055 | 62 | 18 | 6 | 95 | 7 |

TABLE 3-continued

Residualizing radiolabeled antibodies

| Final Product | Precursor Precursor | Precursor Standard | Radiochemical Yield (%) Labeling | Conjugation | Overall | Radiochemical Purity | Specific Activity (☐Ci/☐g) |
|---|---|---|---|---|---|---|---|
| 1068 | 1066 | 1067 | 56 | 36 | 20 | 99 | 4.4 |
| 1073 | 1071 | 1072 | 82 | 50 | 20 | 96 | 12.5 |
| 1074 | 1080 | 1081 | 74 | 46 | 33 | 96 | 14.2 |
| 1079 | 1084 | 1085 | 34 | 56 | 18 | 96 | 13.7 |
| 1093 | 1091 | 1092 | 80 | 33 | 23 | 99 | 14.6 |
| 1096 | 1094 | 1095 | 43 | 40 | 17 | 99 | 9.4 |
| 1100 | 1097 | 1098 | 81 | 41 | 32 | 98 | 16.4 |
| 1104 | 1101 | 1102 | 77 | 41 | 30 | 99 | 11 |
| 1106 | 1022 | 1023 | 72 | 8.5 | 6 | 99 | 5.6 |

Note:
Most compounds were labeled with antibody Figitumumab with the exception of 1106 which used an anti-EGFR clone 528 monoclonal antibody

Example 16

In Vitro Evaluation

Saturation Binding Experiments

Saturation binding experiments measure the specific binding at equilibrium of a radioligand at various concentrations in order to determine the Kd (ligand concentration that binds to half the receptor sites at equilibrium) and Bmax (maximum number of binding sites). In this type of binding assay, both total and nonspecific binding are measured, where specific binding to the receptor is calculated by subtracting the difference. Nonspecific binding is typically assessed by measuring radioligand binding in the presence of a fixed concentration of an unlabeled compound that binds to essentially all the receptors. Since all the receptors are occupied by the unlabeled drug, the radioligand only binds nonspecifically. Kd and Bmax values are calculated by nonlinear regression analysis and computerized curve fitting.

The purpose of this assay was to ensure that these new radiolabelled conjugates maintained binding characteristics consistent with the native antibody in an IGF-1R expressing A431 cell line. Twenty-four hours prior to the start of the experiment, $1.5 \times 10^5$ A431 cells were seeded in 48-well microplates in 500 µl supplemented medium. The labeled conjugate was diluted with binding buffer (PBS+0.5% BSA) to a range of concentrations from 0.08 nM to 40 nM; final assay concentration 0.04 to 20 nM. At the start of the assay, the media is aspirated, discarded and 500 µl of serum-free DMEM was added to each well. The plates were incubated at 37° C. for 1 h. Following incubation, media was aspirated from each well and discarded. The cells were washed and 100 µl of binding buffer (total binding) or 4 µM cold-antibody (non-specific binding) added to designated wells. Plates were incubated at 4° C. for 1 h with mild shaking. Following the blocking step, 100 µl of labeled conjugate was added to each well. The plates were then incubated at 4° C. for 2 h. Following incubation, the contents of each well was aspirated and discarded. The cells were washed twice with PBS and were then lysed with 1% Triton-X-100. The lysates were transferred to counting tubes and run with labeled conjugate standards on the Wizard 1470 gamma counter to determine the radioactivity content (in counts per minute (CPM)) for each lysate. The remaining lysate from each well (254 was transferred to a 96-well plate, and the protein content of each lysate determined using a standard protein quantification assay. Total, non-specific and specific ligand binding determinations, mass of bound conjugate in each lysate were calculated by converting lysate CPM to fmol bound using the specific activity of the conjugate standards and then normalizing the fmol bound to the protein content of each lysate (in milligrams). Specific binding was determined by subtracting the non-specific binding from total binding. Total, specific and non-specific binding values (fmol/mg) were plotted (y-axis) against conjugate concentration (nM, x-axis) as shown in FIG. 1. The $K_d$ and $B_{max}$ were derived by curve fitting of the specific binding data to a single-site hyperbola model (GraphPad Prism Software).

Residualization

The residualization assay was designed to determine the degree of cell retention of radiolabeled-linker-antibody derivatives. The assay relies on the inherent ability of the IGF-1 receptor to internalize when bound to ligand and the ability to track radiolabelled compounds. In this type of binding experiment, a constant amount of radioligand is incubated with an IGF-1R expressing cell line for a fixed period of time. Following incubation, the cells are stripped with a mild acid buffer to remove any external or membrane-bound radioligand. Fresh medium is reapplied and the cells are again incubated for a pre-determined amount of time. It is during this period that cell processes degrade the radioligand and thereby efflux radioactive fragments back into the culture medium or retain the radioactive fragments in the cell. Residualization is determined by calculating the amount of internalized radioactivity as a percentage of the total cell-associated activity following acid wash.

Figure 2:
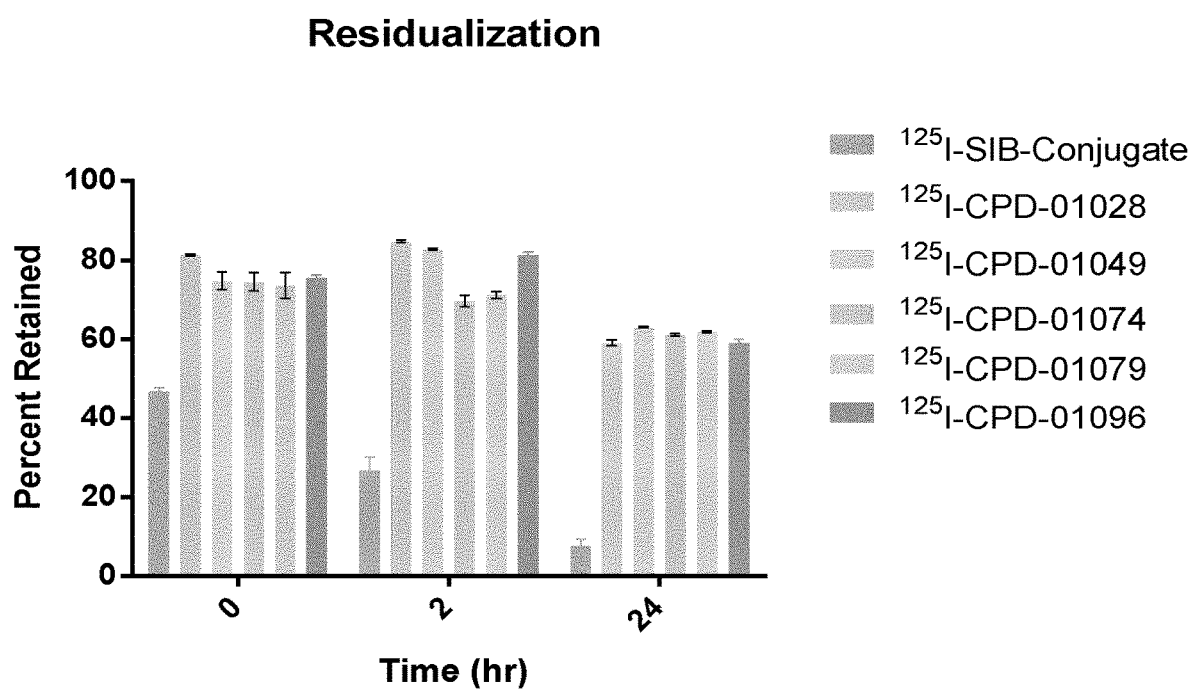
FIG. 2 is a graph illustrating residualization of select conjugates.

A431 cells were plated in 24-well plates at a concentration of $2.5 \times 10^5$ cells/well in full medium (DMEM). Following overnight incubation, the cells were changed to serum-free DMEM and incubated for 1 hour at 37° C. Media was decanted and plates were washed once with sterile PBS. Labeled conjugate was diluted in serum-free DMEM to a concentration of 2 nM. 500 uL of radioligand was loaded into each well and incubated for 4 hours at 37° C. After incubation, plates were immediately placed on ice and medium was discarded into pre-labeled (non-bound) gamma counting tubes. Cells were washed once with sterile PBS, gently shaken and decanted into the (non-bound) gamma tubes. Mild acid wash buffer (pH 4.6, 500 µL) was added into all wells. Plates were incubated at 4° C. for 15 minutes and buffer was collected into pre-labeled gamma-counting tubes (membrane-bound). 1 ml of warmed serum-free media was added to all wells and plates were incubated at 37° C., for 0, 2 and 24 h. Following the prescribed incubation, plates were placed on ice and processed in the following manner. Media was decanted and collected into labeled (efflux)

gamma tubes. Plates were then washed once with 1 ml cold PBS and collected into efflux tubes. Acid wash buffer (pH 2.5, 500 µL) was added to all wells and plates were incubated for 5 minutes on ice. The acid wash fraction was then collected into labeled (recycled) gamma tubes. Cells were lysed with 300 µL 1% Triton X-100 for 30 minutes at room temperature. 250 µL of the cell lysate was transferred into gamma counting tubes and counted for 10 minutes. 25 µL of the cell lysate fraction was transferred to a 96-well plate for protein quantification (Pierce BCA Protein Assay). Percent residualization (FIG. 2) was determined as CPM (lysate)/CPM (efflux+recycled+lysate).

Example 17

Diagnostic and Radiation Treatment Planning Use

Antibody-linker conjugates prepared by these means can used for diagnostic purposes including but not limited to detection of antigen expressing tumors and/or for measuring antigen biomarker levels to obtain biochemical or pathological information about course of disease, severity of disease, change in disease phenotype or indicate treatment planning. For example, high levels of antigen target expression in tumors measured by imaging antibody-linker conjugates in patients may be indicative of developing resistance to an ongoing chemotherapeutic treatment and provide information to enable change of a current course of treatment. High levels of target antigen in tumors measured by antibody-linker conjugate imaging may indicate aggressive, proliferative or metastatic disease and dictate subsequent treatment. Another example is that detection of antigen on target expressing tumors by imaging with an antibody-linker conjugate may indicate therapeutic efficacy of the same conjugate labeled with a therapeutic radioisotope or any other suitable chemotherapeutic in the form of an antibody drug conjugate. Follow up diagnostic imaging of an appropriate biomarker with an antibody-linker conjugate is also useful for tracking patient response to an ongoing treatment plan.

Other Embodiments

All patents, patent applications, and publications mentioned in this specification are herein incorporated by reference, to the same extent as if each independent patent, patent application, or publication was specifically and individually indicated to be incorporated by reference.

What is claimed is:
1. A conjugate, selected from the group consisting of:
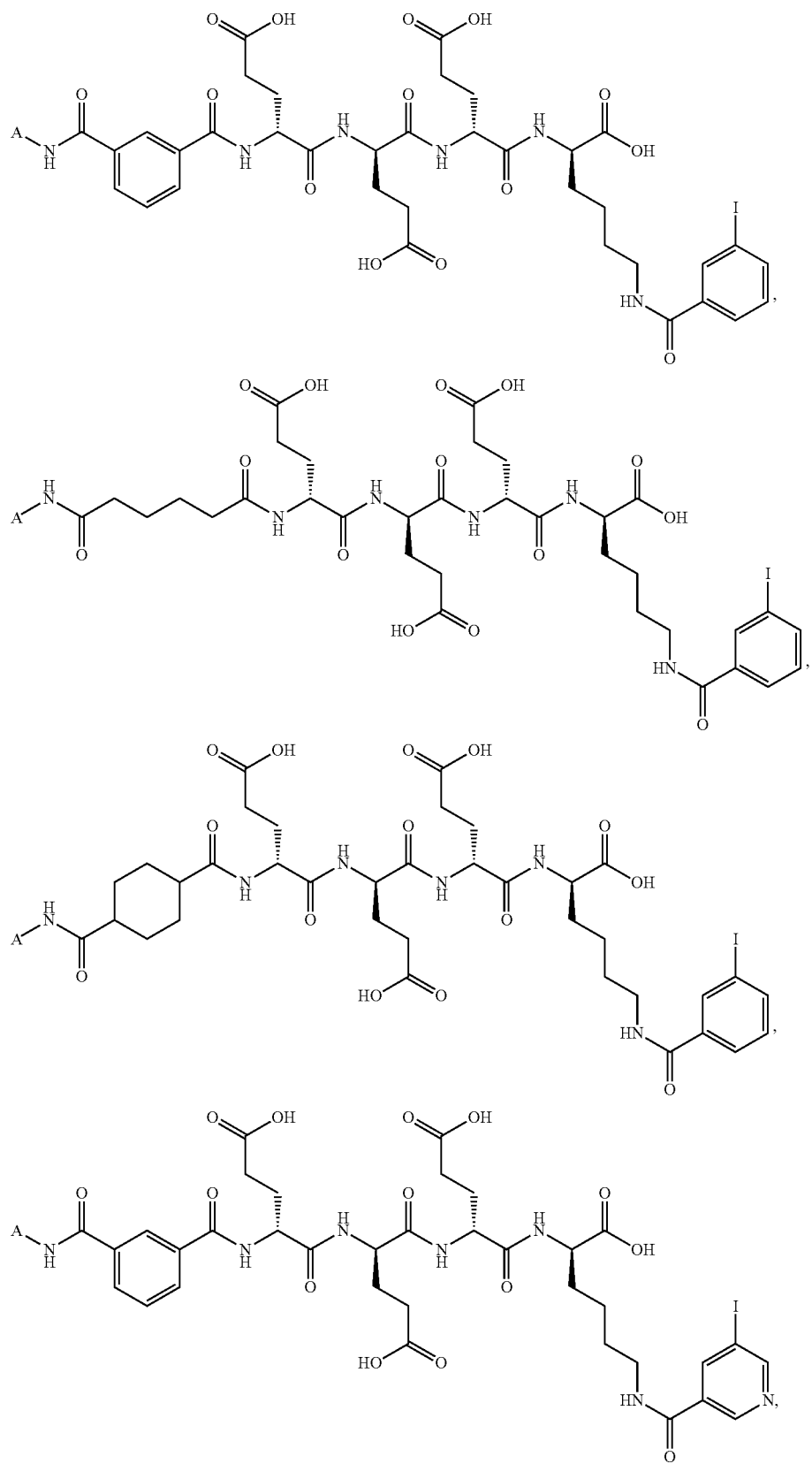

-continued
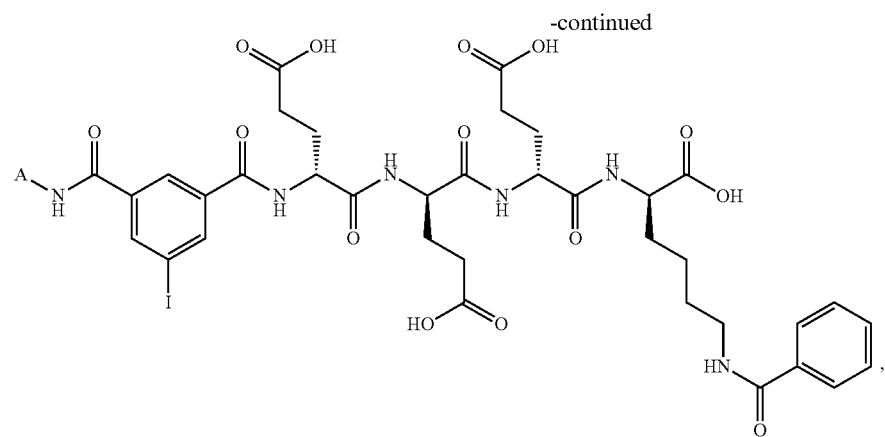
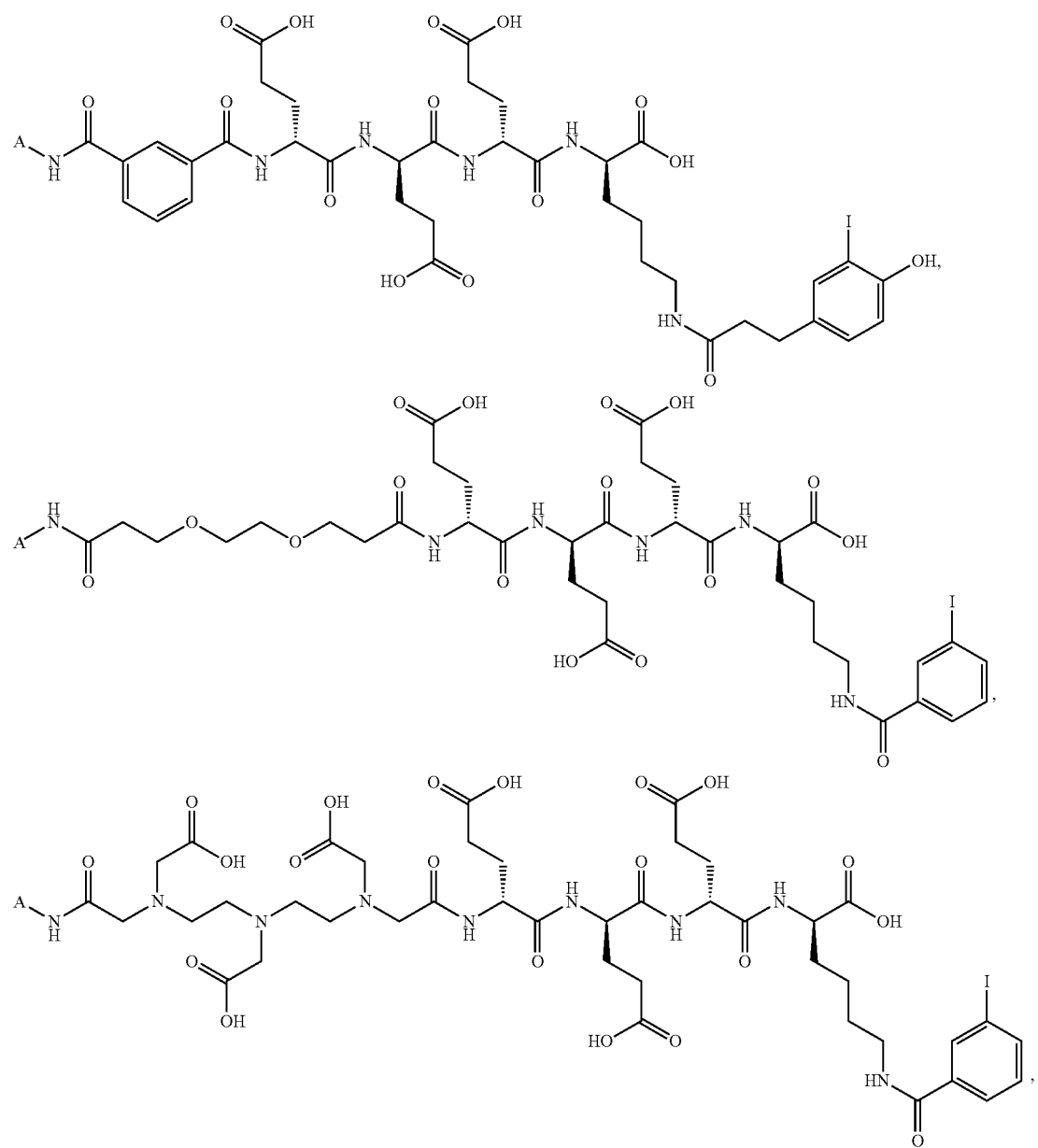

-continued
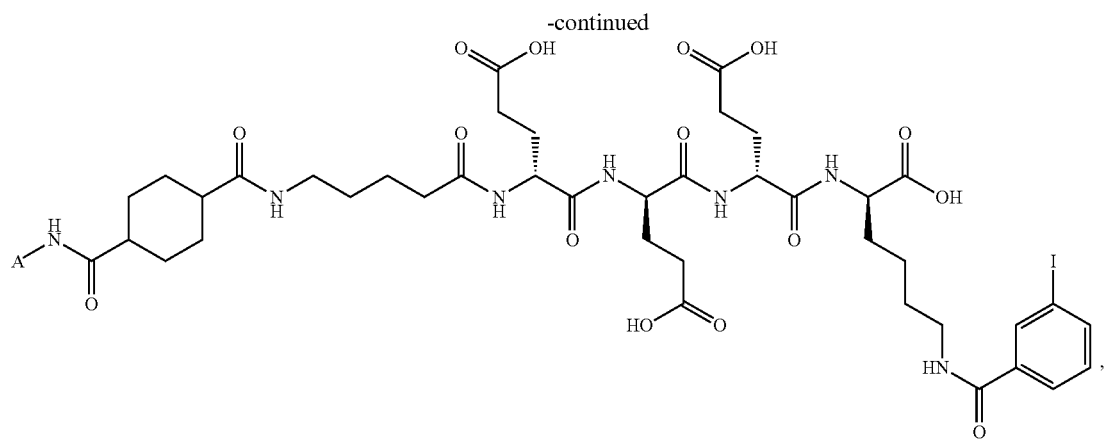
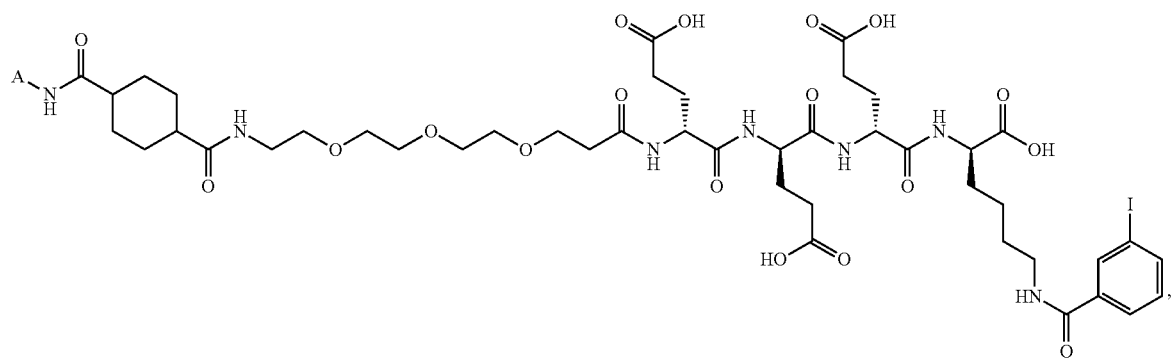
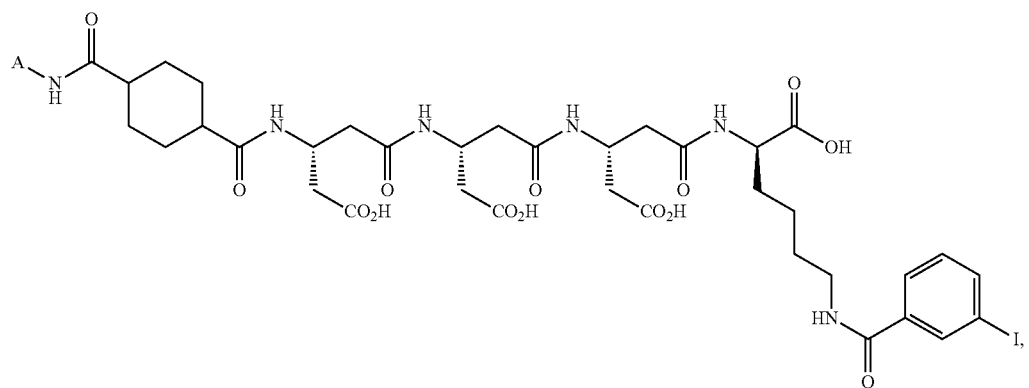
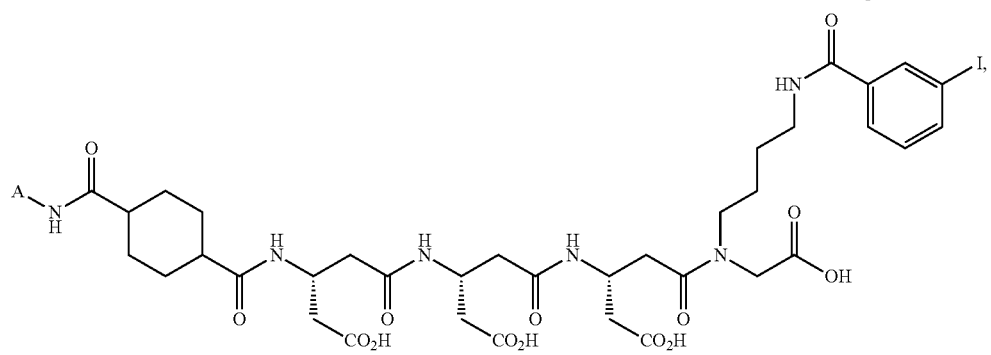

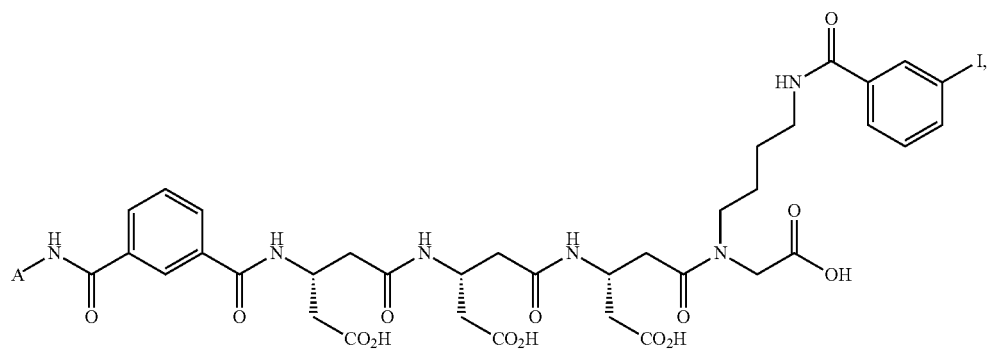
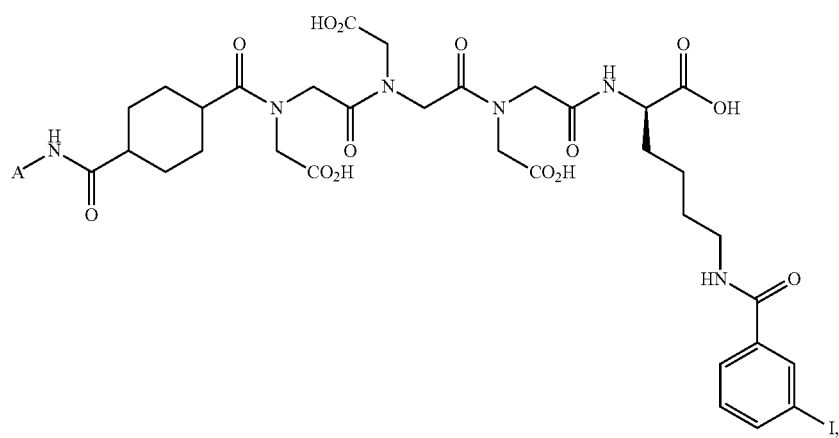
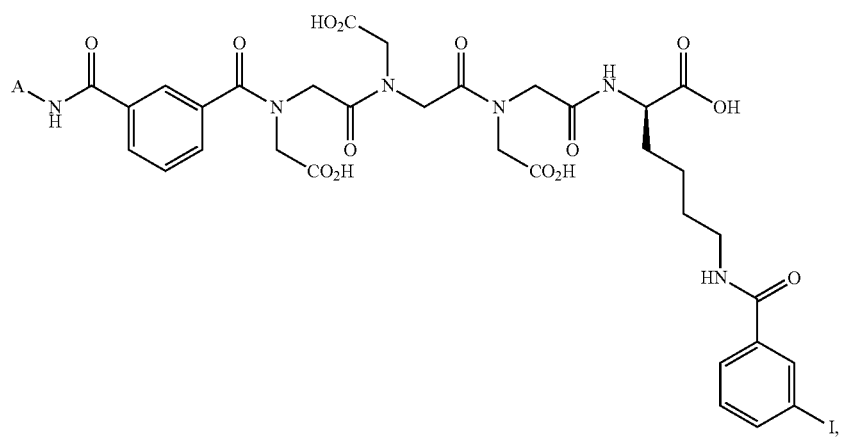
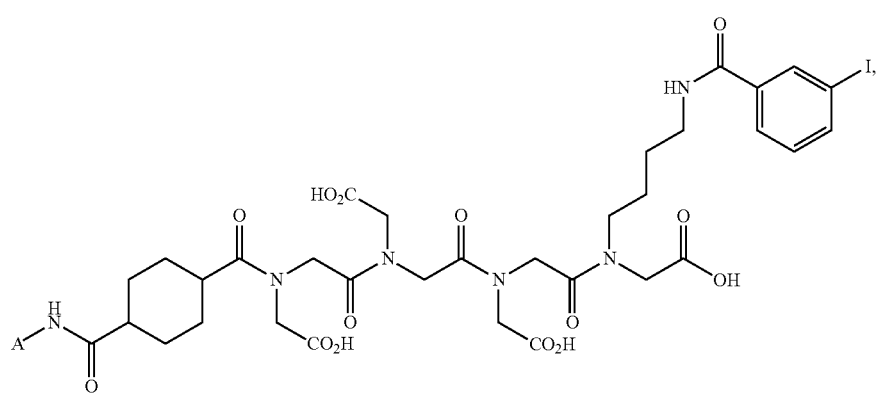

-continued
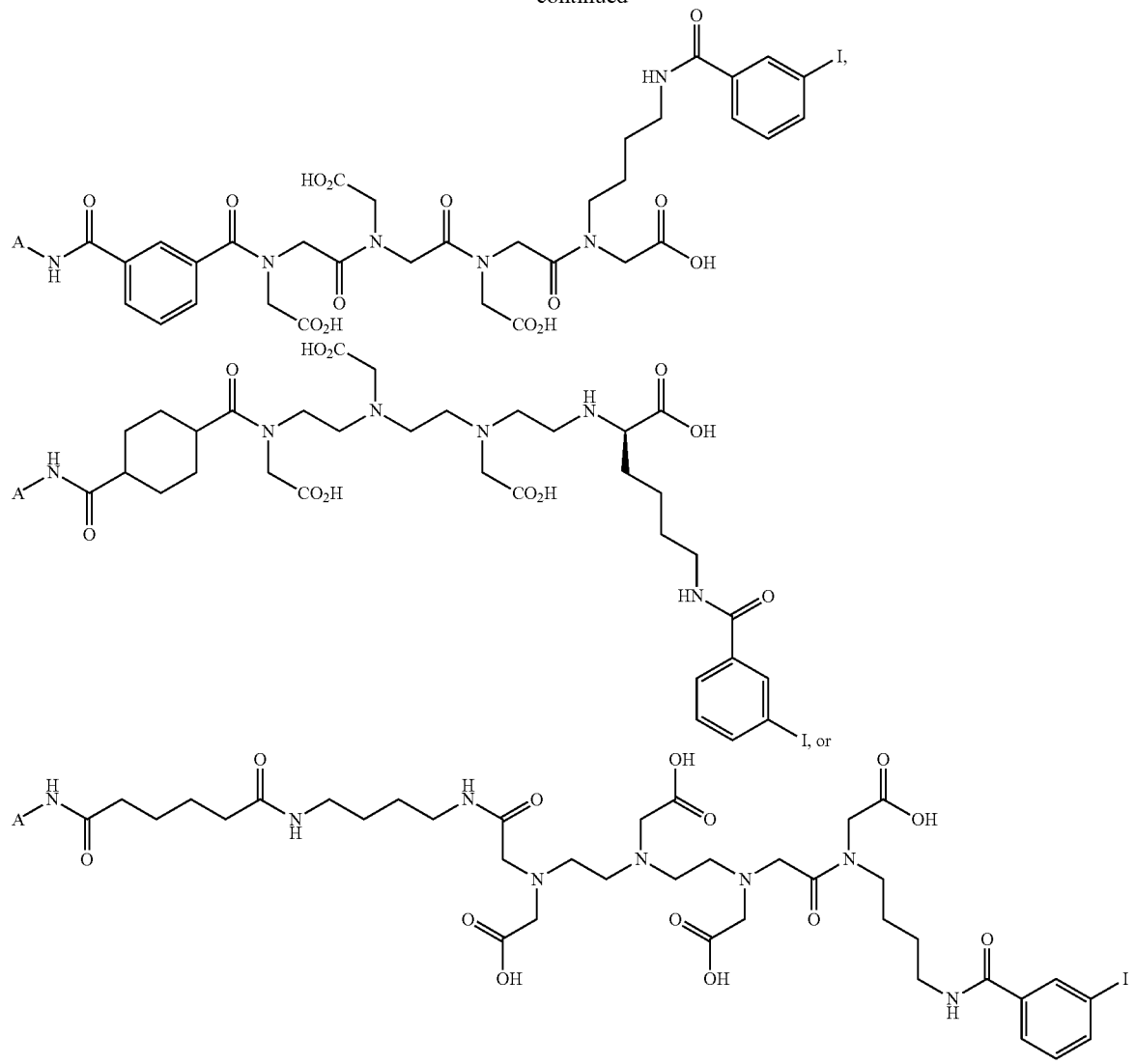
wherein the iodine atom is $^{123}$I, $^{124}$I, $^{125}$I, or $^{131}$I and A-NH is a polypeptide.
* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Homo sapiens

<400> SEQUENCE: 1

Gly Phe Thr Phe Ser Ser Tyr Ala Met Asn
1               5                   10

<210> SEQ ID NO 2
<211> LENGTH: 16
<212> TYPE: PRT
<213> ORGANISM: Homo sapiens

<400> SEQUENCE: 2

Ala Ile Ser Gly Ser Gly Gly Thr Thr Phe Tyr Ala Asp Ser Val Lys
1               5                   10                  15

<210> SEQ ID NO 3
<211> LENGTH: 16
<212> TYPE: PRT
<213> ORGANISM: Homo sapiens

<400> SEQUENCE: 3

Asp Leu Gly Trp Ser Asp Ser Tyr Tyr Tyr Tyr Gly Met Asp Val
1               5                   10                  15

<210> SEQ ID NO 4
<211> LENGTH: 11
<212> TYPE: PRT
<213> ORGANISM: Homo sapiens

<400> SEQUENCE: 4

Arg Ala Ser Gln Gly Ile Arg Asn Asp Leu Gly
1               5                   10

<210> SEQ ID NO 5
```

```
<211> LENGTH: 7
<212> TYPE: PRT
<213> ORGANISM: Homo sapiens

<400> SEQUENCE: 5

Ala Ala Ser Arg Leu His Arg
1               5

<210> SEQ ID NO 6
<211> LENGTH: 10
<212> TYPE: PRT
<213> ORGANISM: Homo sapiens

<400> SEQUENCE: 6

Leu Gln His Asn Ser Tyr Pro Cys Ser Phe
1               5                   10

<210> SEQ ID NO 7
<211> LENGTH: 124
<212> TYPE: PRT
<213> ORGANISM: Homo sapiens

<400> SEQUENCE: 7

Val Gln Leu Leu Glu Ser Gly Gly Gly Leu Val Gln Pro Gly Gly Ser
1               5                   10                  15

Leu Arg Leu Ser Cys Thr Ala Ser Gly Phe Thr Phe Ser Ser Tyr Ala
            20                  25                  30

Met Asn Trp Val Arg Gln Ala Pro Gly Lys Gly Leu Glu Trp Val Ser
        35                  40                  45

Ala Ile Ser Gly Ser Gly Gly Thr Thr Phe Tyr Ala Asp Ser Val Lys
    50                  55                  60

Gly Arg Phe Thr Ile Ser Arg Asp Asn Ser Arg Thr Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Leu Gly Trp Ser Asp Ser Tyr Tyr Tyr Tyr Gly Met Asp
            100                 105                 110

Val Trp Gly Gln Gly Thr Thr Val Thr Val Ser Ser
        115                 120

<210> SEQ ID NO 8
<211> LENGTH: 107
<212> TYPE: PRT
<213> ORGANISM: Homo sapiens

<400> SEQUENCE: 8

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys
```

<210> SEQ ID NO 9
<211> LENGTH: 440
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Thr Thr Phe Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Trp Ser Ser Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

```
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr
            435                 440

<210> SEQ ID NO 10
<211> LENGTH: 214
<212> TYPE: PRT
<213> ORGANISM: Homo sapiens

<400> SEQUENCE: 10

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```